United States Patent
Park et al.

(10) Patent No.: US 11,806,078 B1
(45) Date of Patent: Nov. 7, 2023

(54) TEAR MENISCUS DETECTION AND EVALUATION SYSTEM

(71) Applicant: Globe Biomedical, Inc., Riverside, CA (US)

(72) Inventors: Joshua Park, Riverside, CA (US); Rehan Ahmed, Riverside, CA (US); Douglas Suitt, Riverside, CA (US)

(73) Assignee: Globe Biomedical, Inc., Riverside, CA (US)

( * ) Notice: Subject to any disclaimer, the term of this patent is extended or adjusted under 35 U.S.C. 154(b) by 0 days.

(21) Appl. No.: 18/309,662

(22) Filed: Apr. 28, 2023

Related U.S. Application Data

(60) Provisional application No. 63/337,109, filed on May 1, 2022, provisional application No. 63/337,105, filed on May 1, 2022.

(51) Int. Cl.
*A61B 3/10* (2006.01)
*A61B 3/00* (2006.01)
*A61B 3/18* (2006.01)

(52) U.S. Cl.
CPC ............ *A61B 3/101* (2013.01); *A61B 3/0025* (2013.01); *A61B 3/18* (2013.01); *A61B 2560/0406* (2013.01); *A61B 2576/02* (2013.01)

(58) Field of Classification Search
CPC .... A61F 2009/00872; A61F 2009/0088; A61F 2009/00844; A61F 2009/0087; A61F 9/008; A61F 9/00804; A61F 9/00806; A61F 9/00827; A61B 3/0083; A61B 3/14; A61B 3/0025; A61B 3/135; A61B 3/107; A61B 3/152; A61B 3/0008; A61B 3/0041; A61B 5/0077; A61B 2562/166; A61B 3/0091; A61B 5/6898; A61B 3/1015; A61B 8/10; A61B 3/154; A61B 2034/107;

(Continued)

(56) References Cited

U.S. PATENT DOCUMENTS 5,812,240 A    9/1998   Teraoka et al.
6,019,472 A    2/2000   Koester et al.

(Continued)

FOREIGN PATENT DOCUMENTS

AU    2017366730    5/2019
AU    2020100831    10/2020

(Continued)

OTHER PUBLICATIONS

Babenko et al., "Detection of signs of disease in external photographs of the eyes via deep learning", Nature Biomedical Engineering, Sep. 21, 2021, in 24 pages.

(Continued)

*Primary Examiner* — Brandi N Thomas
(74) *Attorney, Agent, or Firm* — Knobbe, Martens, Olson & Bear, LLP

(57) ABSTRACT

A spectacles-mounted ophthalmic monitoring system may include a spectacles frame comprising a left rim and a right rim, an image sensor coupled with the spectacles frame to capture images of a field of view of an eye, and a processor. The processor may be configured to activate the image sensor to capture an image of the field of view, and identify a height of a tear film meniscus within the field of view of one or more images within the series of images.

25 Claims, 15 Drawing Sheets

(58) Field of Classification Search
CPC ..... A61B 3/0033; A61B 3/0285; A61B 3/036;
A61B 3/101; A61B 3/117; A61B 3/1208;
A61B 3/18; A61B 2562/0219; A61B
3/0058; A61B 3/113; A61B 3/12; A61B
3/145; A61B 3/15; A61B 3/16; A61B
5/0059; A61B 5/0068; A61B 5/0071;
A61B 5/0075; A61B 5/1114; A61B
5/14555; A61B 5/14558; A61B 5/4842
See application file for complete search history.

(56) References Cited

U.S. PATENT DOCUMENTS

| | | | |
|---|---|---|---|
| 6,110,110 | A | 8/2000 | Dublin, Jr. et al. |
| 6,997,556 | B2 | 2/2006 | Pfleger |
| 7,488,294 | B2 | 2/2009 | Torch |
| 7,515,054 | B2 | 4/2009 | Torch |
| 7,866,819 | B2 | 1/2011 | Tuan |
| 8,929,589 | B2 | 1/2015 | Publicover et al. |
| 9,041,787 | B2 | 5/2015 | Andersson et al. |
| 9,298,007 | B2 | 3/2016 | Border |
| 9,532,714 | B2 | 1/2017 | Border et al. |
| 9,532,715 | B2 | 1/2017 | Border et al. |
| 9,545,197 | B2 | 1/2017 | Korb et al. |
| 9,552,517 | B2 | 1/2017 | Chang et al. |
| 9,584,971 | B1 | 2/2017 | Guo et al. |
| 9,596,391 | B2 | 3/2017 | Henderek et al. |
| 9,706,912 | B2 | 7/2017 | Copland et al. |
| 9,710,058 | B2 | 7/2017 | Gustafsson et al. |
| 9,795,290 | B2 | 10/2017 | Grenon et al. |
| 9,832,412 | B2 | 11/2017 | Burkholz et al. |
| 9,836,122 | B2 | 12/2017 | Border |
| 9,952,664 | B2 | 4/2018 | Border et al. |
| 9,977,960 | B2 | 5/2018 | Gustafsson et al. |
| 10,016,130 | B2 | 7/2018 | Ganesan et al. |
| 10,045,737 | B2 | 8/2018 | Tzieli et al. |
| 10,188,791 | B2 | 1/2019 | Burkholz et al. |
| 10,277,787 | B2 | 4/2019 | Andersson et al. |
| 10,307,085 | B2 | 6/2019 | Sales et al. |
| 10,310,597 | B2 | 6/2019 | Biedert et al. |
| 10,334,212 | B2 | 6/2019 | Yin et al. |
| 10,368,743 | B2 | 8/2019 | Gerrans et al. |
| 10,467,470 | B2 | 11/2019 | Gustafsson et al. |
| 10,565,446 | B2 | 2/2020 | Gustafsson et al. |
| 10,607,075 | B2 | 3/2020 | Gustafsson et al. |
| 10,617,342 | B2 | 4/2020 | Sales et al. |
| 10,638,169 | B2 | 4/2020 | Su et al. |
| 10,686,972 | B2 | 6/2020 | Ronngren |
| 10,802,585 | B2 | 10/2020 | Agaoglu et al. |
| 10,806,341 | B2 | 10/2020 | Rickard et al. |
| 10,842,430 | B1 | 11/2020 | Novelli et al. |
| 10,887,548 | B2 | 1/2021 | Mayer et al. |
| 11,058,295 | B2 | 7/2021 | Okazaki et al. |
| 11,073,903 | B1 | 7/2021 | Ouderkirk et al. |
| 11,103,122 | B2 | 8/2021 | Border |
| 11,619,814 | B1 | 4/2023 | Newcombe et al. |
| 2002/0113943 | A1 | 8/2002 | Trajkovic et al. |
| 2005/0165321 | A1 | 7/2005 | Fischell et al. |
| 2007/0055222 | A1 | 3/2007 | Hohla et al. |
| 2009/0203985 | A1 | 8/2009 | Ehrecke |
| 2010/0286498 | A1 | 11/2010 | Dacquay et al. |
| 2011/0279666 | A1 | 11/2011 | Strombom et al. |
| 2012/0238857 | A1 | 9/2012 | Wong et al. |
| 2012/0293773 | A1 | 11/2012 | Publicover et al. |
| 2013/0030257 | A1 | 1/2013 | Nakata et al. |
| 2013/0041245 | A1 | 2/2013 | Cerboni |
| 2013/0128364 | A1 | 5/2013 | Wheeler |
| 2014/0055567 | A1 | 2/2014 | Dyer |
| 2014/0055746 | A1 | 2/2014 | Nistico et al. |
| 2014/0228668 | A1 | 8/2014 | Wakizaka et al. |
| 2015/0206008 | A1 | 7/2015 | Border et al. |
| 2018/0235465 | A1 | 8/2018 | Calpe et al. |
| 2019/0167095 | A1 | 6/2019 | Krueger |
| 2020/0359886 | A1 | 11/2020 | Azar et al. |
| 2021/0000341 | A1 | 1/2021 | Kuperman |
| 2021/0186318 | A1 | 6/2021 | Yellin et al. |
| 2021/0247617 | A1 | 8/2021 | Kassner et al. |
| 2021/0282669 | A1 | 9/2021 | Borden et al. |
| 2021/0318558 | A1 | 9/2021 | Tzvieli et al. |
| 2022/0139179 | A1 | 5/2022 | Park et al. |
| 2022/0155860 | A1 | 5/2022 | Tzvieli et al. |
| 2022/0236796 | A1 | 7/2022 | Konrad et al. |
| 2022/0313077 | A1 | 10/2022 | Singh et al. |

FOREIGN PATENT DOCUMENTS

| | | | |
|---|---|---|---|
| CA | 2824921 | 6/2019 | |
| CN | 206381163 | 8/2017 | |
| CN | 108919517 | 11/2018 | |
| CN | 111714341 | 9/2020 | |
| CN | 110262074 | 3/2021 | |
| CN | 113589554 | 11/2021 | |
| CN | 113749610 | * 12/2021 | ............... A61B 3/14 |
| EP | 1241976 | 6/2008 | |
| EP | 3514606 | 7/2019 | |
| JP | 2008-104628 | 5/2008 | |
| JP | 5301815 | 9/2013 | |
| JP | 5642945 | 12/2014 | |
| JP | 2017-211891 | 11/2017 | |
| JP | 6396351 | 9/2018 | |
| JP | 6535223 | 6/2019 | |
| JP | 2020-517012 | 6/2020 | |
| WO | WO 2012/129405 | 9/2012 | |
| WO | WO 2018/202929 | 11/2018 | |
| WO | WO 2020/214420 | 10/2020 | |
| WO | WO 2021/132978 | 7/2021 | |
| WO | WO 2022/094446 | 5/2022 | |

OTHER PUBLICATIONS

Babenko et al., "Discovering novel systemic biomarkers in photos of the external eye", Jul. 2022, in 49 pages.
Gulshan et al., "Development and Validation of a Deep Learning Algorithm for Detection of Diabetic Retinopathy in Retinal Fundus Photographs", JAMA, Dec. 13, 2016, vol. 316, No. 22, pp. 2402-2410.
Nelson, "Hyperlipidemia as a Risk Factor for Cardiovascular Disease", Prim Care., Mar. 2013, vol. 40, No. 1, pp. 195-211.

* cited by examiner

TEAR MENISCUS DETECTION AND EVALUATION SYSTEM

CROSS REFERENCE TO RELATED APPLICATIONS

All applications for which a foreign or domestic priority claim is identified in the Application Data Sheet as filed with the present application are hereby incorporated by reference and made part of this specification.

TECHNICAL FIELD

The present disclosure relates generally to systems and methods for processing and analyzing ocular health data from wearable devices, and more particularly, to systems and methods for processing and using data from sensing devices to monitor, assess, or predict ophthalmic features and conditions.

BACKGROUND

Long-standing approaches to monitoring eye health employ sporadic office-based inspection of the eye. The state of an individual's eye health and vision is checked in ophthalmologist or optometrist office visits, which may occur yearly, but for many individuals occur less frequently. For less regular patients, optometrist office visits may only be scheduled when the patient notices a degradation in vision. However, many eye conditions develop slowly in an imperceptible manner. Preventable damage to eye structures can occur before the patient notices changes or vision loss.

SUMMARY OF SOME EMBODIMENTS

In some aspects, the techniques described herein relate to an ophthalmic monitoring system including: an eyeglasses frame including a left rim and a right rim, at least of one of the left rim and the right rim including a sensor enclosure oriented toward an eye of a wearer when the eyeglasses frame is worn; an image sensor disposed in the sensor enclosure to capture images of an eye from within the sensor enclosure; an environmental sensor disposed on the eyeglasses frame and configured to detect a first environmental signal corresponding to a first state in which the eyeglasses frame is being worn and a second environmental signal corresponding to a second state in which the eyeglasses frame has been removed from a head of the wearer; and a processor configured to: (a) activate the environmental sensor; (b) detect the first environmental signal corresponding to the first state; (c) detect the second environmental signal corresponding to the second state; (d) activate the image sensor to capture a plurality of images of the eye; (e) tag a first image of the plurality of images captured by the image sensor, the first image being captured at a first time when the first environmental signal is detected and before the detection of the second environmental signal indicating that the eyeglasses frame has been removed from the head of the wearer; and (f) tag a second image of the plurality of images captured by the image sensor, the second image being captured at a second time after the second environmental signal has been detected and after the first environmental signal is once again detected after the second environmental signal is detected.

In some aspects, the techniques described herein relate to an ophthalmic monitoring system including: an eyeglasses frame including a left rim and a right rim, at least one of one of the left rim and the right rim including a sensor enclosure oriented toward an eye of a wearer when the eyeglasses frame is worn; an image sensor disposed in the sensor enclosure to capture images of an eye from within the sensor enclosure; and a processor configured to: (a) activate the image sensor to capture a plurality of images of the eye; (b) detect a first state in which the eyeglasses frame is being worn; (c) detect a second state in which the eyeglasses frame has been removed from a head of the wearer; (d) tag a first image of the plurality of images captured by the image sensor, the first image being captured at a first time when the first state is detected and before the detection of the second state indicating that the eyeglasses frame has been removed from the head of the wearer; and (f) tag a second image of the plurality of images captured by the image sensor, the second image being captured at a second time after the second state has been detected and after the first state is once again detected after the second state is detected.

In some aspects, the techniques described herein relate to a spectacles-mounted ophthalmic monitoring system, including: a spectacles frame including a left rim and a right rim; an image sensor coupled with the spectacles frame to capture images of a field of view of an eye disposed around at least a portion of a lower eyelid, a portion of an upper eyelid, and a portion of a sclera; and a processor configured to: (a) activate the image sensor to capture a series of images of the field of view; (b) identify a height of a tear film meniscus within the field of view of one or more images within the series of images; (c) identify a reflection of a light-emitting screen in the field of view of one or more images within the series of images; and (d) identify a blink rate of one or more images within the series of images; and (e) determine an eye strain metric based on a combination of two or more of the height of the tear film meniscus identified in (a), the reflection of the light-emitting screen identified in (b), and the blink rate identified in (c).

In some aspects, the techniques described herein relate to a spectacles-mounted ophthalmic monitoring system including: a spectacles frame including a left rim and a right rim; an image sensor coupled with the spectacles frame to capture images of a field of view of an eye disposed around at least a portion of a lower eyelid, a portion of an upper eyelid, and a portion of a sclera; and a processor configured to: activate the image sensor to capture an image of the field of view; segment the image into an eye portion and a background portion; identify, within the eye portion, a location of a lower eyelid; identify, within the eye portion, an upper edge of a tear film meniscus; and determine a height of the tear film meniscus based on the location of the lower eyelid and a location of the upper edge of the tear film meniscus.

In some aspects, the techniques described herein relate to a computer-implemented method of monitoring an eye from a pair of spectacles including: under control of a computer system including one or more processors configured to execute specific computer-executable instructions, (a) activating an environmental sensor disposed on an eyeglasses frame; (b) detecting an environmental signal corresponding to a first state in which the eyeglasses frame is being worn by a wearer; (c) detecting an environmental signal corresponding to a second state in which the eyeglasses frame has been removed from a head of the wearer; (d) detecting an environmental signal corresponding to a second state in which the eyeglasses frame has been removed from a head of the wearer; (e) activating an image sensor to capture a plurality of images of an eye of the wearer; (f) tagging a first image of the plurality of images captured by the image sensor before step (c); (f) tagging a second image of the plurality of images captured by the image sensor after step (d); and (g) outputting the first image and the second image to a processor to conduct an analysis of a tear film meniscus in one or both of the first image and the second image.

In some aspects, the techniques described herein relate to a spectacles-a right rim; an image sensor coupled with the spectacles frame to capture images of a field of view of an eye; and a processor configured to: activate the image sensor to capture a first image of the field of view at a first time; activate the image sensor to capture a second image of the field of view at a second time subsequent to the first time; identify an ophthalmic feature associated with the eye based on at least one of the first image or the second image; and generate an output based on the ophthalmic feature.

In some aspects, the techniques described herein relate to a computer-implemented method including: under control of a processor of a spectacles-mounted ophthalmic monitoring system including a spectacles frame and an image sensor coupled with the spectacles frame to capture images of a field of view of an eye, activating the image sensor to capture a first image of the field of view at a first time; activating the image sensor to capture a second image of the field of view at a second time subsequent to the first time; identifying an ophthalmic feature associated with the eye based on at least one of the first image or the second image; and generating an output based on the ophthalmic feature.

In some aspects, the techniques described herein relate to a system for machine learning training for detection of ophthalmic features, the system including: a spectacles frame including an image sensor, wherein the spectacles frame is configured to capture images of an eye of a wearer; an image data store storing a plurality of images generated using the image sensor; and a computing device including one or more processors and computer-readable memory, the computing device programmed by executable instructions to at least: generate a plurality of training data images using the plurality of images, wherein images in a first subset of the plurality of training data images are associated with label data representing a positive classification for presence of an ophthalmic feature, and wherein images in a second subset of the plurality of training data images are associated with label data representing a negative classification for presence of the ophthalmic feature; train a machine learning model using the plurality of training data images, wherein the machine learning model is trained to generate output data representing classification of at least a portion of an input image as one of negative or positive for presence of the ophthalmic feature; and distribute the machine learning model to one or more spectacles-mounted ophthalmic monitoring systems.

In some aspects, the techniques described herein relate to a spectacles-a right rim; an image sensor coupled with the spectacles frame to capture images of a field of view of an eye; and a processor configured to: determine that the image sensor is to operate in a first resolution mode of a plurality of resolution modes; activate the image sensor to capture a first image using the first resolution mode at a first time; determine, subsequent to the image sensor capturing the first image, that the image sensor is to operate in a second resolution mode of the plurality of resolution modes; and activate the image sensor to capture a second image in the second resolution mode at a second time.

In some aspects, the techniques described herein relate to a spectacles-mounted ophthalmic monitoring system including: a spectacles frame including a left rim and a right rim; an image sensor coupled with the spectacles frame to capture images of a field of view of an eye; and a processor configured to: activate the image sensor to capture a first image at a first time; determine a duration of time to wait before capturing a second image; and activate the image sensor to capture a second image a second time, wherein a difference between the first time and the second time corresponds to the duration of time to wait.

In some aspects, the techniques described herein relate to a spectacles-mounted ophthalmic monitoring system including: a spectacles frame including a left rim and a right rim; an image sensor coupled with the spectacles frame to capture images of a field of view of an eye; and a processor configured to: activate the image sensor to capture a first image of the field of view at a first time; activate the image sensor to capture a second image of the field of view at a second time subsequent to the first time; identify an eyelid blink based on at least one of the first image or the second image; and generate an output based on identification of the eyelid blink.

In some aspects, the techniques described herein relate to a spectacles-mounted ophthalmic monitoring system including: a spectacles frame including a left rim and a right rim; an image sensor coupled with the spectacles frame to capture images of a field of view of an eye; and a processor configured to: activate the image sensor to capture an image of the field of view; identify a light-emitting screen reflection in the eye based on the image; and generate an output based on identification of the light-emitting screen reflection.

In some aspects, the techniques described herein relate to a spectacles-a right rim; an image sensor coupled with the spectacles frame to capture images of a field of view of an eye; and a processor configured to: activate the image sensor to capture an image of the field of view; identify an eyepatch-based ophthalmic feature based on the image; and generate an output based on identification of the eyepatch-based ophthalmic feature.

In some aspects, the techniques described herein relate to a spectacles-mounted ophthalmic monitoring system including: a spectacles frame including a left rim and a right rim; an image sensor coupled with the spectacles frame to capture images of a field of view of an eye; and a processor configured to: activate the image sensor to capture an image of the field of view; determine a tear meniscus height based on the image; and generate an output based on identification of the tear meniscus height.

In some aspects, the techniques described herein relate to a spectacles-mounted ophthalmic monitoring system including: a spectacles frame including a left rim and a right rim; an image sensor coupled with the spectacles frame to capture images of a field of view of an eye; and a processor configured to: activate the image sensor to capture an image of the field of view; determine an eye strain metric based on the image; and generate an output based on the eye strain metric.

In some aspects, the techniques described herein relate to a spectacles-mounted ophthalmic monitoring system including: a spectacles frame including a left rim and a right rim; an image sensor coupled with the spectacles frame to capture images of a field of view of an eye; and a processor configured to: activate the image sensor to capture a plurality of images of the field of view; determine that the spectacles frame is coupled to an external charging source; and send the plurality of images to remote computing system.

In some aspects, the techniques described herein relate to a computer-implemented method including, under control of a computing system comprising a processor configured to execute specific instructions: receiving, from a spectacles-mounted ophthalmic monitoring system including a spectacles frame and an image sensor coupled with the spectacles frame to capture images of a field of view of an eye, a first image of the field of view at a first time and a second image of the field of view at a second time subsequent to the first time; identifying an ophthalmic feature associated with the eye based on at least one of the first image or the second image; and generating an output based on the ophthalmic feature.

In some aspects, the techniques described herein relate to a computer-implemented method including, under control of a computing system comprising a processor configured to execute specific instructions: receiving a first image of a field of view of an eye generated by an image sensor of a spectacles assembly at a first time; receiving a second image of the field of view of the eye generated by the image sensor of the spectacles assembly at a second time subsequent to the first time; identifying an eyelid blink based on at least one of the first image or the second image; and generating an output based on identification of the eyelid blink.

In some aspects, the techniques described herein relate to a computer-implemented method including, under control of a computing system comprising a processor configured to execute specific instructions: receiving an image of a field of view of an eye generated by an image sensor of a spectacles assembly; identifying a light-emitting screen reflection in the eye based on the image; and generating an output based on identification of the light-emitting screen reflection.

In some aspects, the techniques described herein relate to a computer-implemented method including, under control of a computing system comprising a processor configured to execute specific instructions: receiving an image of a field of view of an eye generated by an image sensor of a spectacles assembly; identifying an eyepatch-based ophthalmic feature based on the image; and generating an output based on identification of the eyepatch-based ophthalmic feature.

In some aspects, the techniques described herein relate to a computer-implemented method including, under control of a computing system comprising a processor configured to execute specific instructions: receiving an image of a field of view of an eye generated by an image sensor of a spectacles assembly; determining a tear meniscus height based on the image; and generating an output based on identification of the tear meniscus height.

In some aspects, the techniques described herein relate to a computer-implemented method including, under control of a computing system comprising a processor configured to execute specific instructions: receiving an image of a field of view of an eye generated by an image sensor of a spectacles assembly; determining an eye strain metric based on the image; and generating an output based on the eye strain metric.

BRIEF DESCRIPTION OF THE DRAWINGS

Embodiments of various inventive features will now be described with reference to the following drawings. Throughout the drawings, reference numbers may be re-used to indicate correspondence between referenced elements. The drawings are provided to illustrate example embodiments described herein and are not intended to limit the scope of the disclosure.

DETAILED DESCRIPTION

Figure 1:
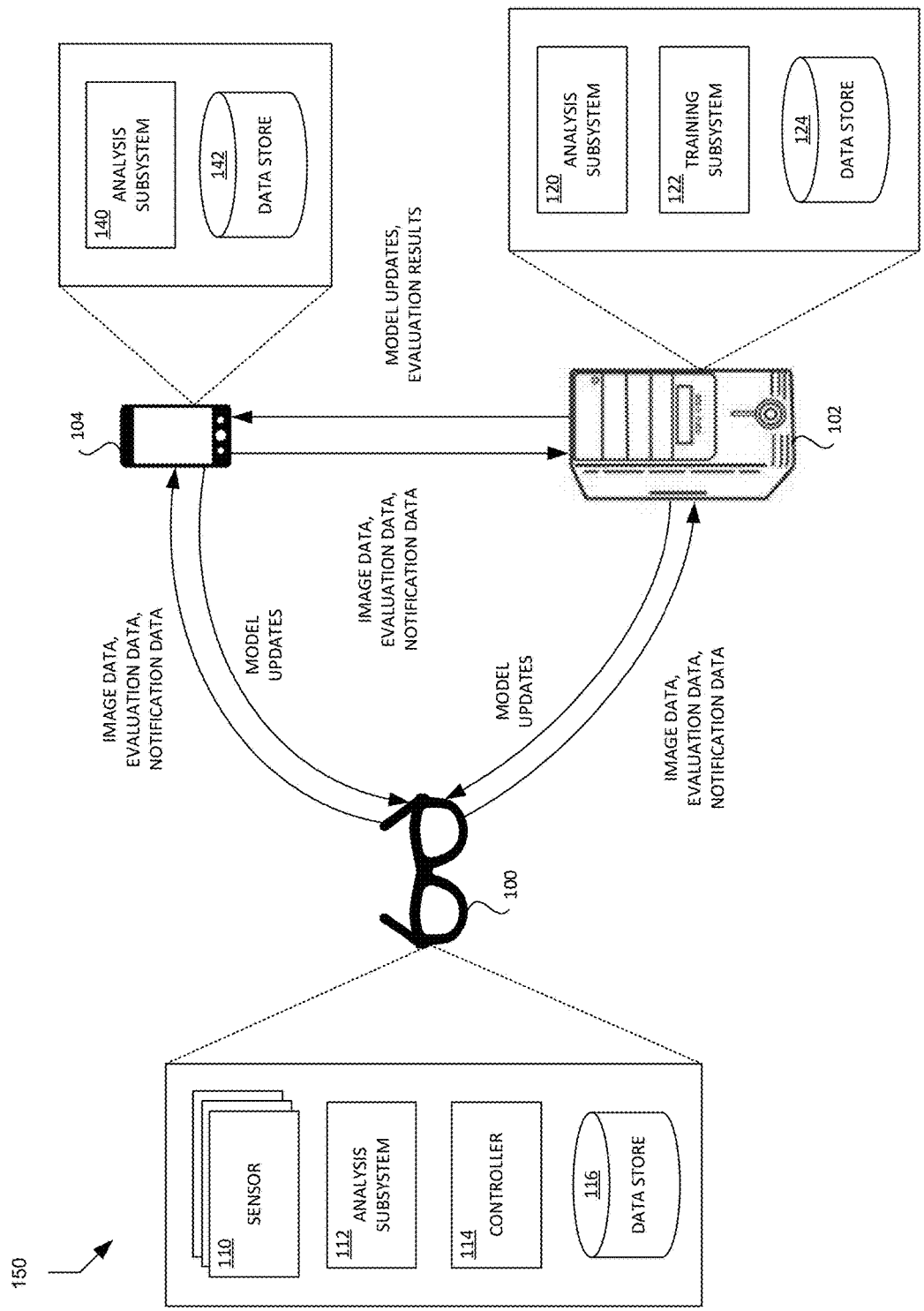
FIG. 1 illustrates example data flows and interactions between various devices of an ophthalmic monitoring system according to some embodiments.

The present disclosure relates generally to the use of wearable devices to generate data regarding ocular health and conditions of wearers, and to the evaluation of the data. More specifically, aspects of the present disclosure relate to an ophthalmic monitoring system that includes a wearable spectacles assembly with one or more sensors for generating data regarding a wearer. The data may be used—by the spectacles assembly or by a separate computing device of the ophthalmic monitoring system—to monitor, assess, or predict ophthalmic features or conditions of the wearer.

Current modes of monitoring eye health lack sufficient data collection and analysis to equip patients and health care providers (HCPs) to act in a timely manner. For example, patients with progressive eye conditions such as glaucoma may be professionally examined multiple times per year. However, this cadence of examinations—even if closely adhered to—leaves the condition of the patient unknown for long periods of time. While scheduling more frequent patient visits could reduce these data deficiencies, that approach would greatly increase the patient monitoring cost.

The inconvenience of frequent office visits can also lead to poor patient compliance. Moreover, office visits—however frequent—are not useful in evaluating the condition of a patient during normal, everyday activities, or in evaluating how the patient's condition changes in response to certain activities and environmental factors that typically or only occur outside the HCP office setting. Instead, HCPs rely on subjective descriptions provided by patients who may not accurately convey the information necessary to evaluate, diagnose, and/or treat a condition.

To address issues with reliance on in-office visits in assessing ocular health and tracking conditions, an ophthalmic monitoring system may be implemented. The ophthalmic monitoring system may include a wearable spectacles assembly with sensors and processing components embedded within or coupled thereto. Thus, the ophthalmic monitoring system may be referred to as a spectacles-mounted ophthalmic monitoring system. As a patient-worn device, the spectacles assembly can provide ocular health monitoring and data generation outside of the HCP office setting, and can provide objective insights into the ocular health of the patient during normal everyday activities, periods of inactivity, etc. For example, the spectacles assembly may include one or more image sensors to capture images of a patient's eye(s), one or more environmental sensors to generate environmental signals of non-image data (e.g., motion, temperature, ambient light, infrared light, etc.) that may be useful in evaluating a patient's ocular health, a processor to analyze image data and non-image data and generate output regarding the patient's ocular health or conditions, data storage to store image data and non-image data for future evaluation, a communication interface to send the data to a separate remote computing system of the ophthalmic monitoring system, other components, or any combination thereof. However, the wearable nature and small form factor of such a spectacles assembly can present challenges in terms of data storage capacity, power usage, processing capabilities, and the like. Moreover, the substantially continuous availability of image data and non-image data about patients—through everyday activities or periods of inactivity, and over the course of days, weeks, months, etc.—provides additional opportunities to monitor and assess new ophthalmic features, or to monitor and assess ophthalmic features in a new way. This availability provided by the spectacles assembly and ophthalmic monitoring system can give both HCPs and patients the ability to improve ocular health assessment, implement interventions, and the like.

Some aspects of the present disclosure address some or all of the challenges and opportunities noted above by managing the operation of a spectacles assembly to improve utilization of data storage capacity and battery capacity. For example, in order to extend battery life for the spectacles assembly, dynamic power consumption algorithms may be used to collect ocular surface imagery or sensor data in a strategic way. This can provide a balance between energy use, computational load, and high-quality data collection.

In some embodiments, a spectacles assembly may include an image sensor configured to capture images at different degrees of quality, such as at different resolutions. Although higher resolution images may capture more fine detail for evaluation, higher resolution images also consume more storage space than lower resolution images. To increase the quantity of images that may be stored in the limited storage space available onboard the spectacles assembly while also providing for the opportunity to capture high resolution images, the spectacles assembly may determine and use image capture parameters such as timing and resolution settings to control the capture of images. For example, images may be captured according to a predetermined or dynamically-determined schedule, and the period of time between image capture operations may be set based on factors such as available storage space, environmental factors (e.g., ambient lighting conditions, time of day, or other factors that may impact image quality), activity level, or the like. As another example, images of one resolution (e.g., lower resolution images) may be captured and analyzed to determine whether to capture images of a different resolution (e.g., whether to use additional storage space for higher resolution images). The determination may be based on image-capture factors identified within lower-resolution images, such as the presence an eye of the wearer (e.g., to avoid taking high resolution images when the spectacles assembly is not worn or otherwise not positioned for a view of the eye), the presence of a clear, well-lit environment for capture of a higher resolution image, or the like.

In some embodiments, evaluation and storage of images onboard the spectacles assembly may be managed to reduce the time and complexity of processing and storage operations, thereby conserving battery power. For example, evaluation of images by a processor onboard the spectacles assembly may involve evaluation of raw image data (e.g., image data received from an image sensor with little or none of the additional processing typically performed to prepare an image for display). In this way, the processing burden and battery power required by the onboard processor may be reduced in comparison with conventional image capture, storage, and evaluation processes. As another example, the amount of computing resource overhead (processor cycles, battery usage, etc.) used in a data storage operation to commit data to persistent storage may be significant and may not necessarily increase linearly with the amount of data being stored. Therefore, to reduce the number of storage operations that are performed, the spectacles assembly may buffer images for storage and only commit the images to persistent storage after a threshold quality of images, amount of storage space, or period of time has passed. When the images are committed to persistent storage, they may be committed in a single storage operation as a single storage object (e.g., as a "virtual stack") comprising multiple images, rather than as a separate storage object for each image. In this way, the computing resources required to store the images may be reduced in comparison with conventional image capture and storage processes.

Additional aspects of the present disclosure relate to leveraging the availability of periodic or substantially continuous data generated by a spectacles assembly to monitor, assess, or predict ophthalmic features or conditions. The availability of data generated by the spectacles assembly can permit detection and evaluation of ophthalmic features in a wearer's typical daily experience. The availability of data generated by the spectacles assembly can also or alternatively permit detection and evaluation of atypically-occurring ophthalmic features. In either case, the availability of the data and methods of evaluating the data can provide objective insights into the ophthalmic features and ocular health of patients outside the HCP office setting, and can provide insights not previously available even in an HCP office setting. Moreover, the availability of data and detection capabilities provided by the spectacles assembly (and the ophthalmic monitoring system as a whole) can allow for detection of ophthalmic features and triggering of notifications to patients, HCPs, and other parties in real-time or otherwise significantly more quickly than would be available in the typical cadence of HCP office visits.

As used herein, the term "ophthalmic feature" refers to a characteristic or an event related to a wearer's eye. For example, an ophthalmic feature may be or include: occurrence of a full or partial eyelid blink; strength or velocity of a blink; blink rate; partial blink rate; reflection of a light-emitting screen in the wearer's eye; type of light-emitting screen being viewed by the wearer; duration of time the wearer views a screen (also referred to as "screen time duration," or more simply as "screen time" for brevity); distance from a light-emitting screen; duration of time the wearer views any near-field object; distance between the wearer's pupils (also referred to as "interpupillary distance"); scleral area of an eye; height of the tear film (also referred to as "tear meniscus") on a wearer's eye; a change in tear film height; removal or replacement of the spectacles assembly; application of an eyedrop; presence of an eyepatch over the wearer's eye; duration of time an eyepatch is worn; other features; or any combination thereof or derivation therefrom. The example ophthalmic features described herein are provided for purposes of illustration only, and are not intended to be limiting, required, or exhaustive. In some embodiments, additional, fewer, and/or alternative ophthalmic features may be detected, evaluated, or used in other processing operations.

In some embodiments, data generated by one or more sensors of the spectacles assembly may be evaluated to determine blink-based ophthalmic features. Images or environmental data (e.g., data generated by infrared transmitters and receivers) can be evaluated using one or more methods to determine the blink-based ophthalmic features. For example, images may be processed using image segmentation, pixel-based analysis, detection of MRD1 scores or MRD2 scores, variations in hue, saturation, and value (HSV) color space data, or other image processing methods to detect the location of an eyelid. Changes in the location of the eyelid over the course of multiple images can be identified and used to determine whether the wearer has blinked, whether a blink was a partial or full blink, the velocity of the blink, or other blink-based ophthalmic features. As another example, infrared light may be emitted, reflected off of the eye and eyelid, and sensed by an infrared receiver. Differences in the way infrared light is reflected by the surface of the eye when the eye is open compared with the eyelid when the eye is closed can be identified to detect a blink. As a further example, images or environmental data may be evaluated using a machine learning model trained to classify input data as representative of a blink or other blink-based ophthalmic feature.

In some embodiments, data generated by one or more sensors of the spectacles assembly may be evaluated to determine screen-based ophthalmic features. The viewing of near-field objects—including books, light-emitting screens, and the like—for extended durations of time is associated with development of myopia (nearsightedness). In contrast, time spent outdoors can be associated with a decreased risk of myopia. To detect a patient at risk for developing myopia or to prevent development of myopia, the ophthalmic monitoring system may monitor the wearer's screen time or time spent viewing near-field objects generally, or time spent outdoors. For example, images may be processed using image segmentation, pixel-based analysis, edge detection, variations in color data, or other image processing methods to detect a reflection of a light-emitting screen on a wearer's eye. The duration of time such a reflection is present can be identified and used to determine the wearer's screen time. As another example, the motion of the user's head (or lack thereof), as represented by motion data from motion signals generated by inertial sensors in the spectacles assembly, can be used to determine the type of screen the wearer is viewing (e.g., viewing of near-field screens tends to be associated with different motion profiles than viewing of more distant screens). As a further example, the wearer's interpupillary distance can be used to determine the distance of the light-emitting screen or other object being viewed (e.g., viewing of near-field objects tends to be associated with smaller interpupillary distances than viewing of more distant objects). As another example, the degree of brightness of ambient light, the amount and nature of head motion, the interpupillary distance, or some combination thereof may be used to determine the wearer's time spent outdoors. As a further example, images or environmental data may be evaluated using a machine learning model trained to classify input data as representative of presence of a light-emitting screen reflection, viewing of a near-field object, time spent outdoors, or another screen-based ophthalmic feature.

In some embodiments, data generated by one or more sensors of the spectacles assembly may be evaluated to determine eyepatch-based ophthalmic features. A wearer may be prescribed eyepatch therapy to treat eye conditions such as amblyopia (lazy eye). Eyepatch detection may be performed to determine wearer compliance with an eyepatch therapy prescription. For example, images may be processed using image segmentation, pixel-based analysis, edge detection, variations in color data, or other image processing methods to detect the presence of a therapeutic eyepatch on a wearer's eye. The duration of time such an eyepatch is present can be identified and used to determine the wearer's eyepatch time. The eyepatch may be detected based on a distinctive design element that is easy to distinguish from the wearer's eye, whether open or closed. As another example, images may be evaluated using a machine learning model trained to classify input data as representative of presence of an eyepatch.

In some embodiments, data generated by one or more sensors of the spectacles assembly may be evaluated to determine eyedrop-based ophthalmic features. For example, images or environmental data may be evaluated to determine whether a wearer has removed or replaced the spectacles assembly. After detecting replacement of the spectacles assembly, one or more images may be processed using image segmentation, pixel-based analysis, edge detection, variations in color data, or other image processing methods to detect the height of the tear film on the eye. The height may be compared to prior or subsequent tear film heights to determine whether the wearer has applied an eyedrop (e.g., due to a higher tear film after replacement of the spectacles assembly), to determine the rate or degree to which the tear film decreases after application of an eyedrop, or to determine other ophthalmic features.

Further aspects of the present disclosure provide evaluation of particular characteristics of eyes, activities, and the like to facilitate detection, assessment, or prediction of ophthalmic features. In some embodiments, sensor data representing eyes, activities, and the like of multiple patients (e.g., dozens, hundreds, thousands, or more) may be obtained and labeled as being representative of particular ophthalmic features. For example, images or other sensor data may be tagged with label data representing a positive classification or negative classification for blinking, positive classification or negative classification for viewing light-emitting screens, positive classification or negative classification for wearing eyepatches, metric values representing a height of a tear film meniscus, and the like. In some embodiments, augmentation data such as environmental sensor data (e.g., motion data, infrared data), non-sensor-based patient data (e.g., ocular health history information), or the like may be included with image data and tagged with label data accordingly. The labeled data may be used to train a machine learning model to classify or otherwise predict the likelihood that a wearer has exhibited or experience, or will exhibit or experience, a particular ophthalmic feature. The trained model may be deployed to one or more devices to evaluate new sensor data (e.g., sensor data not used to train the model). For example, a wearable spectacles assembly may have an embedded processing unit that uses the trained model to evaluate sensor data (e.g., image data, non-image data, and the) to detect ophthalmic features. An HCP may wish to remotely monitor the wearer outside of the HCP office setting to detect, assess, or predict certain ophthalmic features such as blink rate, screen time, eyepatch compliance, eye strain, etc. Output from the spectacles assembly applying the trained model to new sensor data may be provided to the HCP (e.g., in real time, on demand, or according to a schedule). As another example, sensor data from the spectacles assembly may be provided to a separate computing system such as a user's device, HCP's device, or a remote computing system such as a cloud-based system. The separate computing system may evaluate the sensor data using the trained model to detect, assess, or predict certain ophthalmic features.

Various aspects of the disclosure will now be described with regard to certain examples and embodiments, which are intended to illustrate but not limit the disclosure. Although aspects of some embodiments described in the disclosure will focus, for the purpose of illustration, on particular examples of spectacles assemblies, sensors, sensor data, machine learning models, and ophthalmic features, the examples are illustrative only and are not intended to be limiting, required, or exhaustive. In some embodiments, the techniques described herein may be applied to additional or alternative spectacles assemblies, sensors, sensor data, machine learning models, ophthalmic features, and the like. In addition, any feature, process, device, or component of any embodiment described and/or illustrated in this specification can be used by itself, or with or instead of any other feature, process, device, or component of any other embodiment described and/or illustrated in this specification.

Example Execution Environment

FIG. 1 illustrates interactions and data flows between various systems and devices of an ophthalmic monitoring system 150. In some embodiments, as shown, the ophthalmic monitoring system 150 may include: a spectacles assembly 100 configured to generate and evaluate sensor data regarding a wearer; a computing system 102 to evaluate data received from the spectacles assembly 100, and to update models or other evaluation components; a user device 104 to evaluate data received from the spectacles assembly 100, and to present notifications; other device; or a subset thereof. The systems and devices of the ophthalmic monitoring system 150 are illustrative only, and are not intended to be limiting, required, or exhaustive. In some embodiments, additional, fewer, and/or alternative systems or devices may be used. For example, in some embodiments multiple spectacles assemblies 100 may communicate with a single computing system 102 or user device 104. As another example, multiple user devices 104 (e.g., a wearer's device and an HCP's device) may communicate with a single spectacles assembly 100 or computing system 102.

Figure 2:
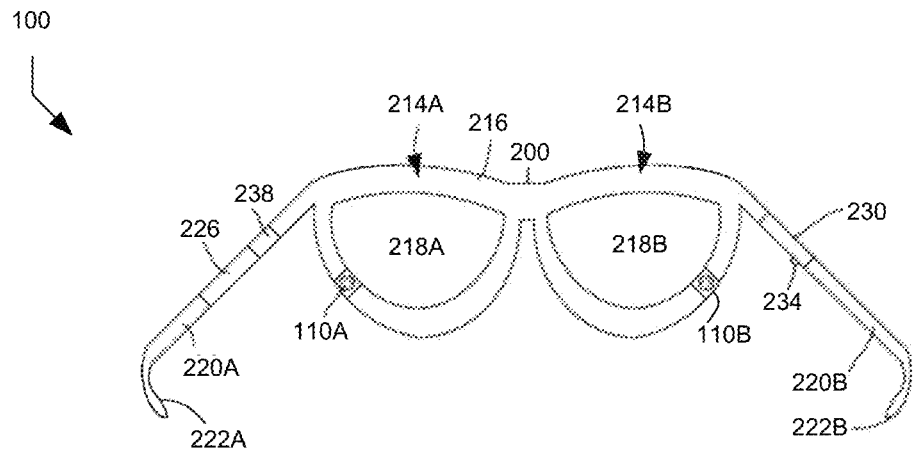
FIG. 2 illustrates an example wearable spectacles assembly according to some embodiments.
Figure 3:
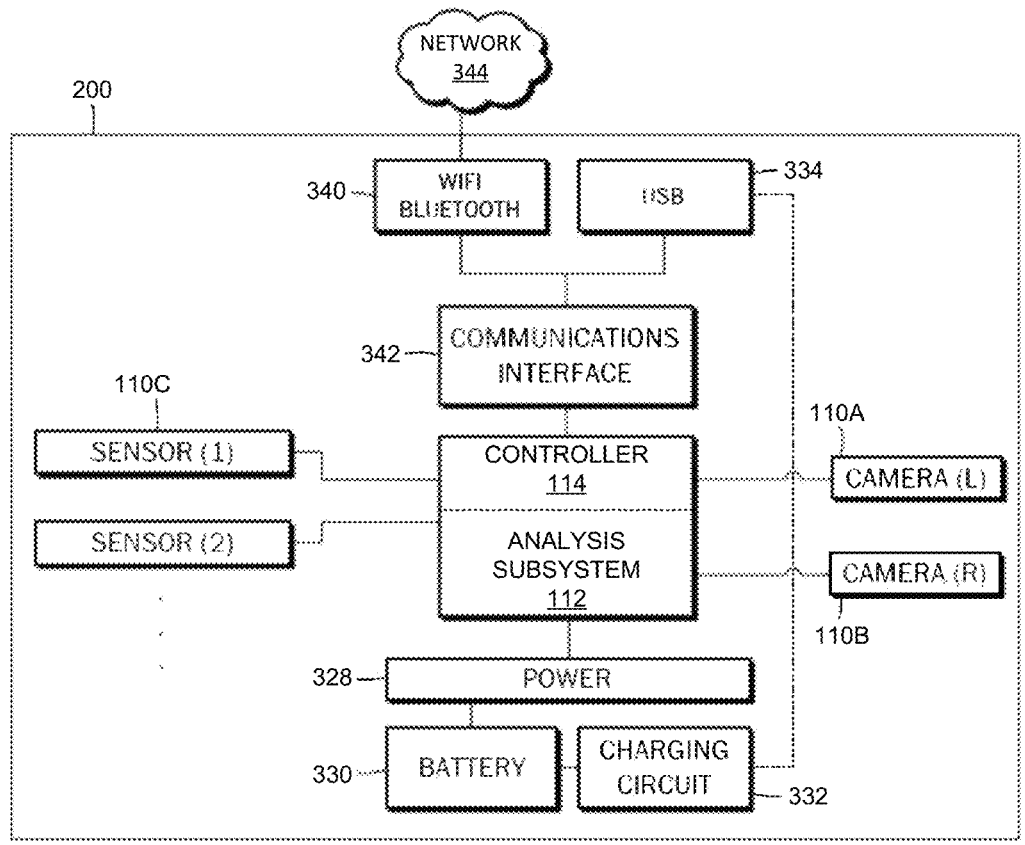
FIG. 3 is a block diagram illustrating various components of a wearable spectacles assembly according to some embodiments.

The spectacles assembly 100 may include any eyeglass frames to which sensors, processors, and other components may be integrated or coupled. In some embodiments, the spectacles assembly 100 may include: one or more sensors 110 to generate sensor data (e.g., image data or non-image data) about a wearer; an analysis subsystem 112 to analyze the sensor data; a controller 114 to control the operation of the sensor(s) 110, analysis subsystem 112, or other components; a data store 116 to store sensor data generated by the sensor(s) 110 or output of the analysis subsystem 112; other components; or any combination thereof. These components, or subsets thereof, may be implemented using various hardware. An example of a spectacles assembly and hardware components thereof is shown in FIGS. 2 and 3, and described in greater detail below. The spectacles assembly 100 may or may not include prescription lenses, tinted lenses, non-prescription lenses, glass panes, polymer panes, or no lenses at all.

Example implementations of a spectacles assembly that may be used in some embodiments are disclosed in U.S. Provisional Patent Application No. 63/495,052, filed Apr. 7, 2023 and titled "MECHANICAL INTEGRATION OF COMPONENTS OF WEARABLE DEVICES AND OCULAR HEALTH MONITORING SYSTEM," which is incorporated by reference herein and made part of this specification.

The computing system 102 may be or include any of a variety of computing devices, such as laptop computing device, desktop computing device, server computing device, or the like. In some embodiments, the computing system 102 may include: an analysis subsystem 120 to analyze sensor data or other data received from the spectacles assembly 100; a training subsystem 122 to train one or more models used to evaluate sensor data or other data received from the spectacles assembly 100; a data store 124 to store data generated by the analysis subsystem 120 or data received from the spectacles assembly 100; other components; or any combination thereof.

In some embodiments, the computing system 102 may include: one or more computer processors, such as physical central processing units (CPUs); one or more communication interfaces, such as network interface cards (NICs); an input/output interface configured to control a display and user controls; and one or more computer-readable memories, such as random-access memory (RAM), flash memory, and/or other non-transitory computer-readable media. The computer-readable memory may include specific instructions (e.g., computer program instructions) that one or more computer processors execute in order to implement one or more embodiments. For example, the computer-readable memory can store: an operating system that provides computer program instructions for use by the computer processor(s) in the general administration and operation of the computing system 102; analysis subsystem instructions for implementing the analysis subsystem 120; and training subsystem instructions for implementing the training subsystem 122. As another example, the computer-readable memory may include a data store 124.

The user device 104 may be or include any of a variety of computing devices, such as a mobile computing device (e.g., a smart phone or tablet), laptop computing device, desktop computing device, or the like. In some embodiments, the user device 104 may include: an analysis subsystem 140 to analyze sensor data or other data received from the spectacles assembly 100; a data store 142 to store data generated by the analysis subsystem 140 or data received from the spectacles assembly 100; other components; or any combination thereof.

In some embodiments, the user device 104 may include: one or more computer processors, such as CPUs; one or more communication interfaces, such as NICs; an input/output interface configured to control a display and user controls; and one or more computer-readable memories, such as RAM, flash memory, and/or other non-transitory computer-readable media. The computer-readable memory may include specific instructions (e.g., computer program instructions) that one or more computer processors execute in order to implement one or more embodiments. For example, the computer-readable memory can store: an operating system that provides computer program instructions for use by the computer processor(s) in the general administration and operation of the user device 104; analysis subsystem instructions for implementing the analysis subsystem 140; etc. As another example, the computer-readable memory may include a data store 142.

Referring now to FIG. 2, one exemplary embodiment of a spectacles assembly 100 is shown. The spectacles assembly 100 may include an eyeglasses frame 200 (also referred to as a spectacles frame) defined by a left rim 214A and a right rim 214B, which are joined together by a bridge 216. The left rim 214A and the right rim 214B each have respective anterior segments having an anterior lens mounting edge and respective posterior segments having a posterior lens mounting edge. Each of the left rim 214A and right rim 214B hold respective left and right lenses 218A and 218B respectively, which may provide a vision correction specific to the wearer's prescription. However, this is optional, as the ophthalmic feature detection may be useful for monitoring all eyes, regardless of whether the wearer is nearsighted, farsighted, or has perfect or near perfect vision. Attached to opposing sides of the frame 200 at the left rim 214A is a left temple 220A that is configured to extend along the left temple of the wearer's face, and at the right rim 214B is a right temple 220B that is configured to extend along the right temple of the wearer's face. An end of the left temple 220A distal to the hinge connecting the same to the left rim 214A includes a left temple tip 222A that may partially loop around the left ear of the wearer. Similarly, an end of the right temple 220B distal to the hinge connecting the same to the right rim 214B may include a right temple tip 222B that partially loops around the right ear of the wearer. With the temple tips resting on the ears, the temples function to extend the frame out to and position the rims, and hence the lenses attached thereto, in front of the eyes of the wearer. The rims may rest directly on the nose of the wearer, though there are some configurations of eyeglasses incorporating nose pads that are movably coupled to the rims with nose pad arms. The foregoing components of the spectacles assembly 100 are presented by way of example only and not of limitation.

With additional reference to the block diagram of FIG. 3, additional components of the spectacles assembly 100 are shown. The spectacles assembly 100 includes a controller 114, which is understood to be a data processing device that accepts inputs and is capable of executing software instructions of the analysis subsystem 112, and generate resulting outputs based upon the execution of the instructions using the provided input. Accordingly, controller 114 may also include memory to temporarily or permanently store data and instructions, input/output ports to receive data from and send data to components external to the controller, clock circuits, and the like.

In some embodiments, the controller 114 cooperates with a power supply module 328 that regulates and delivers the needed electrical power thereto. The spectacles assembly 100 is intended to be worn by a person without being tethered to a wired power connection. Thus, the spectacles assembly 100 includes a rechargeable battery 330 from which the power supply module 328 derives electrical energy. The specific type and capacity may be selected based upon the overall power consumption by the entirety of the spectacles assembly 100 over a desired operational duration. The battery 330 with the requisite power capacity to operate the controller 114 and the other electrical components of the spectacles assembly 100 is understood to have a significant physical footprint, and so it may be located within a temple opposite the controller 114.

As the spectacles assembly 100 operates over time, the reserve power in the battery 330 will be drained, and so in order to continue functioning, it may need to be recharged. In this regard, the spectacles assembly 100 also incorporates a charging circuit 332 that can connect to an external power source. The charging interface for making this connection may be a universal serial bus (USB) port 334, which has a dedicated pinout for a power supply. As will be described in further detail below, embodiments of the present disclosure contemplate data transfer to and from the spectacles assembly 100. A single USB port 334 for both charging and data transfer may be incorporated into the spectacles assembly 100 (e.g., on the right temple 220B). There are various form factors for USB ports, any one sufficiently small enough to fit on a temple, such as microUSB or USB-C, may be utilized. In some embodiments other structure and methods can be employed for charging the battery 330. For example, a charging interface comprising conductive contacts may be included on the frame 200 instead of, or in addition to, a USB port 334. As another example, a charging interface comprising wireless inductive charging components can be employed.

The spectacles assembly 100 and ophthalmic monitoring system 150 generally may use a set of images of the wearer's eyes to detect, assess, and monitor ophthalmic features. Thus, the spectacles assembly 100 may include one or more sensor enclosures, at least one of which is oriented toward an eye of the wearer. One or more image sensors, such as cameras 110A and 110B for imaging a wearer's left and right eyes respectively, may be disposed in the one or more sensor enclosures. For example, the cameras may be digital imaging devices with a sensor and a lens. The shutter may be electronically implemented (and hence no mechanical shutter is necessary). The lens focuses the photons of light from a scene or subject onto the sensor, with the sensor converting the captured photons to an electrical signal. The electrical signals, in turn, may be converted to a stream of digital data that represents the image of the captured subject. The data generated by the cameras, without further processing for display, may be referred to as raw data. The raw data for an image may be relayed to the controller 114 for further processing, and at least some of the data may be saved in electronic memory. Additional details regarding the basic functionality of the image sensors will be omitted, as the operational principles of a digital imaging device are deemed to be within the purview of one having ordinary skill in the art.

To capture images of the wearer's eyes, the cameras 110A and 110B—and more specifically the lenses thereof—face rearward from the frame 200 of the spectacles assembly 100. In some embodiments, as shown in FIG. 2, a left camera 110A is incorporated into the rear face of the left rim 214A, while the right camera 110B is incorporated into the rear face of the right rim 214B. Preferably the cameras are positioned and configured such that the field of view of each camera allows capture of much image data as possible relating to the corresponding eye, as well as to the periocular area, which can include the area adjacent the eye and generally within the wearer's orbit.

In addition to the images of the wearer's eye, other environmental data pertaining to the wearer may be captured via one or more environmental sensors 110C. One such sensor may be an accelerometer that generates motion data representing the physical motion imparted upon it. It may be presumed that the motion sensed by the environmental sensors 110C onboard the spectacles assembly 100 generally correspond to the motion of the wearer. The accelerometer translates the physical motion to corresponding data values, which may then be reported to the controller 114. Other environmental sensors 110C such as gyroscopes or magnetometers may serve similar motion or device orientation sensing functions, though other environmental sensors may include thermometers, hygrometers, ambient air pressure sensors, and so forth. As such, data concerning the movement and positioning of the wearer, as well as the surrounding environment, can be captured and supplied to the controller 114. Such data may be correlated with each other. For example, positioning of the wearer's head can be correlated to a moment in time, to which images of the eyes can also be correlated.

As indicated above, the spectacles assembly 100 may cooperate and/or share data with systems and devices external thereto. For example, the data captured by the cameras 110A, 110B and other sensors 110 may be transferred to a user device 104 or computing system 102. Further, data of the broader evaluations computed by the spectacles assembly 100 based upon the image and sensor data from the cameras 110A, 110B and environmental sensors 110C may likewise be transferred to such user device 104 or computing system 102 for further viewing. In such cases, a conventional USB cable may be connected the USB port 334, with the other end of the cable being connected to a corresponding USB port on the user device 104 or computing system 102.

In some embodiments, instead of or in addition to the USB port 334, the data transmissions may occur wirelessly, such as via a Wi-Fi or Bluetooth wireless connection. Accordingly, the communications interface 342 may also or alternatively use a wireless communications module 340. The spectacles assembly 100 may communicate directly with a user device 104 or computing system 102 (e.g., using Bluetooth), or indirectly via a communication network 344 such as a local area network, wide area network, or the internet (e.g., using Wi-Fi).

In some embodiments, one or more components of the spectacles assembly 100 may provide a user input interface for the wearer to mark the occurrence of events, respond to alerts, confirm or deny detection events, initiate execution of certain operations, and the like. For example, a wearer may initiate on-demand download of data from the spectacles assembly 100 to a user device 104 or computing system 102, without necessarily connecting the spectacles assembly 100 to a power source. For example, the wearer may tap the spectacles assembly 100 and cause an environmental sensor 110C (e.g., an accelerometer) to generate motion data representing the tapping action. If the tapping action satisfies one or more criteria (e.g., two or three taps within a short period of time such as 0.5 seconds, 1.0 second, or 1.5 seconds), then execution of an operation such as on-demand download of data from the spectacles assembly 100 to a user device 104 or computing system 102 may be initiated. As another example, the wearer may tap the spectacles assembly 100 to dismiss or confirm an alert, as described in greater detail below.

Example Screen Detection Processing

By way of example, a non-limiting embodiment of ophthalmic feature detection used to detect, monitor, and assess light-emitting screen viewing time will now be described. The example of ophthalmic feature detection to detect, monitor, and assess screen viewing time is contemplated to involve at least two separate sub-functions. The first is screen detection, which involves identifying and analyzing reflections using images of the periocular region to determine the presence of a screen in the wearer's field of vision. According to various embodiments of the present disclosure, a screen may be characterized as a display device that emits light. When a person is viewing such a screen, light originating from the screen reflects off of the periocular region. This reflection is generally rectangular, corresponding to the shape of the display device. The display device may be that of a desktop computer, a portable computer, a tablet, a mobile phone/smartphone, a television, etc. Each of these types of displays is understood to exhibit a characteristic reflection from the periocular region of the eye—usually entirely on the eye itself—and the ophthalmic monitoring system 150 is contemplated to identify them.

Figure 9:
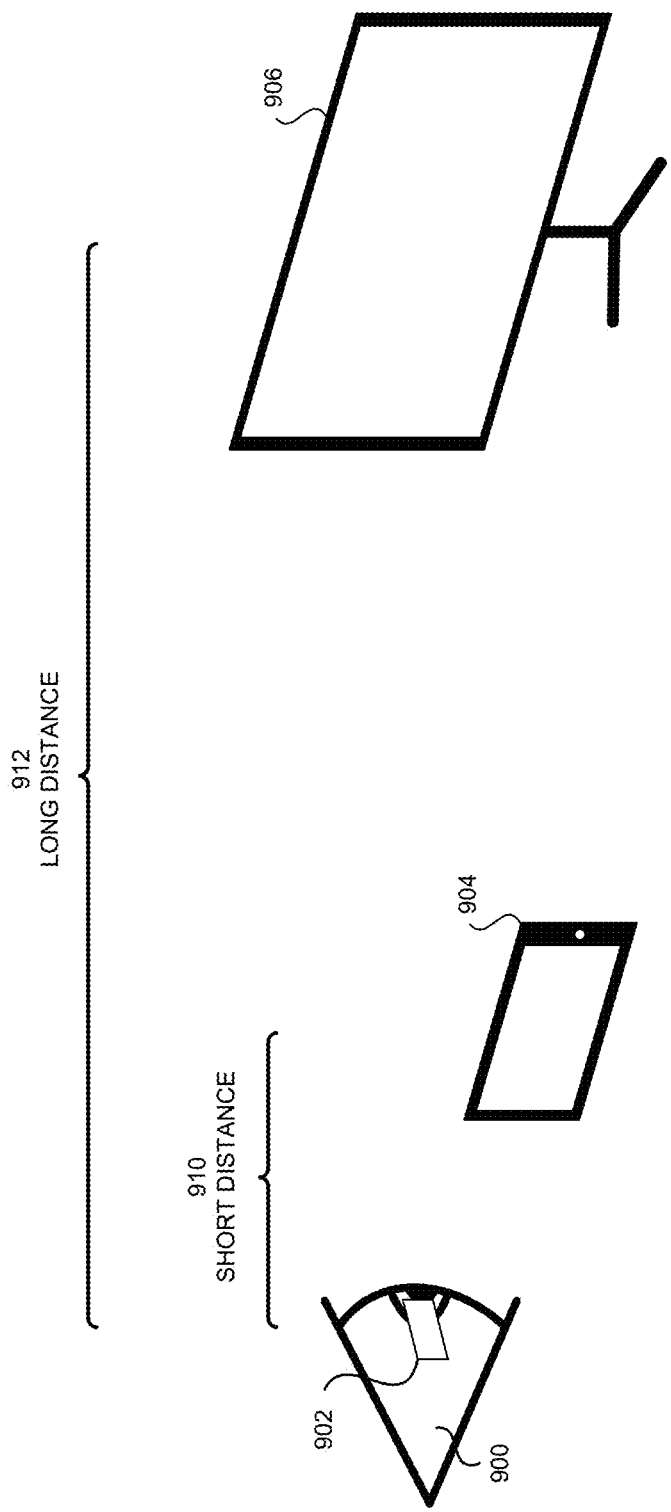
FIG. 9 is a diagram of an eye with a screen reflection and various light-emitting screens according to some embodiments.

It is known that the human eye has a distinctive curvature. Thus, an image of the periocular region of a person viewing a screen may show a skewed reflection as light rays from a two-dimensional surface of the display device are transformed to a complex shape corresponding to the natural curvatures of the eye. FIG. 9 illustrates an eye 900, with a reflection region 902 corresponding to a reflection of the display device. The reflection 902 has an approximate ratio of 16:9 (L:W), but may be deformed somewhat by the curvature of the eye, and thus may have slight curves. In some embodiments, independent of any screen detection, several images of the wearer's eyes, along with other sensor data, can be used to establish a baseline condition of the wearer's eye. For example, the baseline condition identifies the curvature of the eye. This baseline condition can be saved by the analysis subsystem 112. It is also understood that multiple baseline conditions can be saved, each corresponding to variables such as the user's head position (e.g., a head movement metric), the environmental conditions, the viewing direction of the eye, and the like.

Figure 4:
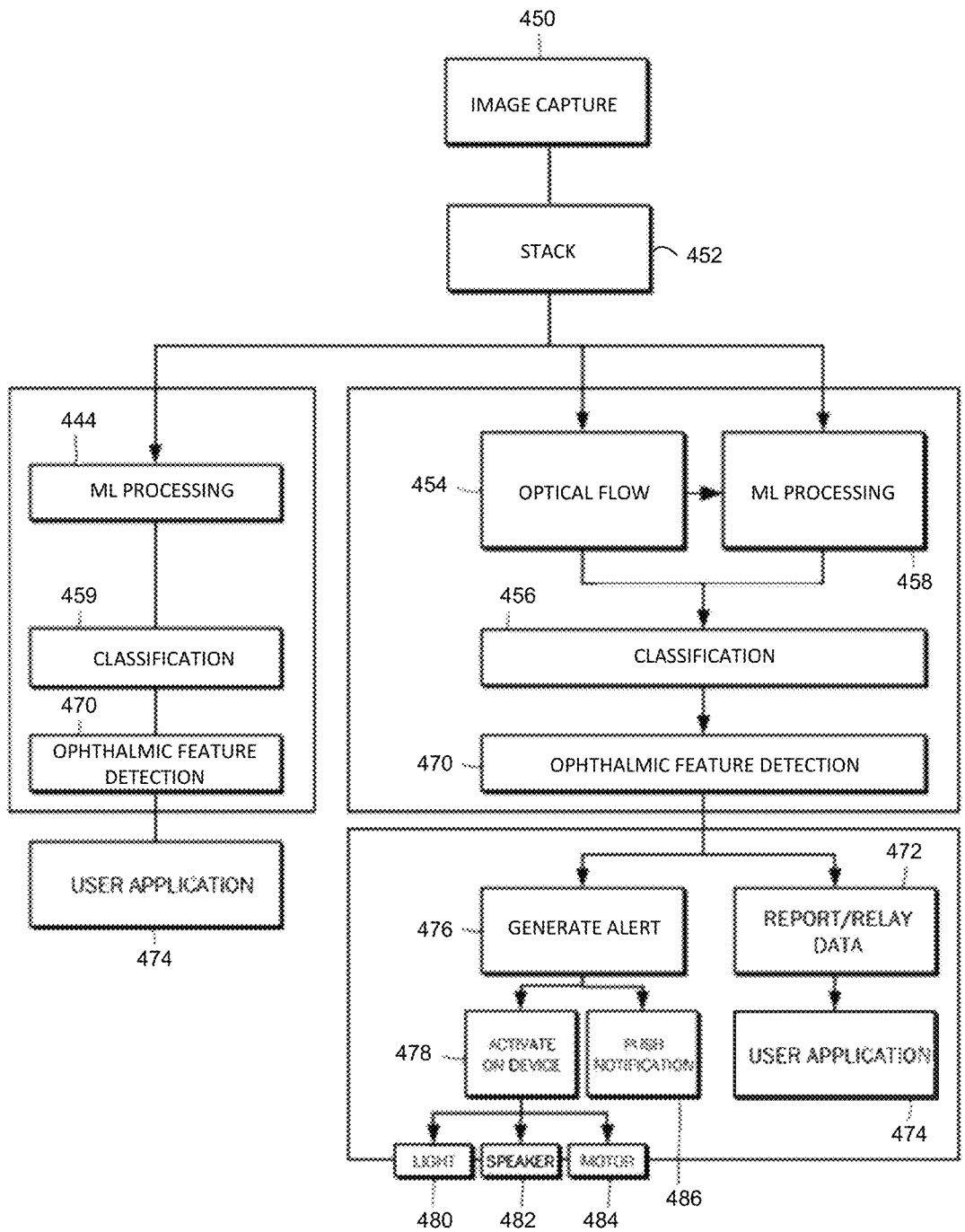
FIG. 4 is a diagram illustrating a flow of processing for ophthalmic feature detection according to some embodiments.

With reference to the block diagram of FIG. 4, a process for monitoring screen viewing may thus begin with an image capture step 450, with one or more images of the eyes being captured and stored into a memory data structure such as a stack 452. Next, optical flow 454 is computed. In an embodiment, optical flow is understood to be the localized measurement of velocities of movement of objects or regions in a sequence of images. Over a plurality of images, recognizable features such as corners and edges within the image are located therein.

The calculated optical flow may then be utilized in a classification step 456, in which the reflection 902 recorded in the image, and its specific position and orientation relative to the overall eye 900, may be used to determine screen shape. For example, by using baseline eye curvature data for the corresponding conditions, a skewed reflection shape can be determined to have been made by a rectangular screen having a particular aspect ratio.

As an alternative to, or as a supplement to the computation of optical flow 454, the analysis subsystem 112 may using machine learning (ML) processing 458 by applying a machine learning model to quantify the likelihood that the glare/rectangular shape of the reflection region 902 is, indeed, that which originates from a light-emitting screen.

In some embodiments, the machine learning model is a support vector machine. The data points utilized by the support vector machine may include brightness and contrast values of the image, from which corners and outlines of the reflection region 902 may be derived. The positional information of the reflection region 902, in turn, may be used to determine screen shape. For example, a horizontal or "landscape" orientation of the reflection region 902 may be associated with a conventional computer monitor or display, while a vertical or "portrait" orientation may be associated with a smartphone or a tablet display.

In some embodiments, the machine learning model is a convolutional neural network (CNN) or a lightweight neural network such as a "You Only Look Once" (YOLO) model. A YOLO model may be implemented as a single neural network that predicts bounding boxes and class probabilities directly from full images in one evaluation, rather than the multi-iteration convolution used by a CNN. As a result, YOLO models are typically faster than traditional CNN-based models or other object detection models. For example, a YOLO model may process images in real-time (e.g., at over 40 frames per second, or in the case of a variant called Fast YOLO, over 150 frames per second). Collectively, neural-network-based image processing models are referred to herein as NNs. An NN may take image data as input, alone or in combination with other data such as data from environmental sensors, data from optical flow 454, or the like. The NN may produce a classification result indicating whether an image includes a reflection of a light-emitting screen.

The position of the display screen in three-dimensional space, or the distance of the wearer from the display screen, may be derived from a sequence of a plurality of images over time, in an ophthalmic feature detection step 470. A time-series analysis of the screen reflection on the periocular region may be used to understand if the user is viewing the screen and its relative position to the user. The aforementioned environmental sensors 110C, such as an accelerometer, gyroscope, or magnetometer, may provide data on relative head movement to determine the distance from the screen to the user, as well as the approximate size of the screen. For example, motion data indicating the user's head is moving or has moved in a downward direction during the course of screen time may be indicative of a near-field light-emitting screen or other near-field object (e.g., based on an analysis of multiple wearers viewing different screens over various periods of time). As another example, user head motion that is primarily or exclusively lateral (e.g., side-to-side), or the lack of statistically significant user head motion in a vertical direction, may be indicative of a far-field light emitting screen.

In some embodiments, the orientation of the eyes can be considered. The interpupillary distance can be determined based on an analysis of an image. For example, the pupils can be identified based on image analysis (e.g., segmentation and identification of pupil location using pixel-based analysis of colors, brightness, etc., or detection of pupil location using a machine learning model trained to detect pupil location in an image of an eye). An interpupillary distance that falls below a particular threshold may be indicative of viewing a near-field light-emitting screen or some other near-field object (e.g., a book).

In still other embodiments, the direction in which the eyes are looking can also be considered. For example, if a reflection of a rectangular screen is identified on the wearer's eye, but it is also deduced that the wearer is looking in a different direction, the analysis subsystem 112 can determine that the wearer was not actually viewing the light-emitting screen.

When analysis subsystem 112 determines that the wearer is viewing a light-emitting screen, the present time may be noted and saved along with the determination. In some embodiments evaluation of screen viewing can be performed substantially continuously. In additional embodiments evaluation of screen viewing is performed periodically, such as every one minute, two minutes, or five minutes. Over the course of time, a record may be developed indicating how much time the user has spent viewing a screen over a period of time. In some embodiments, the type of screen, such as a mobile phone screen, television, or computer monitor, can be determined based on aspects such as aspect ratio, stability of the reflection (i.e., handheld mobile phone will shake more than a computer monitor), distance of screen from the eye, another factor, or a combination thereof. The total screen time of a user may be separated into screen time for different types or distances of light-emitting screen. Such granularity in classification can help in evaluating the overall effect of screen time, as screen time spent viewing near-field screen may be considered more harmful or otherwise a larger contributing factor to eye strain and computer vision syndrome than screen time spent viewing far-field screens.

Although the controller 114 is understood to have sufficient processing power to execute the analysis subsystem and determine the optical flow 454, as well as implement basic ML processing 458, these are understood to be processor-intensive tasks. Thus, the raw image data may be transmitted to a separate system, such as a user device 104 or computing system 102, for processing thereon. More advanced ML processing 444 may be implemented with the abundant computing power available on a computing system 102. For example, larger or more complex machine learning models may be used. Following the classification step 459, screen detection may be performed at ophthalmic feature detection step 470.

As shown in the diagram of FIG. 4, the screen viewing data may be reported at 472 to a user application 474 running on a user device 104, such as a user device of the wearer, an HCP, or a different designated recipient. For screen viewing duration values that exceed a certain threshold (and beyond which are cause for immediate intervention), an alert may be generated at 476. This alert may be presented via an output device of the spectacles assembly 100 at 478, such as by issuing a command to turn on a light emitter such as an indicator light 480, generate an audio output from an audio emitter such as an onboard speaker 482, or actuate a MEMS motor 484 to provide a physical vibration or movement. Notifications 486 can also be sent to other devices, such as the wearer's mobile phone or a third-party device.

Example Blink Detection Processing

By way of example, a non-limiting embodiment of blink-based feature detection used to detect, monitor, and assess blinking will now be described. The example of blink detection is contemplated to involve three separate sub-functions. The first is the detecting and quantifying of eyelid motion, which may be achieved by calculating the optical flow of the pertinent part of the lids. With reference to the block diagram of FIG. 4, prior to this computation of optical flow, there may be an image capture step 450, with a series of one or more images of the eyes being stored into memory data structure such as a stack 452. In an embodiment, optical flow is understood to be the localized measurement of velocities of movement of objects or regions in a sequence of images. Once the series of images are captured, in one implementation, the optical flow 454 is computed. Over a plurality of images, identifiable regions on the eyelids and other parts of the eye are located and tracked to produce an assessment of the motion of the eyelid. The calculated optical flow may then be utilized in a classification step 456, in which the static and dynamic character of the eyelids can be determined from the images of the upper and lower lids. In accordance with various embodiments of the present disclosure, the static character of the eyelids includes "open" and "closed," and the dynamic character of the eyelids include "opening" and "closing." The use of the state of the eyelids to assess blink and droop is understood to reduce the potential dependance on eye fixation, as the position and condition of the iris and pupil are not assumed to be constant over time. The analysis subsystem 112 can match classifications of eye state to a specific time, and store such data. Analysis of such data over a period of time can lead to an estimated blink rate.

As an alternative to, or as a supplement to the computation of optical flow 454, the analysis subsystem 112 may evaluate the sequence of images of the eye using machine learning (ML) processing 458 by applying a machine learning model to quantify the degree and type of motion observed. According to various embodiments, the machine learning model may be a support vector machine, a NN, or another machine learning model. Use of the machine learning may involve a precursor step of capturing a plurality of images and normalizing the images in a pre-processing step. Such initial images may represent various eye states, such as open, closed, opening, and closing. In some embodiments more specific classifications can be used, such as, for example, 25% drooping, or 30% opening. In some embodiments, an average brightness value of images having each of the selected classifications used by the analysis subsystem 112. For example, image brightness values can be compared to such averages in order to classify the eye state depicted in the image. In this manner, processing power used to identify blinking requires only basic brightness values instead of a detailed analysis of structures in the image so as to identify eyelid structures and exact positioning. Processing power, energy, and memory are thus saved by such simplification.

In one implementation, data points utilized by a support vector machine are the difference in average brightness values of a given set of images, as well as the average difference of brightness values from one image to another. These values may be used to yield a margin classifier, in which subsequent evaluations of the same data points from a different set of images can be the basis for classifying the eyelid state. The classification operation performed by the support vector machine may be supplemented with feature extraction based on color data such as RGB (red, green, blue) values or HSV (hue, saturation, value) in the images.

In another implementation, a NN may take image data as input, alone or in combination with other data such as data from environmental sensors, data from optical flow 454, or the like. The NN may be trained to produce a classification result indicating whether input data—an image or series of images, along or in combination with augmentation data from other sensors or optical flow 454—indicates occurrence of a blink.

It is also to be understood that, in addition to calculations performed on the spectacles assembly 100, additional and potentially more complex calculations can be performed by computing resources on a separate computing device such as a user device 104 or computing system 102. Thus, in some embodiments, when the spectacles assembly 100 is not in use, such as each night as the wearer sleeps, image data stored on the spectacles assembly 100 can be communicated to separate computing devices of the ophthalmic monitoring system, which can perform more complex and through analyses. Such analyses and classifications can be compared to the analysis and calculations performed in the analysis subsystem 112 of the spectacles assembly 100. Depending on the accuracy, or inaccuracy, of the analysis subsystem 112 estimate of blink rate, algorithms and averages stored on the spectacles assembly 100 can be updated. For example, machine learning models may be retrained and provided back to the spectacles assembly 100, as described in greater detail below. Thus, on a periodic basis the analysis subsystem's ability to correctly classify eye state can be improved.

Following the classification of the state of the eyelid in step 456, the analysis subsystem 112 proceeds to a time-based assessment of eye state, specifically, generating a blink rate estimate. Upon completing the aforementioned classification, the time history of the eyelid information is known and tied to particular eye states. A time-series analysis of this information may be performed to increase accuracy, and to more fully quantify the eye state as determined. In one embodiment, a machine learning model may be used to characterize the time-series eye state data. In another embodiment, the time-series eye state data may be augmented with time-series pose data from the sensors 110C, e.g., the accelerometer or gyroscope embedded within the spectacles assembly 100, in order to further characterize eye state data. In order to conserve battery power, the analysis subsystem 112 may not capture and evaluate a constant stream of image data. In some embodiments the capture and classification steps may only be performed once every few seconds, with an estimate of the blink rate being extrapolated from the acquired images and the known sampling rate.

Although the analysis subsystem 112 is understood to have sufficient processing power to compute the optical flow 454, as well as implement basic machine learning processing 458, these are understood to be processor-intensive tasks. Thus, the raw image data may be transmitted to a separate system, such as a user device 104 or computing system 102, for processing thereon. More advanced ML processing 444 may be implemented with the abundant computing power available on a computing system 102. For example, larger or more complex machine learning models may be used. Following the classification step 459, blink detection may be performed at ophthalmic feature detection step 470.

As shown in the diagram of FIG. 4, the blink detection data may be reported at 472 to a user application 474 running on a user device 104, such as a user device of the wearer, an HCP, or a different designated recipient. For blink rate values that exceed a certain threshold (and beyond which are cause for immediate intervention), an alert may be generated at 476. This alert may be presented via an output device of the spectacles assembly 100 at 478, such as by turning on an indicator light 480, generating an audio output from an onboard speaker 482, or actuating a MEMS motor 484 to provide a physical vibration or movement. Notifications 486 can also be sent to other devices, such as the wearer's mobile phone or a third-party device.

Evaluation of Sensor Data

Figure 5:
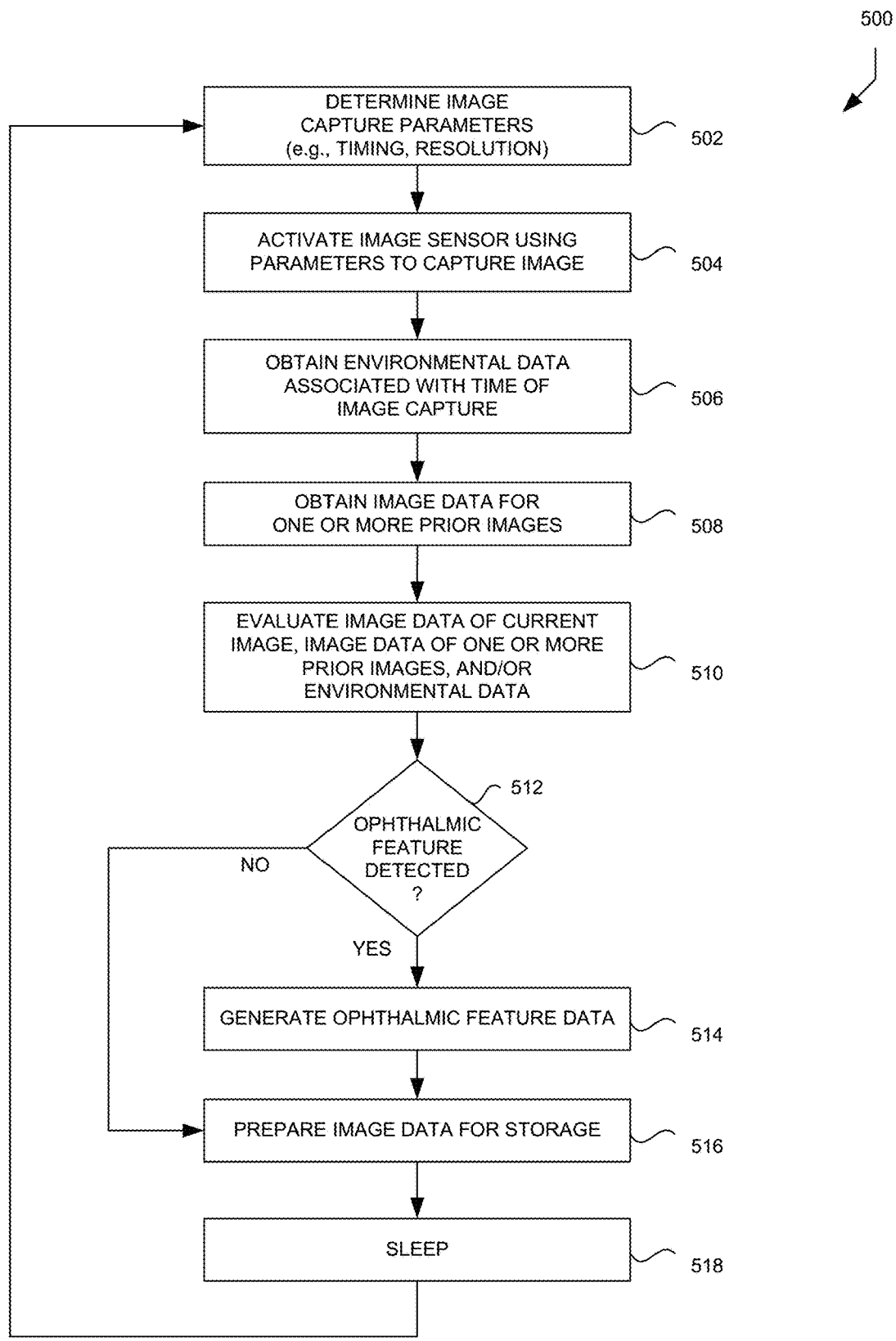
FIG. 5 is a flow diagram of an illustrative routine for managing operation of a spectacles assembly and evaluating sensor data to detect ophthalmic features according to some embodiments.

FIG. 5 is a flow diagram of an illustrative routine 500 that is a computer-implemented method executed by a controller 114 and analysis subsystem 112 to manage the operation and data collection of a spectacles assembly 100, evaluate the collected data, and generate ophthalmic feature data associated with a wearer of the spectacles assembly 100.

The routine 500 may begin in response to an event, such as when a controller 114 begins operation. When the routine 500 is initiated, a set of executable program instructions stored on one or more non-transitory computer-readable media (e.g., flash memory, removable media, etc.) may be loaded into memory (e.g., random access memory or "RAM") of the spectacles assembly 100. In some embodiments, the routine 500 or portions thereof may be implemented on multiple processors or computing devices, serially or in parallel.

At block 502, the controller 114 may determine parameters for capture of images by the image sensor or sensors of the spectacles assembly 100. Image capture parameters may specify timing of image capture or resolution at which images are to be captured.

In some embodiments, image capture parameters may be determined based on a schedule according to which the timing of image capture or resolution at which images are to be captured can vary over the course of a day or other time period. For example, the controller 114 may be programmed to initiate the capture of images at a particular time of day and proceed to capture images every x units of time (e.g., every x milliseconds, seconds, or minutes) thereafter. The images may all be the same resolution, or the controller 114 may be programed to initiate capture of images at different resolutions, such as using a low-resolution baseline for most images (e.g., QVGA, QQVGA), with periodic capture of a set of one or more higher-resolution images (e.g., VGA, XGA, etc.) every x units of time thereafter, every x images captured, etc. As another example, the controller 114 may be programmed to take images at different rates throughout the day, such as less often before and after predetermined points in time (e.g., a morning point in time and an evening point in time), and more often in between the predetermined points in time (e.g., during times of better lighting or more expected wearer activity). The images may all be the same resolution, or the controller 114 may be programed to initiate capture of images using different resolution modes, such as using a first resolution mode that provides relatively low resolution images (e.g., VGA) during certain time periods (e.g., before or after predetermined points in time), with capture of a set of one or more images using a second resolution mode that provides higher-resolution images (e.g., XGA, HD, 4K, etc.) during other time periods (e.g., between the predetermined morning and evening points in time).

In some embodiments, capture of the images may be performed in bursts such that a series of images is collected in a stack similar to a low-frame rate video (e.g., 10-30 frames per second). The series of images may span a period of time (e.g., between about 0.1 seconds and about 10 seconds, or between about 0.16 seconds and about 7.0 seconds), and the period of time may vary or otherwise be determined based on factors such as frame rate or resolution (e.g., lower frame rates or lower resolution may be used for longer-timeframe image series, whereas higher frame rates or higher resolution may result in use of lower-timeframe imager series).

In some embodiments, image capture parameters may be dynamically determined based on factors determined in prior iterations of the routine 500, or in response to events. For example, if the controller 114 determines that the lighting conditions will result in a better high-resolution image than previously-experienced lighting conditions, the controller 114 may cause capture images at the higher resolution for a period of time or quantity of images. As another example, if the controller 114 detects occurrence of an event, such as removal of the spectacles assembly 100, the controller 114 can pause the capture of images until the spectacles assembly 100 has been replaced on the wearer's head.

At block 504, the controller 114 can activate the image sensor(s) using the determined image capture parameters to capture one or more images. The capture of images using different image sensors for different eyes may be initiated substantially simultaneously. In some embodiments, there may be a predetermined or variable delay between capture of an image with one image sensor (e.g., the left camera 110A) and the other image sensor (e.g., the right camera 110B).

At block 506, the controller 114 or analysis subsystem 112 may obtain environmental data from one or more environmental sensors 110C associated with the time of image capture. In some embodiments, the controller 114 may obtain data from one or more motion sensors, a temperature sensor, moisture sensor, ambient light sensor, infrared sensor, or the like. For example, the spectacles assembly 100 may include a sensor array configured to generate sensor data regarding detected acceleration, rotation, or orientation. The sensor array may include various accelerometers and/or gyroscopes (e.g., an accelerometer for each of an x, y, and z axis, and a gyroscope for each of an x, y, and z axis), magnetometers (e.g., to detect the strength or direction of magnetic fields for use in determining the orientation of the spectacles assembly 100 or changes to the orientation), other sensors, or any combination thereof. In some embodiments, or for determination of some ophthalmic features, no environmental data may be obtained or used.

At block 508, the controller 114 or analysis subsystem 112 may obtain image data for one or more prior images. In some embodiments, determination of some ophthalmic features may require or benefit from evaluation of changes in eye characteristics over the course of time, as captured in multiple images. For example, detection of the application of a therapeutic eyedrop may be best performed by determining a difference in tear film height from one point in time (e.g., prior to spectacles assembly removal) to another point in time (e.g., subsequent to spectacles removal). As another example, distinguishing partial blinks from full blinks can benefit from—or require—a series of multiple images captured within a short period of time. In some embodiments, or for determination of some ophthalmic features, no prior imaged data may be obtained during a given iteration of the routine 500.

At block 510, the analysis subsystem 112 may evaluate the image data of the current image, image data of one or more prior images, environmental data, other data, or any combination thereof to determine whether an ophthalmic feature has been detected. In some embodiments, the analysis subsystem 112 may evaluate data to detect a single ophthalmic feature, or subset of ophthalmic features, during each iteration of the routine 500. In some embodiments, the analysis subsystem 112 may evaluate data to detect, during individual iterations of the routine 500 or during each iteration of the routine 500, all ophthalmic features that the analysis subsystem 112 is programmed to detect. Example routines to detect, assess, or monitor various ophthalmic features are described in greater detail below.

At decision block 512, the analysis subsystem 112 may determine whether a particular ophthalmic feature has been detected. If a particular ophthalmic feature has been detected, the routine 500 may proceed to block 514. Otherwise, if a particular ophthalmic feature has not been detected (or if no ophthalmic feature evaluated during the current iteration of the routine 500 has been detected), the routine 500 may proceed to block 516. Example analyses for detection of various ophthalmic features are described in greater detail below.

At block 514, the analysis subsystem 112 may generate ophthalmic feature data regarding the ophthalmic feature or features that have been detected. The ophthalmic feature data may take any of a variety of forms. In some embodiments, the ophthalmic feature data may be or trigger a notification, such as a real-time alert to the wearer (e.g., via an output component of the spectacles assembly 100, via a user device 104), or a notification to an HCP or other designated recipient (e.g., via a user device 104 or computing system 102). In some embodiments, ophthalmic feature data may be stored and used to update ophthalmic detection components (e.g., used as training data for a machine learning model). Example routines to detect, assess, or monitor various ophthalmic features and ultimately generate ophthalmic feature data are described in greater detail below.

In an illustrative example, the analysis subsystem or controller may issue a command to turn on a light emitter such as an indicator light 480, generate an audio output from an audio emitter such as an onboard speaker 482, or actuate a motor 484 to provide a physical vibration or movement. The notification may also or alternatively be sent to other devices, such as a user device 104 of the wearer, an HCP, or another user. The notification may represent detection of an ophthalmic feature, such as detection of a possible event like dry eyes. In some embodiments, the user may provide confirmation or other feedback in response to the notification. For example, if the notification is presented to a wearer, the wearer may confirm or deny detection of the ophthalmic feature by interacting with a user interface, such as by tapping on the spectacles assembly and causing generation of motion data representing the interaction, swiping on a graphical user interface of a user device, or some other action. User interaction data representing the user's interaction (e.g., timestamp of user's interaction, notification presented to user prior to interaction, etc.) may be recorded used for subsequent processing, such as during training or retraining of a machine learning model. In this way, the user interaction data may be used to facilitate reinforcement learning with human feedback.

At block 516, the controller 114 can prepare the image data from the current image for storage. In some embodiments, to prepare the image data for storage, the controller 114 may include the image in a data structure with other images to be eventually committed to persistent storage. By including image data for multiple images together as a group to be stored, the processing and overhead associated with the actual storage operation can be reduced. For example, if the processing and overhead associated with storage operations is significant per storage operation and only affected to a minor degree by the quantity of data being stored, then buffering image data and only committing storage operations when a threshold amount of image data is to be stored or after a threshold period of time has based may reduce the overall computing resources needed to store the image data, thereby conserving processing time, battery life, etc.

At block 518, the controller can determine to sleep for a period of time before beginning a subsequent iteration of the routine 500. The period of time to sleep may be predetermined or dynamically determined. In some embodiments, the controller 114 may be programmed to wait between iterations of the routine 500 for a period of time that may remain static, or that may change over the course of a day. In some embodiments, the controller 114 may be programmed to dynamically determine the period of time to wait between iterations of the routine 500 based on results of processing during a current iteration of the routine 500. For example, if a blink or partial blink detection is to be performed, a relatively short period of time (or no time) may be waited before performing a subsequent iteration of the routine 500. In some embodiments, the controller 114 may be programmed to sleep until occurrence of an event.

Blink-Based Ophthalmic Feature Processing

Figure 6:
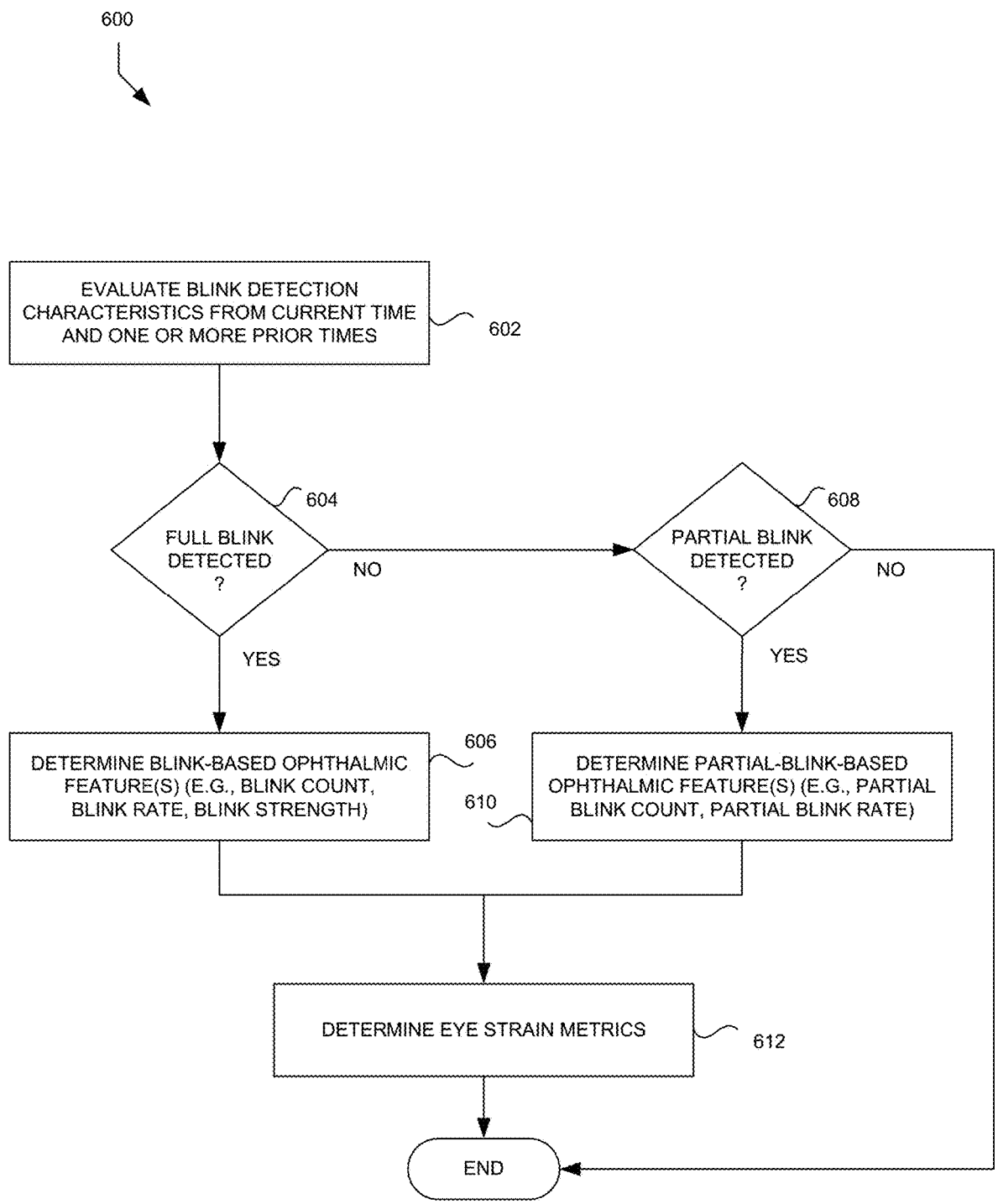
FIG. 6 is a flow diagram of an illustrative routine for determining blink-based ophthalmic features according to some embodiments.

FIG. 6 is a flow diagram of an illustrative routine 600 that is a computer-implemented method for evaluation of sensor data generated by a spectacles assembly 100 to detect blink-based ophthalmic features, determine eye strain metrics, and the like. Example blink-based ophthalmic features detected using routine 600 may include: occurrence of a blink; occurrence of a partial blink; count of blinks; count of partial blinks; blink strength or velocity; blink rate; partial blink rate; effect of blinking on tear film; appearance of ptosis (eyelid droop); other blink-based ophthalmic features; or any combination thereof.

In some embodiments, routine 600 may be executed onboard the spectacles assembly 100, such as by an analysis subsystem 112. Execution of routine 600 onboard the spectacles assembly 100 can permit rapid detection (e.g., real time or substantially real time) of blink-based ophthalmic features and their effect on eye strain. As a result, onboard execution can facilitate rapid generation of notifications to the wearer and rapid implementation of interventions by the wearer in response. For example, a notification may recommend to the wearer application of a therapeutic eyedrop, contact with an HCP, etc. As another example, a real time or substantially real time blink rate may be sent to a separate user device 104 or computing system 102 for presentation, analysis, or the like.

In some embodiments, routine 600 may be executed remotely from the spectacles assembly 100. For example, sensor data generated by the spectacles assembly 100 may be provided—in processed or unprocessed form—to a user device 104 or computing system 102, where the data is processed by analysis subsystem 140 or analysis subsystem 120, respectively. Execution of routine 600 remotely from the spectacles assembly 100 may permit use of more extensive computing resources, and therefore may permit use of larger models (e.g., deep learning models), more complex processing operations, and the like.

In some embodiments, routine 600 may be executed for a given set of input data first onboard the spectacles assembly 100, and then remotely from the spectacles assembly 100 to confirm or reject blink-based ophthalmic features detected onboard the spectacles assembly 100. To ensure that the remote analysis subsystem (whether executing on a user device 104 or computing system 102) is provided with all or substantially all inputs that may be associated with a particular blink-based ophthalmic feature, the analysis performed by the analysis subsystem 112 onboard the spectacles assembly 100 may use detection thresholds or rules that are less likely to result in a false negative (e.g., a determination that input actually indicative of an ophthalmic feature is misclassified as not being indicative of the ophthalmic feature), even if such lower detection thresholds or more permissive rules are more likely to result in a false positive as a result (e.g., a determination that input not indicative of an ophthalmic feature is misclassified as being indicative of the ophthalmic feature). By reducing the occurrence of false negative determinations, this configuration can maximize the number of true positives that may be confirmed or rejected by the remote analysis subsystem. The remote analysis subsystem may then use different thresholds or less permissive rules than the analysis subsystem 112 executing onboard the spectacles assembly 100. Stated in terms of statistical performance metrics, this configuration can be used to optimize the precision and accuracy of the results generated by the remote analysis subsystem, instead of (or in addition to) optimizing recall as done with the analysis subsystem 112 executing onboard the spectacles assembly 100.

Routine 600 may begin in response to an event, such as when image data, environmental data, or a combination thereof is obtained. For example, routine 600 may be executed during blocks 510 to 514 of routine 500. When routine 600 is initiated, a set of executable program instructions stored on one or more non-transitory computer-readable media (e.g., flash memory, removable media, etc.) may be loaded into memory (e.g., random access memory or "RAM") of the device executing the routine. In some embodiments, routine 600 or portions thereof may be implemented on multiple processors or computing devices, serially or in parallel. In the description that follows, the term "analysis subsystem" will be used to referred to the particular analysis subsystem executing the iteration of routine 600, whether it is an analysis subsystem 112 executing onboard the spectacles assembly 100, an analysis subsystem 140 executing on a user device 104, or an analysis subsystem 120 executing on a computing system 102.

At block 602, the analysis subsystem may evaluate blink detection characteristics from the current time and one or more prior times. In the description that follows, in order to distinguish (1) the most-recently captured or generated input data that triggered or otherwise immediately preceded execution of the current iteration of routine 600, from (2) previously-received or generated input data, the most-recently captured or generated input data will be referred to as the "current" input data (or current image data, current environmental data, etc.), and the time at which the current input data was captured or generated may be referred to as the "current" time. Accordingly, previously-captured or generated input data will be referred to as "prior" input data (or prior image data, prior environmental data, etc.), and the time at which the prior input data was captured or generated may be rereferred as a "prior" time.

Evaluation of blink detection characteristics may be performed using pixel-based image analysis, statistical methods, machine learning methods, other methods, or any combination thereof. One example method is described in greater detail above with respect to FIG. 4.

With reference to another illustrative example, by taking sequential images of the eye (e.g., a current image and one or more prior images), the analysis subsystem can track the eyelid position over time and identify a blink. Image segmentation may be performed to segment the current image and extract portions of the image corresponding to the pupil and eyelids. In some embodiments, image segmentation may be performed using a machine learning model (e.g., a CNN or a U-net classifier) to evaluate grayscale versions of the current image and one or more prior images. The output of the evaluation for a given image may be a binary array of pixel brightness values with the same dimensions as the image, but containing a first pixel value (e.g., 0) for each pixel in the background or otherwise outside an area of interest, and second pixel value (e.g., 255) for each pixel that is within an area of interest, such as the upper eyelid, lower eyelid, or pupil. This array may be referred to as a "binary pixel mask," or as a "mask" for brevity. In some embodiments, image segmentation may involve evaluation of greyscale or color pixel values (e.g., HSV) on a row or column basis, and identification of transition points. For example, transition points may be defined as the pixel or pixels at which the greyscale brightness or HSV data changes by a statistically-significant amount or otherwise by greater than a threshold amount from column-to-column or row-to-row within a given image. Additionally, or alternatively, pixel values for the same location in multiple images (e.g., the current image and a prior image) may be compared to identify transition points from image-to-image. For example, HSV data for the current image and one or more prior images may be vectorized, and the vectors for two or more imagers may be compared to identify which portions of the images—and therefore which portions of the eye—have changed. The location or type of the changed portions can evaluated to determine whether they are indicators of blink events, such as covering or uncovering of the pupil, convergence or divergence of the eyelids, or the like.

Figure 7:
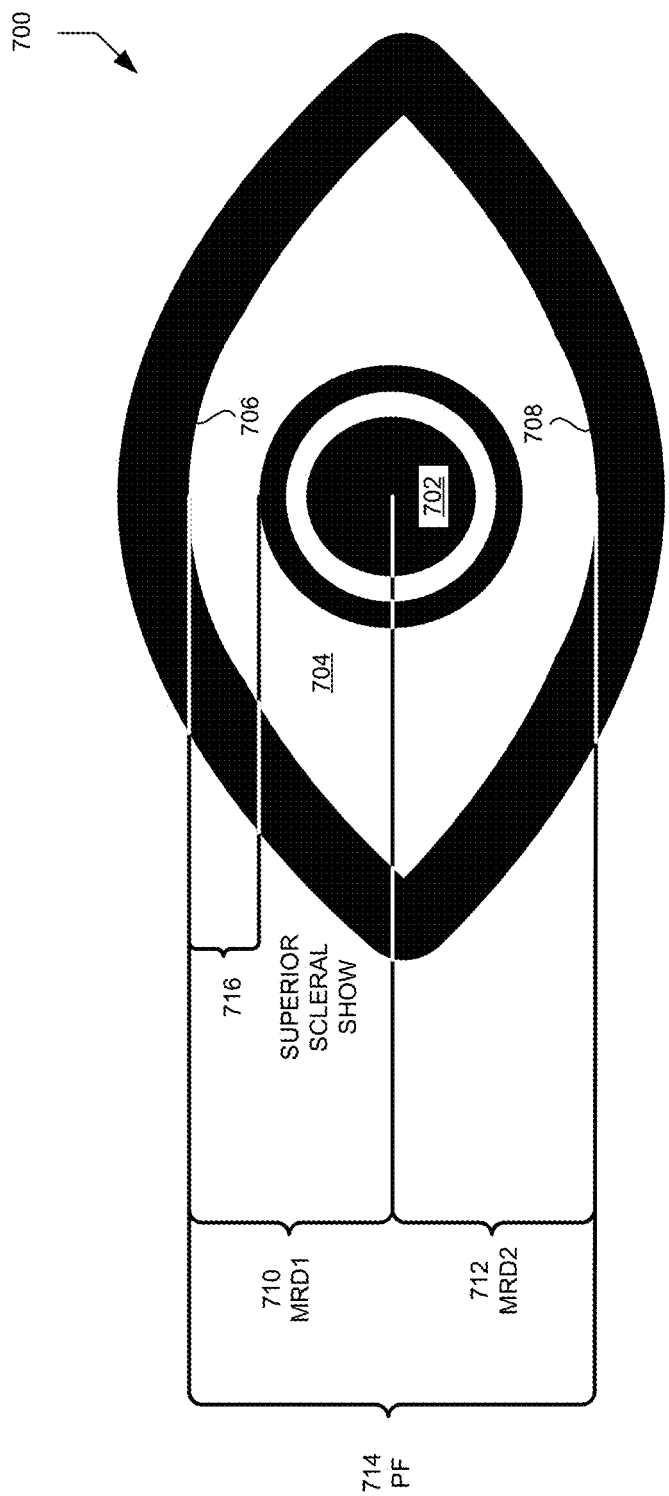
FIG. 7 is a diagram of an eye and measurements thereof according to some embodiments.

In some embodiments, additional ophthalmic features that may or may not be used to detect blink events may be determined using the segmented image data described above. As shown in FIG. 7, the analysis subsystem may use segmented image data indicating the location of the pupil and eyelids to determine one or more margin reflex distances (MRD1 or MRD2), the scleral area, or other features associated with an eye 700. For example, the distance between the center of the pupil 702 and the upper eyelid edge location 706 may be measured to determine an MRD1 score 710. As another example, the distance between the center of the pupil 702 and the lower eyelid edge location 708 may be measured to determine an MRD2 score 712. As a further example, the sum of the MRD1 score 710 and MRD2 score 712 may be computed to determine the palpebral fissure 714.

As another example, the distance between the outer edge of the pupil 702 and another boundary, such as the upper eyelid edge location 706 may be measured to determine the superior scleral show 716, which is the area between scleral boundaries, where the outer edge of the iris forms a first scleral boundary and the upper eyelid edge location 706 forms a second scleral boundary. Similar measurements may be taken to determine other scleral show parameters, which may then be used to determine the scleral area 704. By calculating exposed scleral area, one or more other determinations can be made. For example, eyelid positions for blink detection can be confirmed. As another example, the presence of any scleral area can be considered in determining that an eyepatch is not detected, or the absence of sclera can be considered in determining that an eyepatch is detected, as described below. In addition, or alternatively, the end of the sclera can be identified, which may be considered during other algorithms such as tear meniscus based ophthalmic feature detection by providing a location for which the algorithm can efficiently begin meniscus boundary calculations. In some embodiments, a machine learning model trained on training data images of premasked eyes (e.g., using pixel masks as described herein) may be used to identify the sclera and determine the scleral area. For example, training data images may be filtered by quantity of contours along with confidence of the model using intermediate layers.

Returning to FIG. 6, at decision block 604, the analysis subsystem can determine whether a full blink has been detected. If a full blink has been detected, routine 600 may proceed to block 606. Otherwise, if a full blink has not been detected, routine 600 may proceed to decision block 608 to determine whether a partial blink has been detected.

From the segmented image data, various scores or other data points may be determined and used to detect full or partial blinks. For example, each image may be associated with a time of image capture (e.g., a standardized timestamp representing the quantity of milliseconds that have passed since a reference point in time, such as Jan. 1, 1970 at midnight UTC time). The time at which the location of the lower and upper eyelids converge before diverging again may be determined based on the timestamp of the image within which the convergence is first detected, and may be labeled as a blink event. The time of the blink event may alternatively be determined using other images, such as the image at which the eyelids first begin to converge, the image at which the eyelids completely diverge after converging, or at some other time. The blink event may be recorded as an ophthalmic feature.

The convergence of the upper and lower eyelids indicative of a blink event may be determined using various data or combinations of data from the segmented images. For example, determining convergence of the upper and lower eyelids may be determined from segmented image data for a series of images by tracking the trajectory of the upper and lower eyelids, based on transition points corresponding to the eyelids identified within the images. As another example, palpebral fissure measurements for a series of images may be compared to determine the point at which the palpebral fissure reaches zero or otherwise reaches a minimum value.

In some embodiments, detection of a partial blink may be performed in a similar manner to the full blink detection described above. For example, movement of the upper eyelid to a low point that is within a threshold distance of the lower eyelid, but not complete convergence, may be indicative of a partial blink. As another example, palpebral fissure measurements for a series of images may be compared to determine the point at which the palpebral fissure reduces to a within a threshold value of zero or some other minimum, without subsequently reaching the minimum before the eye opens again.

In some embodiments, as an alternative or supplement to the image-based blink analysis described above, data from environmental sensors such as infrared (IR) receivers may be used to detect blink events. For example, the spectacles assembly 100 may include an IR transmitter (also referred to as an IR sender) and an IR receiver (also referred to as an IR detector). As another example, the spectacles assembly 100 may include a single IR transceiver that incorporates the functionality of both an IR transmitter and IR receiver. As a further example, the spectacles assembly 100 may include two IR transceivers or sets of IR transmitter and IR receivers, one for each eye. One benefit to using IR instead of image-based processing is that IR transmitters and receivers use lower power than image sensors and image-based processing. Thus, blink event monitoring may be done for longer continuous periods of time (e.g., for an entire day between charges).

Inclusion of IR transmitters and receivers allows application of an IR beam to an eye to detect a blink based on reflected IR measured by the IR receiver. The sclera has more reflectivity than the eye lid and, therefore, the transient change in IR signal may be indicative of occurrence of a blink event. In one specific, non-limiting embodiment, the IR sender and IR receiver are turned on simultaneously after elapse of a period of time, such as every 50 ms, every 100 ms, or every 200 ms. In an example, the IR sender and IR receiver are each turned on every 100 ms. Although they both start at the same time, the IR sender may be active for a shorter period of time (e.g., 4 ms, 5 ms, 6 ms) than the IR receiver (e.g., 8 ms, 10 ms, 12 ms). In an example, the IR sender is active for 5 ms, and the IR receiver is active for 10 ms, twice as long as the IR sender. This configuration allows for the IR receiver to collect both IR Tx ON and IR Tx OFF data close in time; the IR Tx OFF can be subtracted from IR Tx ON signal to maximize the signal to noise ratio. The IR receiver is an analog gate for electrical current such that increased IR influx can either increase or decrease current flow. The voltage drop across a resistor connected in series to the sensor is monitored. The frequency of data collection for the voltage can be up to 20 MHz but most commonly will be 0.1 to 10 kHz. The duration of the resistor voltage sampling should be approximately the width of the receiver ON (e.g., about 10 ms). A blink event can be identified in time by a notable change in resistor voltage caused by a physical change in IR reflectivity. That is, a strong IR signal is reflected off of the sclera (e.g., when the eye is open) that causes the voltage read during IR Tx ON and IR Rx ON to be significantly different from the voltage read during IR Tx OFF and IR Rx ON. The sampled voltages are used to calculate a mean value. When this same procedure is repeated and the eye is closed (approximately 20% of a second in which a blink occurs), a weaker IR signal is reflected of off eyelid (eye closed) that causes a less notable voltage difference to be read during IR Tx ON and IR Rx ON versus IR Tx OFF and IR Rx ON.

In some embodiments, IR may be used to detect partial blinks. For example, sequential eyelid position measurements close in time (approximately 10 to 100 Hz) may be beneficial for detecting and distinguishing partial blinks. An IR transmitting and IR receiver can be used, and the speed at which the signal increases and decreases can be determined. The rate of change may be proportional to the strength and speed of the blink. The height of the signal can also be used to determined if the eye fully closed during a blink.

At block 606, in response to detection of a full blink, the analysis subsystem may determine various blink-based ophthalmic features. For example, the analysis subsystem may determine a blink count by incrementing a blink count value. As another example, the analysis subsystem may determine a blink rate by dividing the blink count for a period of time by the quantity of time units in the period of time. As a further example, the analysis subsystem may determine a blink strength, also referred to as a blink velocity. The blink strength may be determined based on the duration of time between full divergence and convergence of the eyelids, or between full divergence and return to full divergence. The distance traveled by the upper eyelid may be computed based on a pixel-wise analysis of one or more images, or may be a predetermined value available to the analysis subsystem. The velocity of the eyelid during the time of the blink can be determined using these values (time of blink and distance traveled).

At block 610, in response to detection of a partial blink, the analysis subsystem may determine various partial blink-based ophthalmic features. For example, the analysis subsystem may determine a partial blink count by incrementing a partial blink count value. As another example, the analysis subsystem may determine a partial blink rate by dividing the partial blink count for a period of time by the quantity of time units in the period of time.

At block 612, the analysis subsystem may use one or more ophthalmic features to determine an eye strain metric indicative of whether a user is experiencing computer vision syndrome. In some embodiments, blink rate, partial blink rate, presence of eye droop, or other ophthalmic features determined during routine 600 or using data generated using routine 600 may be considered when determining an eye strain metric. For example, the analysis subsystem may compare a current blink rate with a blink rate threshold, where the current blink rate represents an average number of blinks per minute during a current period of time (e.g., five minutes, 10 minutes, 15 minutes, 30 minutes, 1 hour) measured backward from the time of the current image. The result may be a binary value indicating whether or not the current blink rate exceeds the threshold, a percentage of the blink rate threshold that has been exhausted, an index based on the degree to which the current blink rate falls below or exceeds the threshold, or another metric. Additional factors and examples of eye strain metric determinations are described in greater detail below. Any ophthalmic feature described herein may be used alone, or in combination with any other ophthalmic feature, as a factor to determine an eye strain metric.

Screen-Based Ophthalmic Feature Processing

Figure 8:
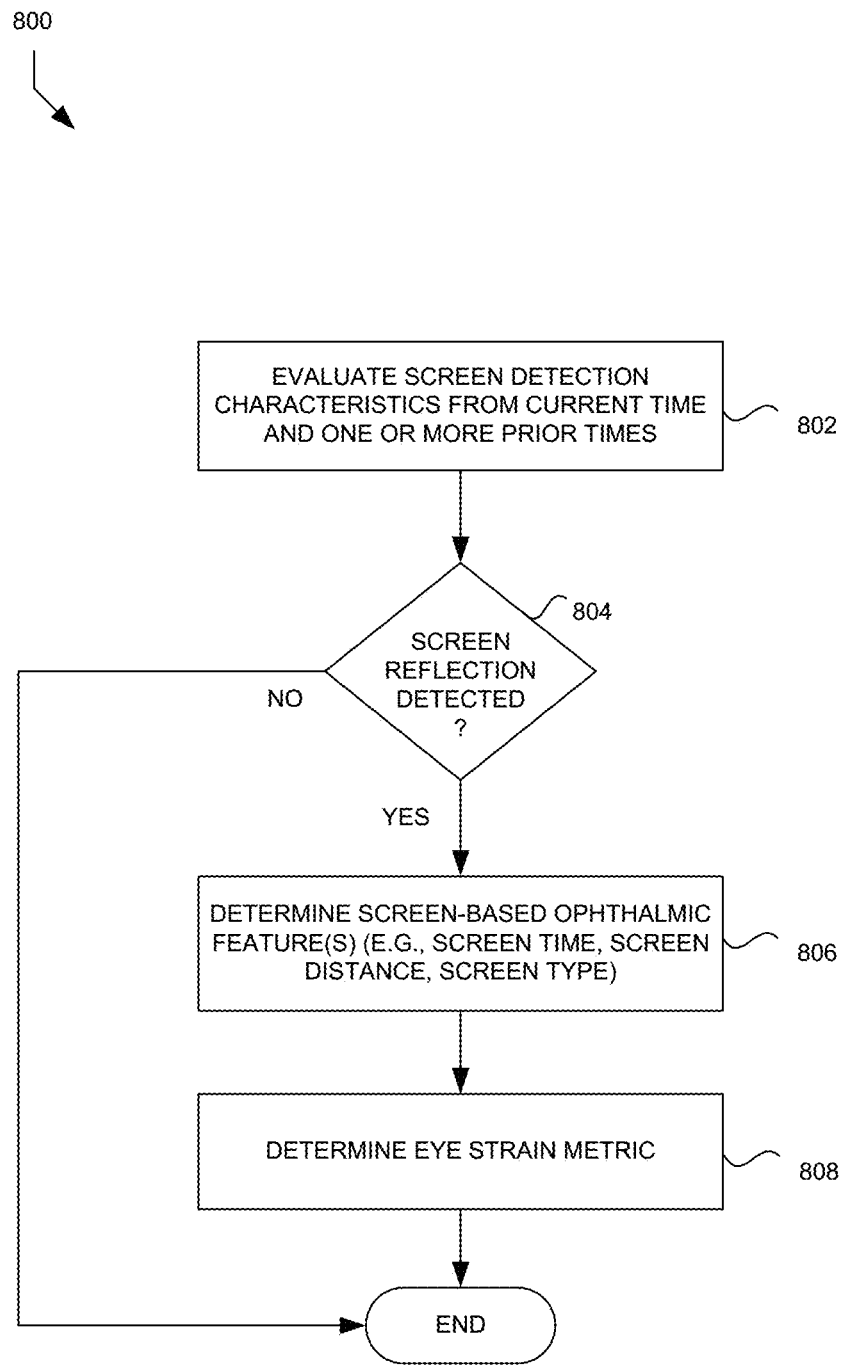
FIG. 8 is a flow diagram of an illustrative routine for determining screen-based ophthalmic features according to some embodiments.

FIG. 8 is a flow diagram of an illustrative routine 800 that is a computer-implemented method for evaluation of sensor data generated by a spectacles assembly 100 to detect screen-based ophthalmic features, determine eye strain metrics, and the like. Example screen-based ophthalmic features detected using routine 800 may include: reflection of a light-emitting screen in the wearer's eye; type of light-emitting screen being viewed by the wearer; duration of time the wearer views a screen (also referred to as "screen time"); distance from a light-emitting screen; duration of time the wearer views any near-field object; distance between the wearer's pupils; brightness of a light-emitting screen being viewed; other screen-based ophthalmic features; or any combination thereof.

In some embodiments, routine 800 may be executed onboard the spectacles assembly 100, such as by an analysis subsystem 112. Execution of routine 800 onboard the spectacles assembly 100 can permit rapid detection (e.g., real time or substantially real time) of screen-based ophthalmic features and their effect on eye strain. As a result, onboard execution can facilitate rapid generation of notifications to the wearer and rapid implementation of interventions by the wearer in response. For example, the wearer may be notified of a recommended reduction in screen time, reduction in screen brightness, increase in ambient lighting, increase in time spent looking at distant or non-light-emitting objects, application of a therapeutic eyedrop, contact with an HCP, etc.

In some embodiments, routine 800 may be executed remotely from the spectacles assembly 100. For example, sensor data generated by the spectacles assembly 100 may be provided—in processed or unprocessed form—to a user device 104 or computing system 102, where the data is processed by analysis subsystem 140 or analysis subsystem 120, respectively. Execution of routine 800 remotely from the spectacles assembly 100 may permit use of more extensive computing resources, and therefore may permit use of larger models (e.g., deep learning models), more complex processing operations, and the like.

In some embodiments, routine 800 may be executed for a given set of input data first onboard the spectacles assembly 100, and then remotely from the spectacles assembly 100 to confirm or reject screen-based ophthalmic features detected onboard the spectacles assembly 100, as described above with respect to routine 600.

Routine 800 may begin in response to an event, such as when image data, environmental data, or a combination thereof is obtained. For example, routine 800 may be executed during blocks 510 to 514 of routine 500. When routine 800 is initiated, a set of executable program instructions stored on one or more non-transitory computer-readable media (e.g., flash memory, removable media, etc.) may be loaded into memory (e.g., RAM) of the device executing the routine. In some embodiments, routine 800 or portions thereof may be implemented on multiple processors or computing devices, serially or in parallel. In the description that follows, the term "analysis subsystem" will be used to referred to the particular analysis subsystem executing the iteration of routine 800, whether it is an analysis subsystem 112 executing onboard the spectacles assembly 100, an analysis subsystem 140 executing on a user device 104, or an analysis subsystem 120 executing on a computing system 102.

At block 802, the analysis subsystem may evaluate screen detection characteristics from the current time and, in some embodiments, one or more prior times. In the description that follows, in order to distinguish (1) the most-recently captured or generated input data that triggered or otherwise immediately preceded execution of the current iteration of routine 800, from (2) previously-received or generated input data, the most-recently captured or generated input data will be referred to as the "current" input data (or current image data, current environmental data, etc.), and the time at which the current input data was captured or generated may be referred to as the "current" time. Accordingly, previously-captured or generated input data will be referred to as "prior" input data (or prior image data, prior environmental data, etc.), and the time at which the prior input data was captured or generated may be rereferred as a "prior" time.

Evaluation of screen detection characteristics may be performed using pixel-based image analysis, statistical methods, machine learning methods, other methods, or any combination thereof. One example method is described in greater detail above with respect to FIG. 4.

With reference to another illustrative example, image segmentation may be performed to segment the current image and extract portions of the image corresponding to areas of interest, such as the sclera and pupil. In some embodiments, image segmentation may be performed using a machine learning model (e.g., a CNN or a U-net classifier) to evaluate grayscale versions of the current image and one or more prior images. The output of the evaluation for a given image may be mask, such as a binary array of pixel brightness values with the same dimensions as the image, but containing a first pixel value (e.g., 0) for each pixel in the background or otherwise outside an area of interest, and second pixel value (e.g., 255) for each pixel that is within an area of interest, such as sclera or pupil. The area of interest may then be further evaluated for screen reflections. For example, a machine learning model trained to detect screen reflections may be used to evaluate the area of interest and classify it, or portions thereof, as positive or negative for screen reflections. As another example, the area of interest may be evaluated based on the greyscale or color pixel values (e.g., HSV) on a row or column basis. Transition points may be identified as described in greater detail herein. If the transition points are determined to likely correspond to edges of a screen reflection, then the analysis system may determine that a screen reflection has been detected.

At decision block 804, the analysis subsystem can determine whether a screen reflection has been detected in the wearer's eye. If a screen reflection has been detected, routine 800 may proceed to block 806. Otherwise, if no screen reflection has been detected, routine 800 may terminate. FIG. 9 illustrates an example in which a screen reflection 902 is detected in a wearer's eye 900.

At block 806, in response to detection of a screen reflection, the analysis subsystem may determine various screen-based ophthalmic features. In some embodiments, the analysis subsystem may determine a screen time that the wearer has been viewing a light-emitting screen. The screen time may be determined using a time of image capture (e.g., a UTC timestamp) associated with each captured image. The first time of image capture for the first image in a series of images in which a screen reflection is detected may be subtracted from the latest time of image capture for the series of images—in this case, the current time for the current image. The difference between the first time and the current time may be saved as a current screen time value. If a separate total screen time value is being captured that does not rely on consecutive screen time (e.g., total screen time for a day), the current screen time value may be added to the total screen time value, or the total screen time value may be incremented by an amount corresponding to the difference between the current screen time value and an immediately-preceding determination of current screen time value that is included within the current screen time value.

In some embodiments, the particular type of screen, the distance of the wearer from the screen, ophthalmic features used to determine the type of screen or distance from screen, other ophthalmic features, or any combination thereof may be determined. For example, the distance between a wearer's pupils—known as the interpupillary distance—may be determined based on the location of the wearer's pupils determined using segmented image data. The wearer's interpupillary distance at the current time—and in particular, the difference between the interpupillary distance at the current time and the maximum interpupillary distance observed or set for the wearer—can indicate whether the wearer is viewing a light-emitting screen 904 at a short distance 910 (or otherwise viewing a near-field object), or viewing a light-emitting screen 906 at a long distance 912 (or otherwise viewing a far-field object), as shown in FIG. 9. Smaller interpupillary distances and greater deviations from the maximum interpupillary distance for the wearer may be indicative that the wearer is a short distance 910 from the light-emitting screen 904 or other near-field object being viewed, while larger interpupillary distances and smaller deviations from the maximum interpupillary distance for the wearer may be indicative that the wearer is a long distance 912 from the light-emitting screen 906 or other far-field object being viewed.

In some embodiments, the type of screen may be determined based on one or more factors, such as the orientation of the screen reflection. For example, portrait mode—in which the measured height of the screen or screen reflection is larger than the width of the screen or screen reflection—may be indicative of mobile user devices such as phones. Landscape mode—in which the measured width of the screen or screen reflection is larger than the height of the screen or screen reflection—may be indicative of other types of displays such as televisions, computer monitors, and the like. The type of screen may also or alternatively be determined based on a distance of the wearer from the screen. For example, motion or orientation data from one or more motion sensors of the spectacles assembly 100 (e.g., accelerometers, gyroscopes, magnetometers) can be evaluated to determine whether a wearer's head has moved during the screen time, or the current orientation of the wearer's head. Motion data indicating the user's head is moving or has moved in a downward direction during the course of screen time may be indicative of a near-field light-emitting screen or other near-field object (e.g., based on an analysis of multiple wearers viewing different screens over various periods of time). User head motion that is primarily or exclusively lateral (e.g., side-to-side), or the lack of statistically significant user head motion in a vertical direction, may be indicative of a far-field light emitting screen. These factors may be evaluated using a rules-based analysis (e.g., by comparing values to thresholds indicative of various screen types), or using a machine learning model trained to evaluate input data and classify the likely type of screen or object being viewed. For example, image data, screen reflection measurements, motion data, characterizations of motion data as indicative of near-field or far-field viewing, interpupillary distance measurements, or other data, or any combination thereof may be used to train a screen type classification model, and may be used during routine 800 to determine the type of screen a wearer is currently viewing.

In some embodiments, the brightness of the light-emitting screen being viewed, or the difference in brightness of the light-emitting screen and the environment, may be determined. For example, the brightness of the light-emitting screen may be determined based on a comparison of the brightness of image pixels corresponding to a screen reflection 902 and the brightness of image pixels corresponding to the sclera of the wearer's eye 900. Larger differences in pixel brightness, where the pixels corresponding to the screen reflection 902 are more than a threshold amount brighter than the pixels corresponding to the sclera, may be indicative of a bright light-emitting screen. As another example, the brightness of the environment may be determined and quantified using an environmental sensor such as an ambient light sensor. If the brightness of the light emitting screen (e.g., determined as described above) exceeds a threshold level for the brightness of the environment, the analysis subsystem may determine the wearer is viewing a bright light-emitting screen.

At block 808, the analysis subsystem may use one or more ophthalmic features to determine an eye strain metric indicative of whether a user is experiencing computer vision syndrome. In some embodiments, screen time, screen type, screen distance, screen brightness, environmental brightness, or other ophthalmic features determined during routine 800 or using data generated using routine 800 may be considered when determining an eye strain metric. For example, the analysis subsystem may compare a current screen time with a screen time threshold. The result may be a binary value indicating whether or not the current screen time exceeds the threshold, a percentage of the screen time threshold that has been exhausted, an index based on the degree to which the current screen time falls below or exceeds the threshold, or another metric. Additional factors and examples of eye strain metric determinations are described in greater detail below. Any ophthalmic feature described herein may be used alone, or in combination with any other ophthalmic feature, as a factor to determine an eye strain metric.

Eyepatch-Based Ophthalmic Feature Processing

Figure 10:
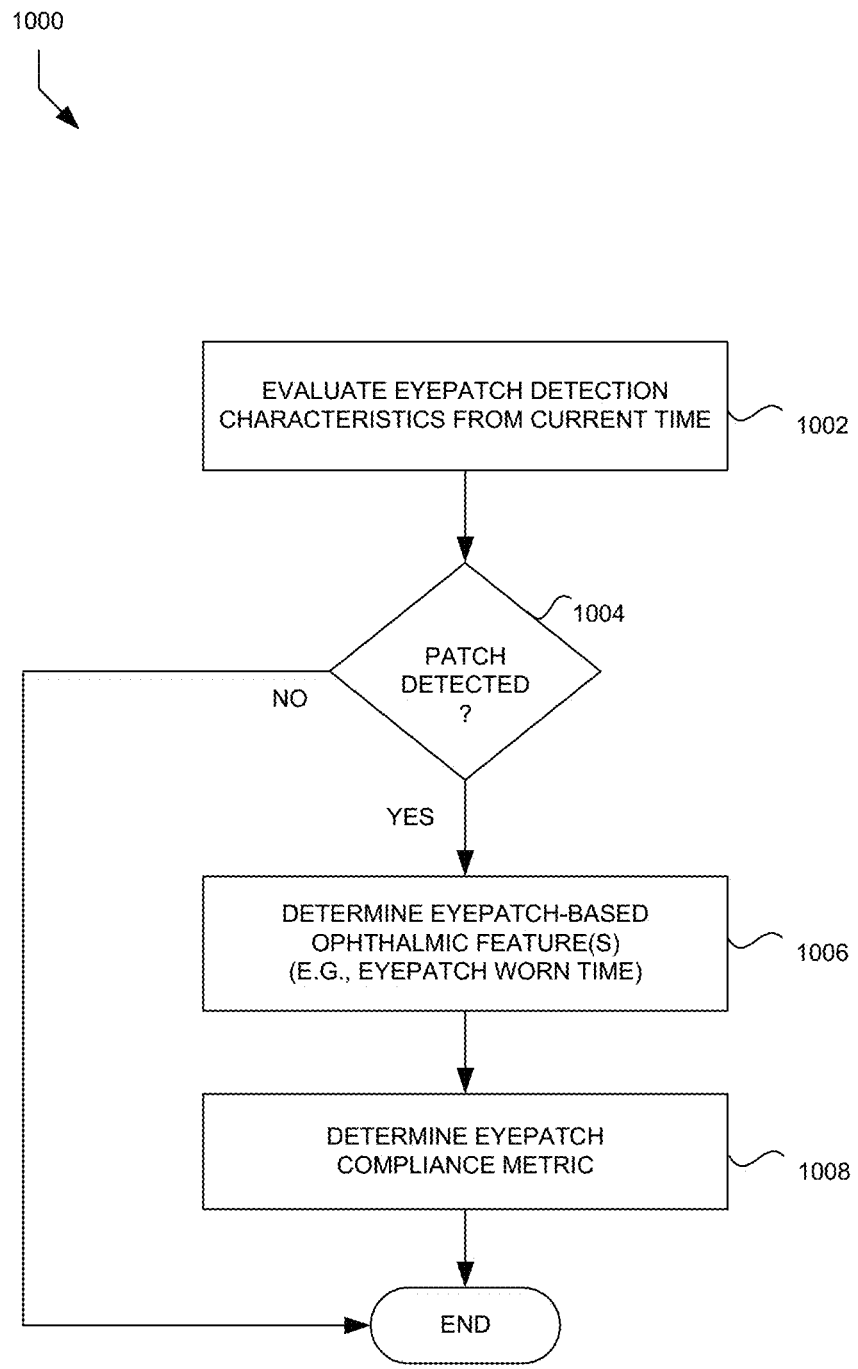
FIG. 10 is a flow diagram of an illustrative routine for determining eyepatch-based ophthalmic features according to some embodiments.

FIG. 10 is a flow diagram of an illustrative routine 1000 that is a computer-implemented method for evaluation of sensor data generated by a spectacles assembly 100 to detect eyepatch-based ophthalmic features, determine eyepatch compliance metrics, and the like. A wearer may be prescribed eyepatch therapy to treat eye conditions such as amblyopia (lazy eye). Eyepatch detection may be performed to determine wearer compliance with an eyepatch therapy prescription. Example eyepatch-based ophthalmic features detected using routine 1000 may include: presence of an eyepatch; absence of an eyepatch; duration of time the wearer is wearing an eyepatch; other eyepatch-based ophthalmic features; or any combination thereof.

In some embodiments, routine 1000 may be executed onboard the spectacles assembly 100, such as by an analysis subsystem 112. Execution of routine 1000 onboard the spectacles assembly 100 can permit rapid detection (e.g., real time or substantially real time) of eyepatch-based ophthalmic features. As a result, onboard execution can facilitate rapid generation of notifications to the wearer and rapid implementation of interventions by the wearer in response. For example, the wearer may be notified whether a recommended duration of time to wear an eyepatch has been reached for a day.

In some embodiments, routine 1000 may be executed remotely from the spectacles assembly 100. For example, sensor data generated by the spectacles assembly 100 may be provided—in processed or unprocessed form—to a user device 104 or computing system 102, where the data is processed by analysis subsystem 140 or analysis subsystem 120, respectively. Execution of routine 1000 remotely from the spectacles assembly 100 may permit use of more extensive computing resources, and therefore may permit use of larger models (e.g., deep learning models), more complex processing operations, and the like.

In some embodiments, routine 1000 may be executed for a given set of input data first onboard the spectacles assembly 100, and then remotely from the spectacles assembly 100 to confirm or reject eyepatch-based ophthalmic features detected onboard the spectacles assembly 100, as described above with respect to routine 600.

Routine 1000 may begin in response to an event, such as when image data, environmental data, or a combination thereof is obtained. For example, routine 1000 may be executed during blocks 510 to 514 of routine 500. When routine 1000 is initiated, a set of executable program instructions stored on one or more non-transitory computer-readable media (e.g., flash memory, removable media, etc.) may be loaded into memory (e.g., RAM) of the device executing the routine. In some embodiments, routine 1000 or portions thereof may be implemented on multiple processors or computing devices, serially or in parallel. In the description that follows, the term "analysis subsystem" will be used to referred to the particular analysis subsystem executing the iteration of routine 1000, whether it is an analysis subsystem 112 executing onboard the spectacles assembly 100, an analysis subsystem 140 executing on a user device 104, or an analysis subsystem 120 executing on a computing system 102.

At block 1002, the analysis subsystem may evaluate eyepatch detection characteristics from the current time and, in some embodiments, one or more prior times. In the description that follows, in order to distinguish (1) the most-recently captured or generated input data that triggered or otherwise immediately preceded execution of the current iteration of routine 1000, from (2) previously-received or generated input data, the most-recently captured or generated input data will be referred to as the "current" input data (or current image data, current environmental data, etc.), and the time at which the current input data was captured or generated may be referred to as the "current" time. Accordingly, previously-captured or generated input data will be referred to as "prior" input data (or prior image data, prior environmental data, etc.), and the time at which the prior input data was captured or generated may be rereferred as a "prior" time.

Figure 11:
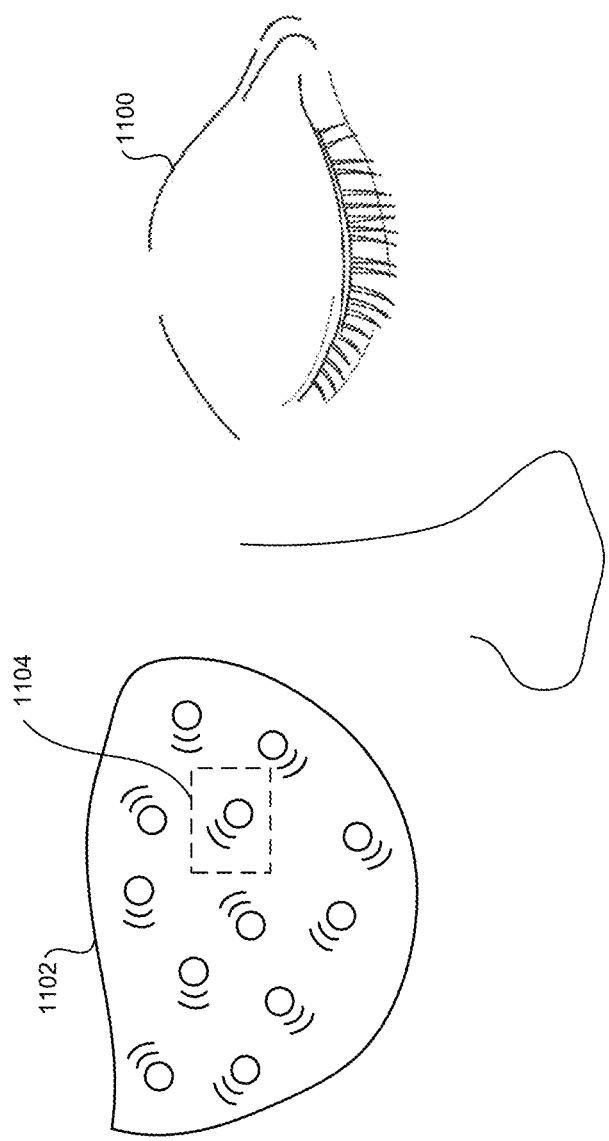
FIG. 11 is a diagram of an eyepatch and detectable design element according to some embodiments.

Evaluation of eyepatch detection characteristics may be performed using pixel-based image analysis, statistical methods, machine learning methods, other methods, or any combination thereof. In some embodiments, the presence of any scleral area can be considered in determining that an eyepatch is not detected, or the absence of sclera can be considered in determining that an eyepatch is detected. With reference to another illustrative example, an image may be evaluated using a machine learning model trained to detect a particular pattern that is printed or otherwise present on the eyepatch. FIG. 11 illustrates an example eyepatch 1102 that a wearer may wear over on eye. As shown, the eyepatch 1102 may include a distinctive design element 1104. The design element 1104 may be generated or chosen to be easily detected by the analysis subsystem, and easy to distinguish from other images that don't include pupils, such as an image of an eye 1100 that is closed or blinking. A machine learning model, such as a support vector machine or a NN, may be trained to detect the specific design element 1104 that is present on the eyepatch 1102, and thus the eyepatch 1102 and the machine learning model are intended to be used together as a system. For example, the machine learning model may be trained using set of training data images. One subset of the images may include the design element 1104 on each image, potentially under different degrees of lighting, with or without imperfections (e.g., printing imperfections, dirt, wrinkles), other use cases, and the like. Each image in this subset may be labeled as positive for eyepatch detection. A second subset of the images may include images similar to those expected to be encountered during use, without the eyepatch 1102 or design element 1104. For example, the second subset may include images of open eyes, closed eyes, eyes in mid-blink or partial blink, eyes with makeup, and the like. Each image in this sub set may be labeled as negative for eyepatch detection. A model trained using such a set of training data images may therefore distinguish between the presence of an eyepatch 1102 with the design element 1104, and absence of such an eyepatch.

In some embodiments, the presence of any scleral area can be considered in determining that an eyepatch is not detected, or the absence of sclera can be considered in determining that an eyepatch is detected.

At decision block 1004, the analysis subsystem can determine whether an eyepatch has been detected in the wearer's eye. If an eyepatch has been detected, routine 1000 may proceed to block 1006. Otherwise, if no eyepatch has been detected, routine 1000 may terminate.

At block 1006, in response to detection of an eyepatch, the analysis subsystem may determine various eyepatch-based ophthalmic features. In some embodiments, the analysis subsystem may determine an eyepatch worn time that the wearer has been wearing an eyepatch. The eyepatch worn time may be determined using a time of image capture (e.g., a UTC timestamp) associated with each captured image. The first time of image capture for the first image in a series of images in which an eyepatch is detected may be subtracted from the latest time of image capture for the series of images—in this case, the current time for the current image. The difference between the first time and the current time may be saved as current eyepatch worn time. If a separate total eyepatch worn time value is being captured that does not rely on consecutive eyepatch worn time (e.g., total eyepatch worn time for a day), the current eyepatch worn time may be added to the total eyepatch worn time, or the total eyepatch worn time may be incremented by an amount corresponding to the difference between the current eyepatch worn time and an immediately-preceding determination of current eyepatch worn time that is included within the current eyepatch worn time.

At block 1008, the analysis subsystem may use the eyepatch detection event or eyepatch worn time to determine an eyepatch compliance metric. For example, a wearer may be prescribed a particular duration of time each day that an eyepatch is to be worn to treat eye conditions such as amblyopia. The analysis subsystem may determine whether the wearer has satisfied the prescribed patching duration. If so, a notification may be generated, such as a user interface presentation (e.g., light, sound, haptic feedback) or electronic message (e.g., push notification to a user device of the wearer or an HCP, notification to a computing system accessible to an HCP, etc.).

In some embodiments, the analysis system may also or alternatively determine that the wearer has removed the eyepatch before the prescribed patching duration for the day has been completed, or has not satisfied the prescribed patching duration by the end of the day. If so, a notification may be generated, such as a user interface presentation (e.g., light, sound, haptic feedback) or electronic message (e.g., push notification to a user device of the wearer or an HCP, notification to a computing system accessible to an HCP, etc.).

Eyedrop-Based Ophthalmic Feature Processing

Figure 12:
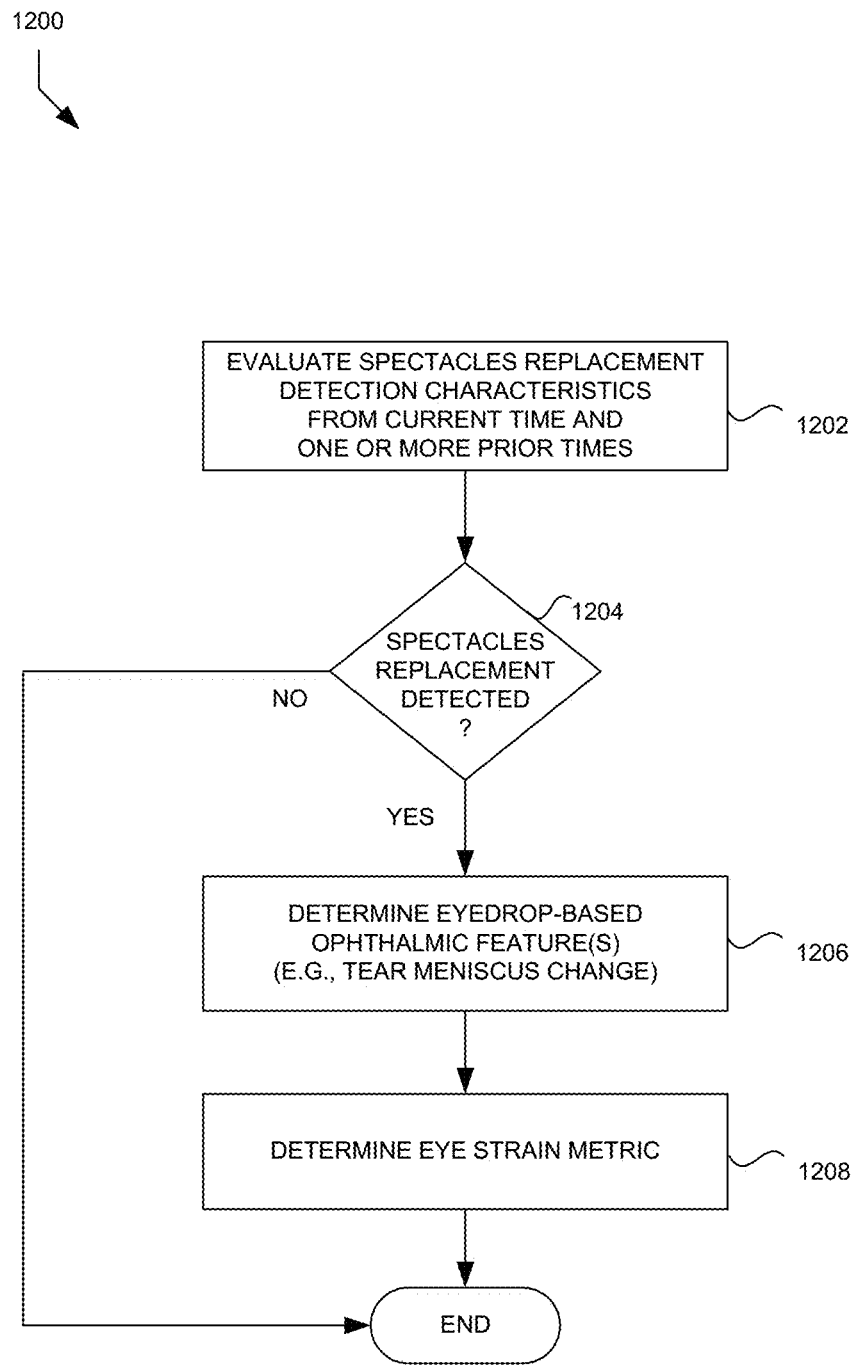
FIG. 12 is a flow diagram of an illustrative routine for determining eyedrop-based ophthalmic features according to some embodiments.

FIG. 12 is a flow diagram of an illustrative routine 1200 that is a computer-implemented method for evaluation of sensor data generated by a spectacles assembly 100 to detect eyedrop-based ophthalmic features, determine eye strain metrics, and the like. A wearer may be prescribed or may otherwise determine to use eyedrop therapy to treat eye conditions such as dry eyes. Eyedrop detection may be performed to determine wearer compliance with an eyedrop therapy, an eyedrop effect, etc. Example eyedrop-based ophthalmic features detected using routine 1200 may include: a pre-drop tear meniscus height; an eyedrop application event; effect of an eyedrop on tear meniscus height; effect of an eyedrop on tear film; other eyedrop-based ophthalmic features; or any combination thereof.

In some embodiments, routine 1200 may be executed onboard the spectacles assembly 100, such as by an analysis subsystem 112. Execution of routine 1200 onboard the spectacles assembly 100 can permit rapid detection (e.g., real time or substantially real time) of eyedrop-based ophthalmic features. As a result, onboard execution can facilitate rapid generation of notifications to the wearer and rapid implementation of interventions by the wearer in response. For example, the wearer may be notified whether an eyedrop is recommended or a previously-applied eyedrop was effective.

In some embodiments, routine 1200 may be executed remotely from the spectacles assembly 100. For example, sensor data generated by the spectacles assembly 100 may be provided—in processed or unprocessed form—to a user device 104 or computing system 102, where the data is processed by analysis subsystem 140 or analysis subsystem 120, respectively. Execution of routine 1200 remotely from the spectacles assembly 100 may permit use of more extensive computing resources, and therefore may permit use of larger models (e.g., deep learning models), more complex processing operations, and the like.

In some embodiments, routine 1200 may be executed for a given set of input data first onboard the spectacles assembly 100, and then remotely from the spectacles assembly 100 to confirm or reject eyedrop-based ophthalmic features detected onboard the spectacles assembly 100, as described above with respect to routine 600.

Routine 1200 may begin in response to an event, such as when image data, environmental data, or a combination thereof is obtained. For example, routine 1200 may be executed during blocks 510 to 514 of routine 500. When routine 1200 is initiated, a set of executable program instructions stored on one or more non-transitory computer-readable media (e.g., flash memory, removable media, etc.) may be loaded into memory (e.g., RAM) of the device executing the routine. In some embodiments, routine 1200 or portions thereof may be implemented on multiple processors or computing devices, serially or in parallel. In the description that follows, the term "analysis subsystem" will be used to referred to the particular analysis subsystem executing the iteration of routine 1200, whether it is an analysis subsystem 112 executing onboard the spectacles assembly 100, an analysis subsystem 140 executing on a user device 104, or an analysis subsystem 120 executing on a computing system 102.

At block 1202, the analysis subsystem may evaluate eyedrop detection characteristics from the current time and, in some embodiments, one or more prior times. In the description that follows, in order to distinguish (1) the most-recently captured or generated input data that triggered or otherwise immediately preceded execution of the current iteration of routine 1200, from (2) previously-received or generated input data, the most-recently captured or generated input data will be referred to as the "current" input data (or current image data, current environmental data, etc.), and the time at which the current input data was captured or generated may be referred to as the "current" time. Accordingly, previously-captured or generated input data will be referred to as "prior" input data (or prior image data, prior environmental data, etc.), and the time at which the prior input data was captured or generated may be rereferred as a "prior" time.

Evaluation of eyedrop detection characteristics may be performed using environmental data analysis, pixel-based image analysis, statistical methods, machine learning methods, other methods, or any combination thereof. With reference to an illustrative example, an image may be evaluated using a machine learning model trained to detect the presence or absence of an eye. Absence of an eye in a prior image and presence of an eye in a current image may be indicative of removal and replacement of the spectacles assembly 100. Such a removal and replacement event may be associated with many events, including cleaning of lenses of the spectacles assembly, face washing, wiping of the eyes, application of an eyedrop, or any of a variety of other events. Detection of a removal and replacement event may trigger further analysis to determine if a particular event of interest has occurred, such as application of an eyedrop as described below.

In some embodiments, environmental data may be used instead of, or in addition to, image data. For example, IR light may be transmitted by an IR transmitter, and a reflection of the IR light may be received by an IR receiver. If the reflection of IR light is not consistent with that of an eye (whether closed or open), and later reflection of IR light is consistent with that of an eye (whether closed or open), then a removal and replacement event may be detected. As another example, motion or orientation data from one or more motion sensors of the spectacles assembly 100 (e.g., accelerometers, gyroscopes, magnetometers) can be evaluated to detect a removal and replacement event. Motion data indicating a motion associated with removal and replacement of the spectacles assembly 100, such as movement away from an as-worn state to a removed state followed by movement toward the as-worn state (e.g., such as vertical motion down and then up), or motion otherwise not associated with typical wearer movements, may be used to detect a removal and replacement event. The motion data may be evaluated against models of motion associated with removal and replacement events, or models associated with normal wearer movements, to detect a removal and replacement event.

In some embodiments, a machine learning model, such as a support vector machine or a NN, may be trained to detect removal and replacement events. For example, the machine learning model may be trained using set of training data images, environmental sensor data (e.g., motion data, IR data), or a combination of image data augmented with environmental sensor data as input training data. One subset of input data items may include various images, environmental data, or combinations thereof known to be associated with removal and replacement event. Each input data item in this subset may be labeled as positive for removal and replacement event detection. A second subset of the input data items may include images, environmental data, or combinations thereof similar to those expected to be encountered during normal wearing of the spectacles assembly, or during a removal event without a following replacement event, or during a placement event not preceded near in time by a removal event. Each input data item in this subset may be labeled as negative for removal and replacement event detection. A model trained using such a set of training data may therefore distinguish between removal and replacement events, and other usage or nonuse of the spectacles assembly 100.

At decision block 1204, the analysis subsystem can determine whether a removal and replacement event has been detected. If so, routine 1200 may proceed to block 1206. Otherwise, if no removal and replacement event has been detected, routine 1200 may terminate.

At block 1206, in response to detection of a removal and replacement event, the analysis subsystem may determine various eyedrop-based ophthalmic features. In some embodiments, the analysis subsystem may evaluate the tear meniscus present on the wearer's eye. For example, the analysis subsystem may evaluate a tear meniscus height, a change in tear meniscus that may be indicative of application of an eyedrop, or another ophthalmic feature. Aligning and subtracting images can help to determine the presence or change of a tear meniscus height indicative of administration of an eyedrop, while segmentation and edge detection can determine meniscus height. Illustratively, the analysis subsystem may compare a current tear meniscus height to a prior tear meniscus height by aligning a current image with a prior image and subtracting one image from the other (e.g., by subtracting the prior image from the current image). Based on a determined difference in the portion of the images that corresponds to the tear meniscus, the analysis subsystem may determine whether the wearer has applied an eyedrop. If so, a notification may be generated, such as an electronic message (e.g., push notification to a user device of the wearer or an HCP, notification to a computing system accessible to an HCP, etc.). An example routine for evaluating tear meniscus height is described in greater detail below.

In some embodiments, the analysis subsystem may tag one or more images associated with the removal and replacement event. For example, the analysis subsystem can tag specific images for later review. When the image data is later offloaded a computing system, the computing system can evaluate the images to see if a large change in meniscus height has occurred. For example, the computing system can execute the routine for evaluating tear meniscus height described in greater detail below. This sequence of events may reveal occurrence of an eyedrop administration event.

At block 1208, the analysis subsystem may use one or more ophthalmic features to determine an eye strain metric indicative of whether a user is experiencing computer vision syndrome. In some embodiments, the effect of an eyedrop on tear film, the reduction in tear film meniscus height over time, or other ophthalmic features determined during routine 1200 or using data generated using routine 1200 may be considered when determining an eye strain metric. For example, the analysis subsystem may compare the height of the tear film meniscus in a current image of the series of images (e.g., determined as described in greater detail below) with an average value of the height of the tear film meniscus in two or more other images in the series of images. The result may be a binary value indicating whether or not the current tear meniscus height exceeds the average value, a percentage by which the current tear film meniscus height falls below or exceeds the average value, an index based on the degree to which the current tear meniscus height falls below or exceeds the average value, or another metric. Additional factors and examples of eye strain metric determinations are described in greater detail below. Any ophthalmic feature described herein may be used alone, or in combination with any other ophthalmic feature, as a factor to determine an eye strain metric.

Tear Film Processing

Figure 13:
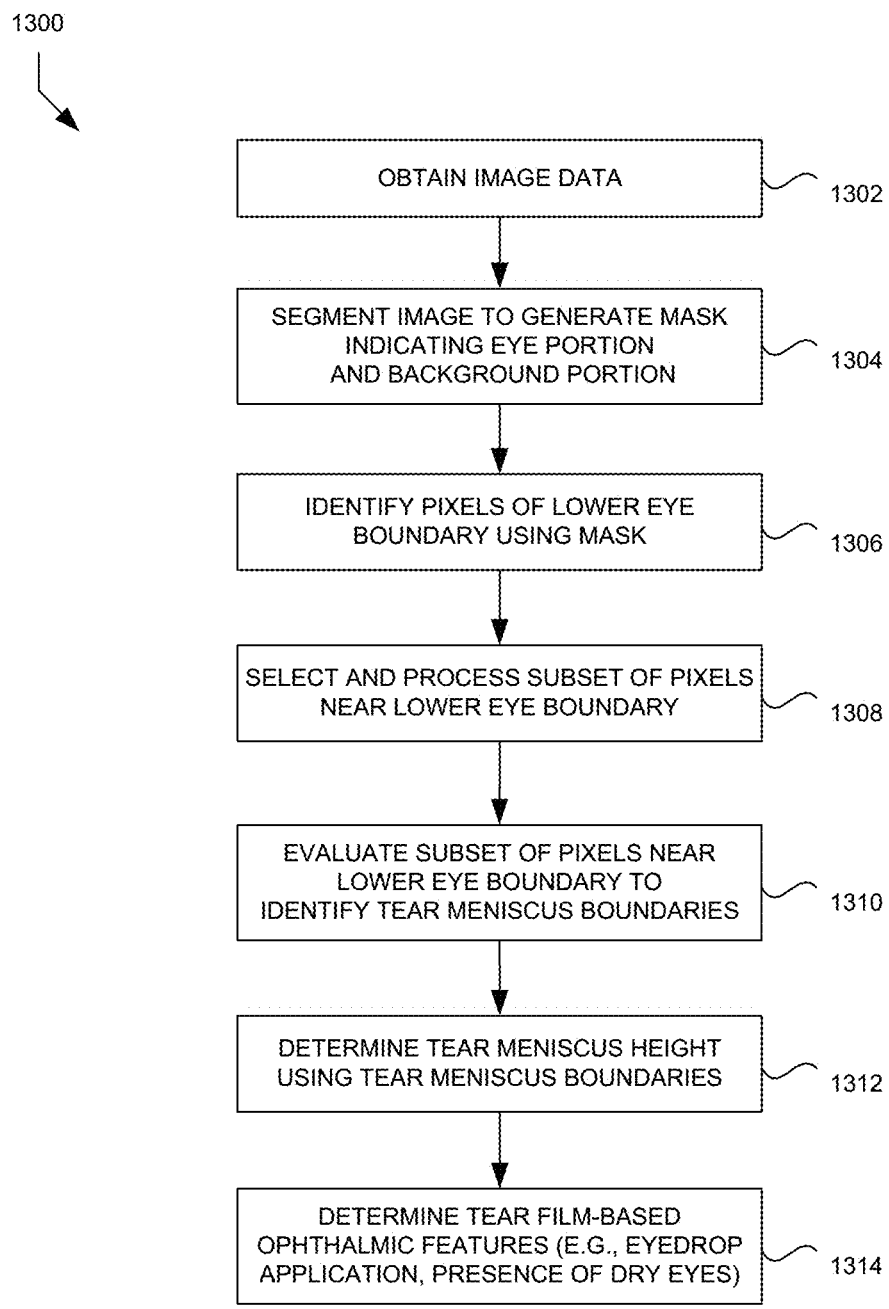
FIG. 13 is a flow diagram of an illustrative routine for determining tear film features according to some embodiments.

FIG. 13 is a flow diagram of an illustrative routine 1300 that is a computer-implemented method for evaluation of image data generated by a spectacles assembly 100 to detect tear film based ophthalmic features. Example tear film based ophthalmic features detected using routine 1300 may include: tear meniscus height; tear break up time; other tear film based ophthalmic features; or any combination thereof.

In some embodiments, routine 1300 may be executed onboard the spectacles assembly 100, such as by an analysis subsystem 112. Execution of routine 1300 onboard the spectacles assembly 100 can permit rapid detection (e.g., real time or substantially real time) of tear film based ophthalmic features. As a result, onboard execution can facilitate rapid generation of notifications to the wearer and rapid implementation of interventions by the wearer in response.

In some embodiments, routine 1300 may be executed remotely from the spectacles assembly 100. For example, sensor data generated by the spectacles assembly 100 may be provided—in processed or unprocessed form—to a user device 104 or computing system 102, where the data is processed by analysis subsystem 140 or analysis subsystem 120, respectively. Execution of routine 1300 remotely from the spectacles assembly 100 may permit use of more extensive computing resources, and therefore may permit use of larger models (e.g., deep learning models), more complex processing operations, and the like.

In some embodiments, routine 1300 may be executed for a given set of input data first onboard the spectacles assembly 100, and then remotely from the spectacles assembly 100 to confirm or reject tear film based ophthalmic features detected onboard the spectacles assembly 100, as described above with respect to routine 600.

Routine 1300 may begin in response to an event, such as when image data, environmental data, or a combination thereof is obtained. For example, routine 1300 may be executed during blocks 510 to 514 of routine 500, or during block 1206 of routine 1200. When routine 1300 is initiated, a set of executable program instructions stored on one or more non-transitory computer-readable media (e.g., flash memory, removable media, etc.) may be loaded into memory (e.g., RAM) of the device executing the routine. In some embodiments, routine 1300 or portions thereof may be implemented on multiple processors or computing devices, serially or in parallel. In the description that follows, the term "analysis subsystem" will be used to referred to the particular analysis subsystem executing the iteration of routine 1300, whether it is an analysis subsystem 112 executing onboard the spectacles assembly 100, an analysis subsystem 140 executing on a user device 104, or an analysis subsystem 120 executing on a computing system 102.

At block 1302, the analysis subsystem may obtain image data. In some embodiments, the image data may be or include images tagged as associated with removal and replacement events or otherwise tagged for further analysis, as described above. In some embodiments, routine 1300 may be performed on images other than tagged images. For example, routine 1300 may be performed periodically, on randomly-selected images, or in response to an event. In the description that follows, in order to distinguish (1) the most-recently captured image data that triggered or otherwise immediately preceded execution of the current iteration of routine 1300, from (2) previously-received image data, the most-recently captured image data will be referred to as the "current" image data, and the time at which the current image data was captured may be referred to as the "current" time. Accordingly, previously-captured image data will be referred to as "prior" image data, and the time at which the prior image data was captured may be rereferred as a "prior" time.

At block 1304, the analysis subsystem may segment the image to generate a mask indicating a background portion and one or more portions of interest. Image segmentation may be performed to segment the current image and extract portions of the image corresponding to the sclera and eyelids. In some embodiments, image segmentation may be performed using a machine learning model (e.g., a CNN or a U-net classifier) to evaluate grayscale versions of the current image and one or more prior images. The output of the evaluation for a given image may be a binary array of pixel brightness values with the same dimensions as the image, but containing a first pixel value (e.g., 0) for each pixel in the background or otherwise outside an area of interest, and second pixel value (e.g., 255) for each pixel that is within an area of interest, such as the upper eyelid, lower eyelid, or pupil. This array may be referred to as a "binary pixel mask," or as a "mask" for brevity. In some embodiments, image segmentation may involve evaluation of greyscale or color pixel values (e.g., HSV) on a row or column basis, and identification of transition points. For example, transition points may be defined as the pixel or pixels at which the greyscale brightness or HSV data changes by a statistically-significant amount or otherwise by greater than a threshold amount from column-to-column or row-to-row within a given image.

Figure 14:
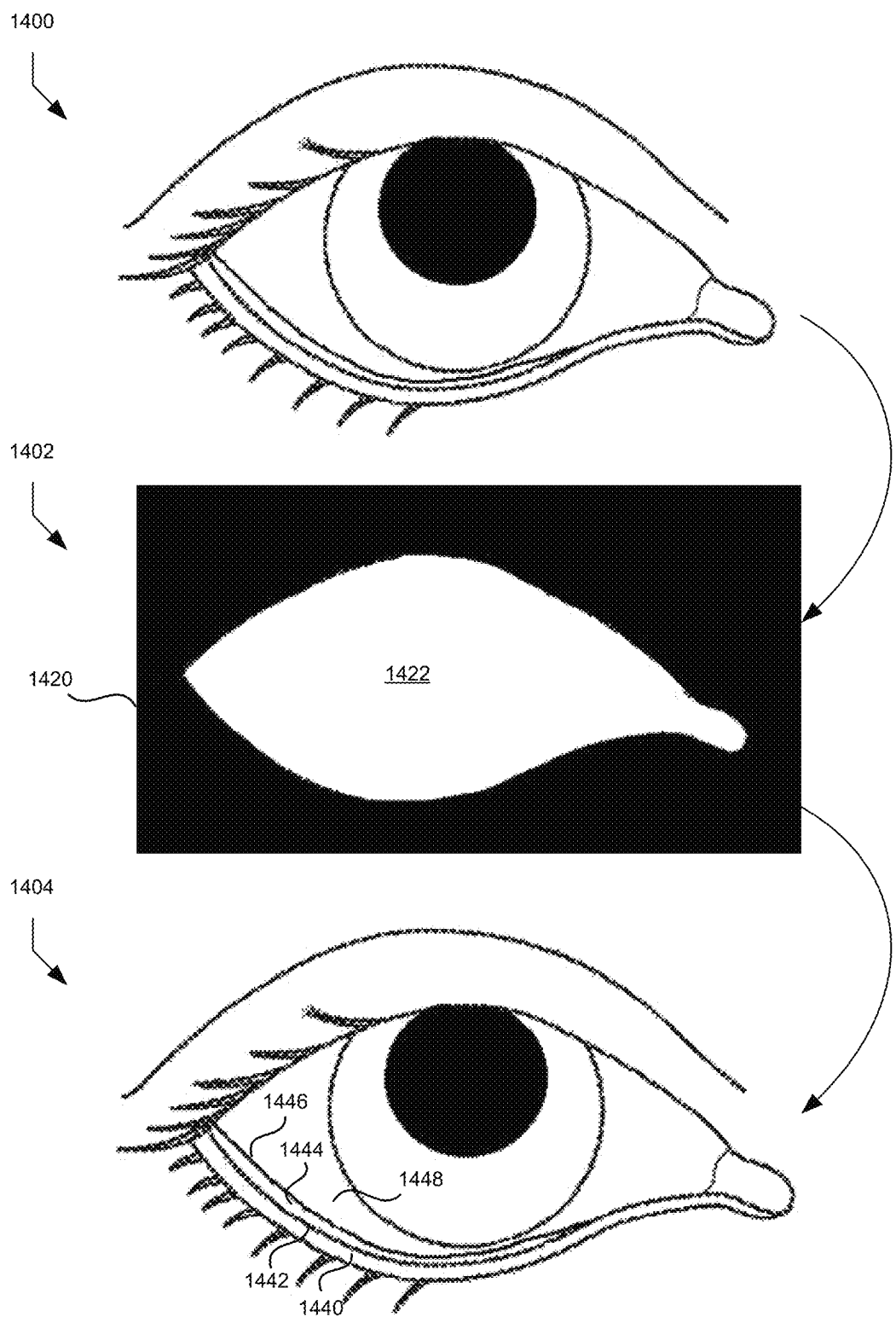
FIG. 14 is a diagram of an eye image, a pixel mask generated from the eye image, and tear film features according to some embodiments.

FIG. 14 illustrates an example image 1400 of an eye, and an example mask 1402 generated based on the image 1400. As shown, the mask 1402 indicates a background area 1420 as a set of pixels with a first value (e.g., 0), and an area of interest 1422 as a set of pixels with a second value (e.g., 255). In this example, the area of interest 1422 is an eye portion of the image Returning to FIG. 13, at block 1306 the analysis subsystem may identify pixels associated with a lower boundary of the eye. In some embodiments, the analysis subsystem may use the mask to identify pixels (e.g., coordinates of pixels) associated with a lower eyelid. For example, the analysis subsystem may use the mask to find the lower eyelid. The lowest row in each column of the mask with a pixel brightness value of 255 corresponds to the upper edge of the lower eyelid. This process may be repeated to determine the coordinates of each pixel in an image for the upper edge of the lower eyelid.

At block 1308, the analysis subsystem may select, from an image, a subset of pixels near the lower eye boundary for further evaluation. In some embodiments, the analysis subsystem may exclude one or more portions of the pixels for the upper edge of the lower eyelid determined at block 1306. For example, the analysis subsystem may exclude between 15% and 25% on one end, such as about 20% off the end closest to the temple. As another example, the analysis subsystem may exclude between 5% and 15% on the opposite end, such as about 10% off the end closest to the nose. In some embodiments, analysis subsystem may then fit a curve (e.g., a high order polynomial) to the coordinates for the remaining pixels of the upper edge of the lower eyelid.

In some embodiments, the analysis subsystem may apply further processing to the remaining pixels of the upper edge of the lower eyelid, or to the entire image or larger parts thereof. For example, the analysis subsystem may enhance the image through local histogram equalization, which can improve image contrast by spreading out the high intensity pixel regions across a larger area or the whole image. High contrast aids in highlighting the edges in the image. As another example, the analysis subsystem may select a region of interest from the image using the lower eyelid upper edge coordinates determined above. The analysis subsystem may select a quantity of the pixels above and below the eyelid line so there is a smaller area to focus on for finding the tear meniscus in a subsequent block of routine 1300. As a further example, the analysis subsystem may apply a filter to the image to remove noise. A gaussian filter can blur the image slightly and the blurring removes some of the high frequency noise and makes it easier to detect edges.

At block 1310, the analysis subsystem can evaluate pixels of an area of interest (e.g., near the lower eye boundary) to identify a tear meniscus boundary. The tear meniscus boundary may present within the image data as an edge above the lower boundary of the eye. FIG. 14 includes a processed image 1404 showing the determined location of the lower boundary of the eye as the upper edge 1442 of the lower eyelid 1440. Above the lower boundary of the eye is the tear meniscus 1444 having a superior edge forming a tear film boundary with the sclera 1448. The superior edge of the team film may be referred to a tear meniscus boundary, and is shown in FIG. 14 as upper boundary 1446.

To identify the tear meniscus boundary, the analysis subsystem may use an edge detection technique, such as Sobel edge detection or Canny edge detection. For example, Sobel edge detection may be applied in the y direction to the processed region of interest in the image. The Sobel filter may use a 3×3 kernel to calculate the gradient of the image and to find areas where there are sharp differences in pixel values which represent edge boundaries between regions in the image. In a Sobel filtered image, transitions from a brighter region to a darker region are represented by a negative value in the gradient, while darker to brighter transitions are represented by a positive value in the gradient. The sclera 1448 is typically brighter than the meniscus 1444 and, depending on the color of the wearer's eyelid skin, the meniscus 1444 is typically darker than the eyelid 1440. Thus, the pixel at the top of the tear meniscus has a small value (more negative gradient), and the pixel at the bottom of tear meniscus has a large value (more positive gradient). For each column, the analysis subsystem may start with the most negative gradient pixel value as being located at the upper boundary 1446 of the meniscus. From that point, the analysis subsystem may find the largest gradient pixel that is below the top. This gives two sets of points: the upper boundary 1446 and bottom edge of the tear meniscus, where the bottom edge of the tear meniscus corresponds to the upper edge 1442 of the lower eyelid 1440.

In some embodiments, instead of using Sobel edge detection, the analysis subsystem may determine the hue and saturation values from each column, and plot the values as (x, y) pairs. The set of points may be grouped into two groups—an eyelid group, and an iris/sclera group-based on predetermined or dynamically-determined color properties associated with the wearer or with wears generally. The hue and saturation information will typically be similar for pixels within each group but dissimilar between the groups. Some pixels that are spatially between the groups may not have color properties that allow clear placement into either group. These pixels may be grouped into a third group. For example, by applying a k-means clustering algorithm to hue and saturation values, the set of points may be clustered in two-dimensional space (corresponding to the two values for each point) into the first two groups mentioned above, and the third group of remaining points connecting or otherwise between the two groups in the image. The pixels corresponding to the middle connecting group may belong to the meniscus/eyelid boundary region. The analysis subsystem may take the highest row value in the middle connecting group for each column and fit a curve (e.g., a 3rd order polynomial) representing the upper boundary 1446 of the meniscus 1444.

In some embodiments, the analysis subsystem may "walk" up from the upper edge 1442 of the lower eyelid 1440, as determined above. For example, the analysis subsystem may evaluate, pixel-by-pixel, the pixels within the region of interest in each column until the edge boundary between eyelid and meniscus is reached. The pixel values transition from predetermined skin hue and saturation values for the wearer to a different value at the lower boundary of the eye. This boundary corresponds to the bottom edge of the meniscus. The analysis subsystem may continue walking up the column until a pixel value that matches the sclera hue and saturation values for the wearer. This location corresponds to the upper boundary 1446 of the meniscus 1444. The analysis subsystem may repeat this walking method for each column.

In some embodiments, a machine learning model, such as a support vector machine or a NN, may be trained to detect the upper boundary 1446 of the meniscus 1444. For example, the machine learning model may be trained using set of training data images. The location of the upper boundary 1446 within each image may be labeled or otherwise provided as reference data for training. A model trained using such a set of training data images may therefore learn the features that distinguish the tear meniscus from other portions of the eye, and more specifically, to distinguish the upper boundary 1446 of the tear meniscus 1444 from other edges present in images of eyes.

At block 1312, the analysis subsystem may determine the tear meniscus height based on the upper boundary 1446 of the meniscus and the lower boundary of the eye, determined as the upper edge 1442 of the lower eyelid 1440. For example, the analysis subsystem may compute the height of the meniscus in pixels, from the upper edge 1442 of the lower eyelid 1440 to the upper boundary 1446 of the meniscus. A height value may be computed for each column of pixels that includes a pixel in the upper boundary 1446 and a pixel in the upper edge 1442 of the lower eyelid 1440, or for a subset of such columns (e.g., once for every x columns, a representative set of x columns, etc.).

The analysis subsystem may determine a single meniscus height for the image (and corresponding time) using the individual the individual meniscus column heights. For example, the analysis subsystem may determine a maximum, minimum, or average tear meniscus height for the image. In some embodiments, the average tear meniscus height may be determined as one of the mean height, the median height, or the mode height. The height of the meniscus in pixels may be converted or normalized to a unit of distance, such as millimeters, centimeters, or inches, based on a predetermined or dynamically determined conversion factor or ratio.

In some embodiments, the analysis subsystem may determine an average meniscus height over multiple images, such as a series of images before or after a removal and replacement event or eyedrop application event. Such an average meniscus height may be referred to as a pre-drop average height (e.g., for an average determined using images preceding an eyedrop application event) or a post-drop average height (for an average determined using images following an eyedrop application event). For example, the analysis subsystem may determine a pre-drop average tear meniscus height as one of the mean height, median height, or mode height of the tear film meniscus over x images or units of time preceding an eyedrop application event. As another example, the analysis subsystem may determine a post-drop average height of the tear film meniscus as one of the mean height, median height, or mode height of the tear film meniscus over x images or units of time following an eyedrop application event.

At block 1314, the analysis subsystem may determine one or more tear film-based ophthalmic features. In some embodiments, the analysis subsystem may determine film-based ophthalmic features based on the location of various edges or the height of the tear meniscus determined above. For example, the analysis subsystem may determine whether an eyedrop has been administrated based on a comparison between tear meniscus heights from two or more different images in a series of images, such as before and occurrence of a removal and replacement event. If the height of the tear meniscus has increased—absolutely, or by a threshold amount—after replacement of the spectacles assembly 100, then the analysis subsystem may determine that the wearer has administered an eyedrop. As another example, the analysis subsystem may determine a tear breakup time based on a comparison between tear meniscus heights from two or more different images in a series of images. If the height of the tear meniscus has decreased absolutely, or by a threshold amount, then the analysis subsystem may determine that the eye is drying out. As a further example, the analysis subsystem may detect a dry eye condition based on a tear film height or based on reflectivity of the scleral area of the eye. If the height of the tear meniscus is below a threshold amount or reflectivity of the scleral area is below a threshold amount, then the analysis subsystem may determine that the eye is drying out.

Machine Learning Model Training and Distribution

Figure 15:
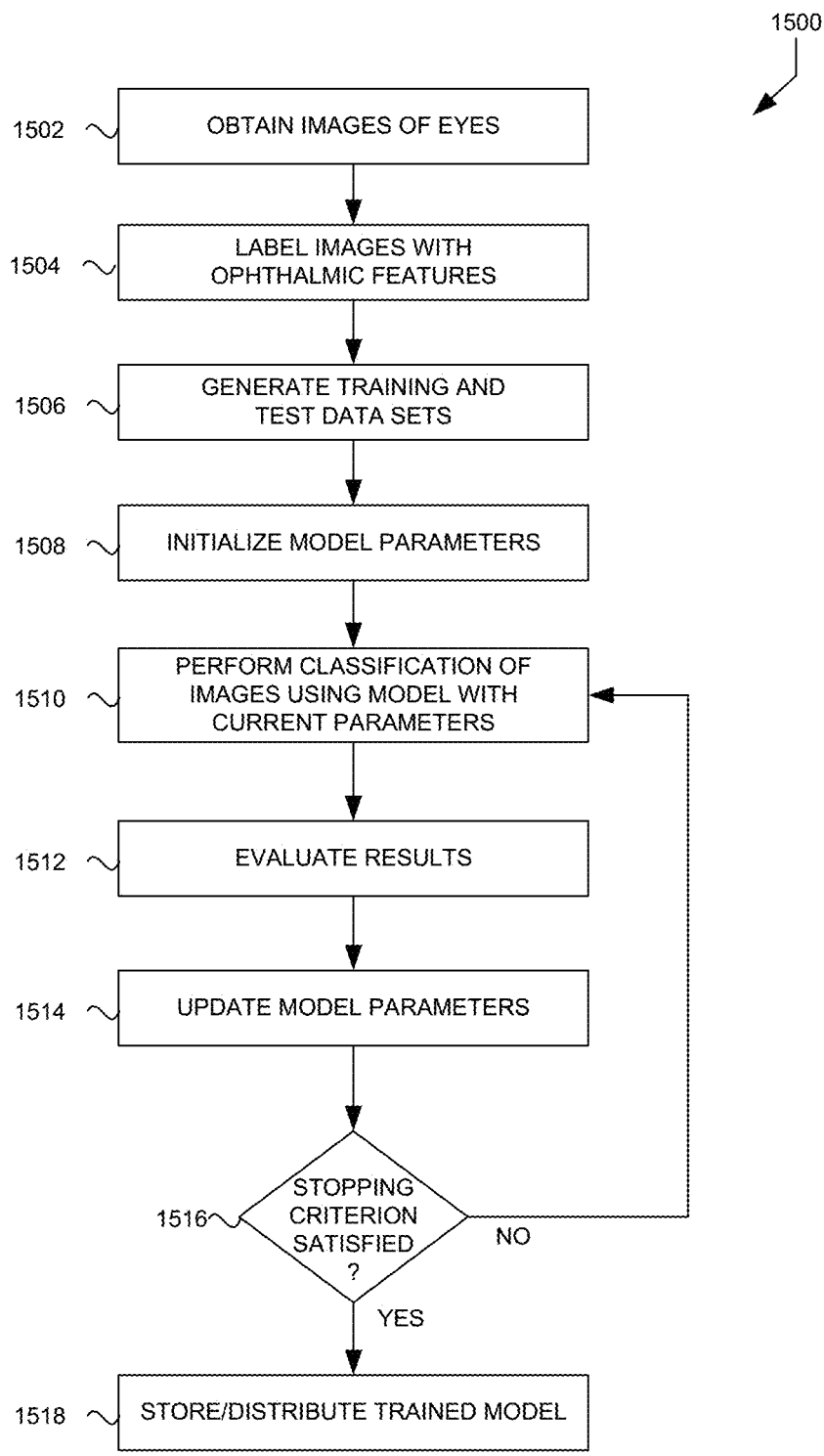
FIG. 15 is a flow diagram of an illustrative process for training an artificial intelligence model using sensor data from spectacles assemblies according to some embodiments.

FIG. 15 is a flow diagram of an illustrative routine 1500 that is a computer-implemented method executed to train a machine learning model to generate detection output regarding one or more ophthalmic features. Although the machine learning training routine 1500 will be described with reference to training a machine learning model using images, it will be appreciated that training may also or alternatively be performed using environmental data either alone or as augmentation data for an image. Portions of the routine 1500 will be described with further reference to the illustrative data flows and interactions between components of the artificial intelligence training system 122 and spectacles assemblies 100A and 100B shown in FIG. 16.

The routine 1500 begins at block 1502. The routine 1500 may begin in response to an event, such as when the artificial intelligence training system 122 shown in FIG. 16 begins operation, or in response to some other event. When the routine 1500 is initiated, a set of executable program instructions stored on one or more non-transitory computer-readable media (e.g., hard drive, flash memory, removable media, etc.) may be loaded into memory (e.g., RAM) of a computing device, such as the computing system 102. In some embodiments, routine 1500 or portions thereof may be implemented on multiple processors, serially or in parallel.

Figure 16:
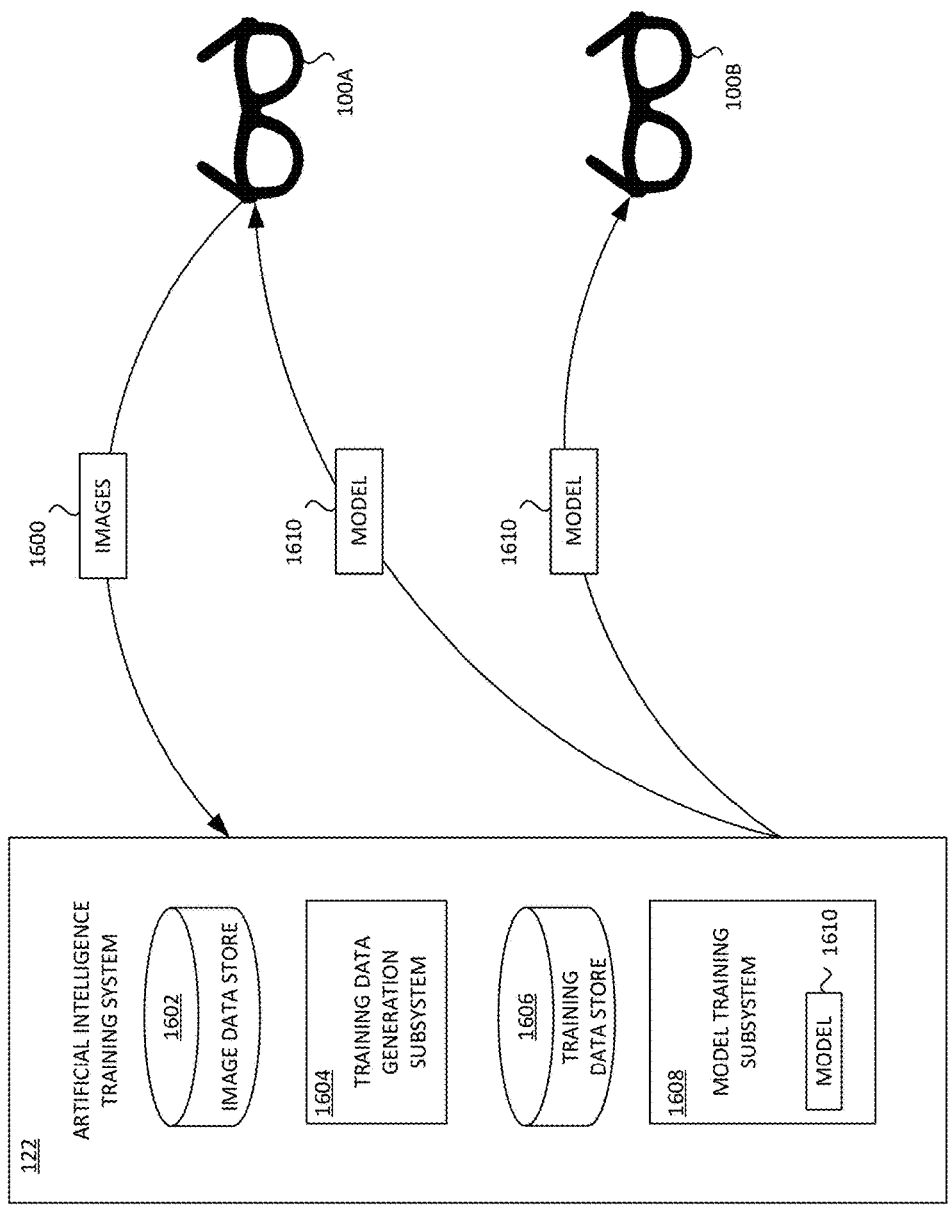
FIG. 16 is a block diagram of illustrative data flows and interactions between spectacles assemblies and an artificial intelligence training system according to some embodiments.

At block 1502, the artificial intelligence training system 122 (also referred to herein simply as the "training system" for convenience) may obtain images from which to generate training data. As shown in FIG. 16, the training system 122 may include various subsystems and data stores to provide machine learning model training functionality. For example, the training system 122 may include an image data store 1602 to store images 1600 generated by one or more spectacles assemblies. The training system 122 may also include a training data generation subsystem 1604 to label images and use the labeled images to generate training data, and a training data store 1606 to store training data. The training system 122 may also include a model training subsystem 1608 for training a machine learning model 1610 using training data from the training data store 1606.

In some embodiments, the training system 122 (or individual components thereof) may be implemented on a single computing system 102. In other embodiments, the training system 122 (or individual components thereof) may be implemented one or more host devices, such as blade servers, midrange computing devices, mainframe computers, desktop computers, or any other computing device configured to provide computing services and resources. For example, a single host device may execute one or more image data stores 1602, training data generation subsystems 1604, training data stores 1606, model training subsystems 1608, some combination thereof, etc. The training system 122 may include any number of such hosts.

In some embodiments, the features and services provided by the training system 122 may be implemented as web services consumable via one or more communication networks. In further embodiments, the training system 122 (or individual components thereof) is provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

The training system 122 may obtain images 1600 from one or more spectacles assemblies 100. The spectacles assemblies 100 may send images 1600 to the training system 122 as the images are generated (e.g., in real time or substantially real time as the spectacles assemblies are being worn), after imaging procedures (e.g., in a batch), on demand after a request from the training system 122, on a schedule, or in response to some other event. The training system 122 may store the images 1600 in an images data store 1602. In some embodiments, all images may be obtained from a single spectacles assembly 100A rather than a set of multiple spectacles assemblies.

In some embodiments, images 1600 may be pre-processed prior to, or as part of the process of, generating training data upon which to train a machine learning model. For example, the resolution of images may be standardized to a resolution upon which the machine learning model is configured to operate (e.g., based on the sized of various layers of the model 1610). As another example, images may be segmented into smaller portions for process instead of, or in addition to, using entire images from spectacles assemblies.

At block 1504, the training data generation subsystem 1604 may label images 1600 with any ophthalmic feature(s) that may be present in the image. In some embodiments, the training data generation subsystem 1604 may generate or otherwise obtain labels for images 1600. For example, the training data generation subsystem 1604 may provide a user interface for HCPs or other experts. The user interface may be a graphical user interface delivered as a web page, mobile application interface, desktop application interface, or via some other mechanism of delivery. Users may use the interface to view images and indicate one or more of: which images do and/or do not include ophthalmic features; where any ophthalmic features are located within individual images; and more detailed information regarding the ophthalmic features, such as an identification of an ophthalmic feature as an open eyelid, a closed eyelid, an eyelid in the process of opening or closing, a pupil location, a screen reflection location, an eyepatch design element location, a tear film meniscus location, or another ophthalmic feature. Interactions to indicate the presence or absence of ophthalmic features (or other associated information) can be used to generate tag data that may be incorporated into the images—or provided to the training system 122 as metadata separately from the images. The tag data may include a flag or other indicator of whether there is any ophthalmic feature in the corresponding image, where in the image the ophthalmic feature(s) may be located, additional information regarding the nature of the ophthalmic feature(s), etc. Illustratively, the tag data may indicate a coordinate location of an ophthalmic feature, an offset from a reference location of an ophthalmic feature, a range of locations for an ophthalmic feature, or some other data from which the training data generation subsystem 1604 can determine the location, size, and/or nature of the ophthalmic feature(s) and label corresponding image(s) accordingly. The training data generation subsystem 1604 may access the tag data and, based thereon, label a portion of the images 1600 as including an ophthalmic feature, and where an ophthalmic feature(s) are in each such image. Illustratively, labelling of an image to indicate an ophthalmic feature may include generating labelling data from the tag data, or copying the tag data or some other data from which the training system 122 can train the machine learning model 1610 to detect the location, size, and/or nature of the ophthalmic feature(s) in an image. The labeled images may be stored as training data images in the training data store 1606.

In some embodiments, training data may include data other than images 1600. Training data input items may include images augmented with augmentation data. The addition of augmentation data can provide the training process with additional data points from which to discern patterns and accurately classify inputs as various ophthalmic features. Moreover, the inclusion of augmentation data can allow corresponding data to be provided at inference time (e.g., when used by an analysis subsystem to process real-world inputs). For example, augmentation data may be or include metadata associated with the images or image capture process, environmental data captured or generated concurrent with capture of the image, other data, or any combination thereof. Examples of augmentation data may include: time of image capture; data representing ambient lighting conditions at image capture (e.g., ambient brightness metrics); head position (e.g., as determined using orientation data from a magnetometer); presence of one or more types of glare; de-identified wearer health data; an MRD1 value; an MRD2 value; an interpupillary distance; a blink rate; a blink strength; a current or total screen time; a mean, median, or mode tear meniscus height (e.g., determined using tear meniscus analysis of a corresponding image); a tear break up time (e.g., determined using a corresponding image and one or more other images in a series); relative humidity at time of image capture (e.g., determined using an environmental sensor such as moisture sensor or humidity sensor); temperature at time of image capture (e.g., determined using an environmental sensor such as a temperature sensor); motion data representing motion of the spectacles assembly before or during the time of image capture (e.g., determined using one or more environmental sensors such as accelerometers or gyroscopes); whether an eyedrop administration operation has been performed in connection with the image capture (e.g., determined using user interface data provided by a wearer); eyedrop warning history, intraocular pressure; other data; or any combination thereof.

At block 1506, the training data generation subsystem 1604 or some other subsystem of the training system 122 may select training data to be used during the current instance of the routine 1500 to train the machine learning model 1610. In some embodiments, the training data generation subsystem 1604 may separate the labelled training images in the training data store 1606 into a training set and a testing set. The training set may be used as described in greater detail below to train the machine learning model 1610. The testing set may be used to test the trained machine learning model 1610. Advantageously, using a separate testing set of images to test the performance of the machine learning model 1610 can help to determine whether the trained machine learning model 1610 can generalize the training to new images that were not presented to the machine learning model during training (or during an iteration of testing).

At block 1508, the model training subsystem 1608 can initialize the parameters of the machine learning model 1610 to be trained. In some embodiments, the machine learning model may be implemented as a NN (such as a CNN or YOLO model as described in greater detail above), a support vector machine, a random forest, some other model, or an ensemble of models. The description that follows relates to training of an NN-based model as an example. However, the example is provided for purposes of illustration only, and is not intended to be limiting or required. In some embodiments, other models may be used, different types of models may be used to detect different ophthalmic features, ensembles of the same type or different types of models may be used to detect a single ophthalmic feature, and so on. In such cases, the particular training operations will depend on the structure of the model(s) being trained, the nature of the input data, the nature of the ophthalmic feature to be detected, the computing resources being used to train the model, the computing resources on which the trained model will be deployed, and various other factors.

Generally described, NNs—including CNNs, deep neural networks (DNNs), recurrent neural networks (RNNs), other NNs, and combinations thereof—have multiple layers of nodes, also referred to as "neurons." Illustratively, a NN may include an input layer, an output layer, and any number of intermediate, internal, or "hidden" layers between the input and output layers. The individual layers may include any number of separate nodes. Nodes of adjacent layers may be logically connected to each other, and each logical connection between the various nodes of adjacent layers may be associated with a respective weight. Conceptually, a node may be thought of as a computational unit that computes an output value as a function of a plurality of different input values. Nodes may be considered to be "connected" when the input values to the function associated with a current node include the output of functions associated with nodes in a previous layer, multiplied by weights associated with the individual "connections" between the current node and the nodes in the previous layer. When a NN is used to process input data in the form of an input vector or a matrix of input vectors (e.g., data representing an image, such as the values of the individual pixels of the image), the NN may perform a "forward pass" to generate an output vector or a matrix of output vectors, respectively. The input vectors may each include n separate data elements or "dimensions," corresponding to the n nodes of the NN input layer (where n is some positive integer, such as the total number of pixels in an input image). Each data element may be a value, such as a floating-point number or integer (e.g., a greyscale value, HSV, or a red-blue-green or "RBG" value of a pixel). A forward pass typically includes multiplying input vectors by a matrix representing the weights associated with connections between the nodes of the input layer and nodes of the next layer, applying a bias term, and applying an activation function to the results. The process is then repeated for each subsequent NN layer. Some NNs have hundreds of thousands or millions of nodes, and millions of weights for connections between the nodes of all of the adjacent layers.

The trainable parameters of the NN include the weights (and in some embodiments the bias terms) for each layer that are applied during a forward pass. In some embodiments, to initialize the parameters of the machine learning model, the model training subsystem 1608 can use a pseudo-random number generator to assign pseudo-random values to the parameters. In some embodiments, the parameters may be initialized using other methods. For example, a machine learning model 1610 that was previously trained using the routine 1500 or some other process may serve as the starting point for the current iteration of the routine 1500.

At block 1510, the model training subsystem 1608 can analyze training data images using the model 1610 to produce training data output. Illustratively, the training data output may correspond to classification determinations regarding whether training data images are negative or positive for ophthalmic features, which portions of the images are likely to be negative or positive, and/or the nature of the ophthalmic features (e.g., screen reflection, eyelid edge, etc.). In subsequent blocks of the routine 1500, the training data output is used to evaluate the performance of the model 1610 and apply updates to the trainable parameters.

A training data output may be structures as an output vector representing the classification or regression determinations made by the model 1610 for the input data (e.g., input image, input environmental data, input image with augmentation data, etc.). Some models 1610 are configured make u classification determinations corresponding to u different classifications (where u is a number corresponding to the number of nodes in the output layer of the NN). The data in each of the u different dimensions of the output vector may be a confidence score indicating the probability that the input data is properly classified in a corresponding classification. Some models 1610 are configured to generate values based on regression determinations rather than classification determinations, or regression determinations that correspond to classification determinations.

The training data from which the input images or other input data items are drawn may also include reference data output vectors. Each reference data output vector may correspond to a particular training data input image or other input data item, and may include the "correct" or otherwise desired output that the model 1610 should produce for the corresponding training data input. For example, a reference data output vector may include scores indicating the proper classification(s) for the corresponding training data input item (e.g., scores of 1.0 for the proper classification(s), and scores of 0.0 for improper classification(s)). As another example, a reference data output vector may include scores indicating the proper regression output(s) for the corresponding training data input item. The goal of training may be to minimize the difference between the output vectors and corresponding reference data output vectors.

By way of illustration, a training data image may be represented as a matrix (e.g., for a greyscale image or raw image data) or a tensor (e.g., for an HSV or RGB image with three color channels) of values in which individual values represent individual pixel values of the image. A convolutional layer of a CNN can generate layer output for nodes connected to particular regions in the input image. For example, each node of a convolutional layer corresponds to a dot product of its associated weights and a region of the prior layer (or input image). There may be more than one feature for which input is being assessed for detection, and the existence of each feature may be assessed using a separate "filter" represented by a set of weights. Thus, in some embodiments the output of a given convolutional layer may be represented as three-dimensional tensor with two dimensions corresponding to spatial dimensions of the input image and a third dimension corresponding to the number of filters.

A model 1610 implemented as described above thus transforms an input image from the image's pixel values to the final detection scores (e.g., classification or regression scores) output by the model 1610. In doing so, the model layers perform transformations that are a function of not only their respective inputs (e.g., the inputs from prior layers), but also of the parameters of the layers (the weights and biases of the neurons). Other portions of the model 1610 may not have separate trainable parameters. For example, activation functions may be implemented as fixed functions that depend only on their respective inputs and are not necessarily trainable.

Returning to the routine 1500, at block 1512 the model training subsystem 1608 can evaluate the results of processing one or more training input images using the model 1610. In some embodiments, the model training subsystem 1608 may evaluate the results using a loss function, such as a binary cross entropy loss function, a weighted cross entropy loss function, a squared error loss function, a softmax loss function, some other loss function, or a composite of loss functions. The loss function can evaluate the degree to which training data output vectors generated using the model 1610 differ from the desired output (e.g., reference data output vectors) for corresponding training data images.

At block 1514, the model training subsystem 1608 can update parameters of the model 1610 based on evaluation of the results of processing one or more training input images using the model 1610. The parameters may be updated so that if the same training data images are processed again, the output produced by the model 1610 will be closer to the desired output represented by the reference data output vectors that correspond to the training data images. In some embodiments, the model training subsystem 1608 may compute a gradient based on differences between the training data output vectors and the reference data output vectors. For example, gradient (e.g., a derivative) of the loss function can be computed. The gradient can be used to determine the direction in which individual parameters of the model 1610 are to be adjusted in order to improve the model output (e.g., to produce output that is closer to the correct or desired output for a given input). The degree to which individual parameters are adjusted may be predetermined or dynamically determined (e.g., based on the gradient and/or a hyper parameter). For example, a hyper parameter such as a learning rate may specify or be used to determine the magnitude of the adjustment to be applied to individual parameters of the model 1610.

With reference to an illustrative embodiment, the model training subsystem 1608 can update some or all parameters of the machine learning model 1610 (e.g., the weights of the model) using a gradient descent method with back propagation. In back propagation, a training error is determined using a loss function (e.g., as described above). The training error may be used to update the individual parameters of the model 1610 in order to reduce the training error. For example, a gradient may be computed for the loss function to determine how the weights in the weight matrices are to be adjusted to reduce the error. The adjustments may be propagated back through the model 1610 layer-by-layer.

At decision block 1516, the model training subsystem 1608 can in some embodiments determine whether one or more stopping criteria are met. For example, a stopping criterion can be based on the accuracy of the machine learning model 1610 as determined using the loss function, the test set, or both. As another example, a stopping criterion can be based on the number of iterations (e.g., "epochs") of training that have been performed, the elapsed training time, or the like. If the one or more stopping criteria are met, the routine 1500 can proceed to block 1518; otherwise, the routine 1500 can return to block 1510 or some other prior block of the routine 1500.

At block 1518, the model training subsystem 1608 can store and/or distribute the trained model 1610. As shown in FIG. 16, the trained model 1610 can be distributed to one or more spectacles assemblies for use in evaluating wearer ophthalmic features.

In some embodiments, as described above, a spectacles assembly 100 may communicate with a user device 104 or computing system 102 to provide images or processed output data in real time or substantially real time, as the spectacles assembly 100 is worn and in use. For example, a spectacles assembly 100 may communicate with a user device 104 or computing system 104 using Bluetooth Low Energy (BLE) or near-field wireless communication protocols. To interactively test or validate a trained model 1610, the trained model 1610 may be deployed to a spectacles assembly 100, and the spectacles assembly may be worn and operated while in communication with a computing device such as a user device 104 or computing system 102. Output of the spectacles assembly 100, such as images captured, environmental data captured, classification determinations generated, and the like may be provided to the computing device for presentation in real time or substantially real time. In this way, the trained model 1610 can be validated under real-world conditions, and without using existing or fabricated testing or validation data.

EXAMPLE EMBODIMENTS

Some example enumerated embodiments are recited in this section in the form of systems and methods, without limitation.

Clause 1. An ophthalmic monitoring system comprising: an eyeglasses frame comprising a left rim and a right rim, at least of one of the left rim and the right rim comprising a sensor enclosure oriented toward an eye of a wearer when the eyeglasses frame is worn; an image sensor disposed in the sensor enclosure to capture images of an eye from within the sensor enclosure; an environmental sensor disposed on the eyeglasses frame and configured to detect a first environmental signal corresponding to a first state in which the eyeglasses frame is being worn and a second environmental signal corresponding to a second state in which the eyeglasses frame has been removed from a head of the wearer; and a processor configured to: (a) activate the environmental sensor; (b) detect the first environmental signal corresponding to the first state; (c) detect the second environmental signal corresponding to the second state; (d) activate the image sensor to capture a plurality of images of the eye; (e) tag a first image of the plurality of images captured by the image sensor, the first image being captured at a first time when the first environmental signal is detected and before the detection of the second environmental signal indicating that the eyeglasses frame has been removed from the head of the wearer; and (f) tag a second image of the plurality of images captured by the image sensor, the second image being captured at a second time after the second environmental signal has been detected and after the first environmental signal is once again detected after the second environmental signal is detected.

Clause 2. The ophthalmic monitoring system of clause 1, wherein the processor is a first processor and further comprising a second processor of the ophthalmic monitoring system, one of the first processor and the second processor being configured to calculate a height of a tear film meniscus in the first image tagged by the first processor.

Clause 3. The ophthalmic monitoring system of clause 2, wherein one or both of the first processor and the second processor is configured to compare a first height of the tear film meniscus in the first image to a second height of the tear film meniscus in the second image and is configured to generate an output indicating that an eyedrop has been applied to the eye based on comparing the first height to the second height.

Clause 4. The ophthalmic monitoring system of clause 3, wherein one or both of the first processor and the second processor is configured to compare the first height to the second height by aligning the first image with the second image and subtracting the first image from the second image.

Clause 5. The ophthalmic monitoring system of clause 4, wherein one or both of the first processor and the second processor is configured to compare the first height to the second height by segmenting the first image and the second image to identify a first tear meniscus height in the first image and/or a second tear meniscus height in the second image.

Clause 6. The ophthalmic monitoring system of clause 4, wherein one or both of the first processor and the second processor is configured to compare the first height to the second height by detecting a first superior edge of the tear film meniscus in the first image and/or a second superior edge of the tear film meniscus in the second image.

Clause 7. The ophthalmic monitoring system of clause 1, wherein the processor is configured to: compare a first brightness value at the first time to a second brightness value at the second time; and generate an output indicating that an eyedrop has been applied to the eye based on the compared the first brightness value to the second brightness value.

Clause 8. The ophthalmic monitoring system of clause 7, wherein the environmental sensor comprises an IR detector and the processor is configured to determine the first brightness value and the second brightness value based on a signal generated by the IR detector.

Clause 9. The ophthalmic monitoring system of clause 1, wherein the processor is configured to: analyze signals from the environmental sensor to detect the eyeglasses frame being removed from the head of the wearer; tag the first image as an image being captured before the eyeglasses frame is removed from the head of the wearer; and tag the second image after the processor analyzes signals from the environmental sensor to detect the eyeglasses frame being worn by the wearer following the detection of the eyeglasses frame being removed from the head of the wearer.

Clause 10. The ophthalmic monitoring system of clause 9, wherein the environmental sensor comprises an inertial sensor and the signals from the environmental sensor comprise motion signals generated by the inertial sensor, the motion signals indicating movement of the eyeglasses frame away from or toward the first state and/or the eyeglasses frame being in the second state.

Clause 11. The ophthalmic monitoring system of clause 1, wherein the processor is configured to: detect removal of the eyeglasses frame from the wearer based on analysis of images of an eyelid of the eye; and detect the eyeglasses frame being worn by the wearer after being removed from the head of the wearer based on analysis of the images of the eyelid of the eye.

Clause 12. The ophthalmic monitoring system of clause 1, wherein the processor is configured to analyze a signal of the image sensor to detect one or more boundaries of a sclera of the eye, the one or more boundaries of the sclera detected forming a portion of a tear film boundary, the one or more boundaries indicating the first state.

Clause 13. The ophthalmic monitoring system of clause 12, wherein detecting one or more boundaries of a sclera of the eye is based on a machine learning model trained using a plurality of training data images.

Clause 14. An ophthalmic monitoring system comprising: an eyeglasses frame comprising a left rim and a right rim, at least one of one of the left rim and the right rim comprising a sensor enclosure oriented toward an eye of a wearer when the eyeglasses frame is worn; an image sensor disposed in the sensor enclosure to capture images of an eye from within the sensor enclosure; and a processor configured to: (a) activate the image sensor to capture a plurality of images of the eye; (b) detect a first state in which the eyeglasses frame is being worn; (c) detect a second state in which the eyeglasses frame has been removed from a head of the wearer; (d) tag a first image of the plurality of images captured by the image sensor, the first image being captured at a first time when the first state is detected and before the detection of the second state indicating that the eyeglasses frame has been removed from the head of the wearer; and (f) tag a second image of the plurality of images captured by the image sensor, the second image being captured at a second time after the second state has been detected and after the first state is once again detected after the second state is detected.

Clause 15. The ophthalmic monitoring system of clause 14, wherein the processor is configured to detect the first state based on analysis of images of an eyelid of the eye.

Clause 16. The ophthalmic monitoring system of clause 14, wherein the processor is configured to detect the first state by analyzing a signal of the image sensor to locate one or more boundaries of a sclera of the eye, the one or more boundaries of the sclera forming a portion of a tear film boundary.

Clause 17. The ophthalmic monitoring system of clause 16, wherein the processor is configured to locate one or more boundaries of a sclera using a machine learning model trained using a plurality of training data images.

Clause 18. The ophthalmic monitoring system of clause 14, wherein the processor is configured to detect the first state or the second state by analyzing a signal of an environmental sensor.

Clause 19. The ophthalmic monitoring system of clause 18, wherein the environmental sensor comprises an inertial sensor and the processor is configured to detect at least one of the first state and the second state by processing a signal generated by the inertial sensor.

Clause 20. The ophthalmic monitoring system of clause 19, wherein the inertial sensor comprises an accelerometer.

Clause 21. The ophthalmic monitoring system of clause 18, wherein the environmental sensor comprises a temperature sensor and the processor is configured to detect at least one of the first state and the second state by processing a signal generated by the temperature sensor.

Clause 22. The ophthalmic monitoring system of clause 18, wherein the processor is configured to determine a pre-drop average tear meniscus height by analyzing images from the image sensor during a period of time including the first time but prior to the second time.

Clause 23. The ophthalmic monitoring system of clause 22, wherein the processor is configured to determine an eyedrop effect by determining a second tear film height by analyzing the second image that is tagged and comparing the second tear film height with the pre-drop average tear meniscus height.

Clause 24. The ophthalmic monitoring system of clause 22, wherein the processor is configured to: segment the second image into an eye portion and a background portion; identify, within the eye portion, a location of a lower eyelid; identify, within the eye portion, an upper edge of a tear film meniscus; and determine a height of the tear film meniscus based on the location of the lower eyelid and a location of the upper edge of the tear film meniscus.

Clause 25. The ophthalmic monitoring system of clause 24, wherein to segment the second image, the processor is configured to generate a binary pixel mask of the eye portion.

Clause 26. The ophthalmic monitoring system of clause 25, wherein to identify the location of the lower eyelid, the processor is configured to determine, using the binary pixel mask, a set of pixels of the lower eyelid.

Clause 27. The ophthalmic monitoring system of clause 24, wherein to identify the upper edge of the tear film meniscus, the processor is configured to determine a gradient within a region of interest.

Clause 28. The ophthalmic monitoring system of clause 24, wherein to identify the upper edge of the tear film meniscus, the processor is configured to: determine a set of points within a region of interest, wherein a point of the set of points represents hue and saturation information; and apply a clustering algorithm to the set of points.

Clause 29. The ophthalmic monitoring system of clause 24, wherein to determine the height of the tear film meniscus, the processor is configured to use a ratio of a quantity of pixels of the tear film meniscus with respect to a quantity of pixels of a region of the eye.

Clause 30. The ophthalmic monitoring system of clause 18, wherein the processor is configured to determine an average value of a tear film height by analyzing images from the image sensor during a period of time including the second time.

Clause 31. A spectacles-mounted ophthalmic monitoring system, comprising: a spectacles frame comprising a left rim and a right rim; an image sensor coupled with the spectacles frame to capture images of a field of view of an eye disposed around at least a portion of a lower eyelid, a portion of an upper eyelid, and a portion of a sclera; and a processor configured to: (a) activate the image sensor to capture a series of images of the field of view; (b) identify a height of a tear film meniscus within the field of view of one or more images within the series of images; (c) identify a reflection of a light-emitting screen in the field of view of one or more images within the series of images; (d) identify a blink rate of one or more images within the series of images; and (e) determine an eye strain metric based on a combination of two or more of the height of the tear film meniscus identified in (a), the reflection of the light-emitting screen identified in (b), and the blink rate identified in (c).

Clause 32. The spectacles-mounted ophthalmic monitoring system of clause 31, wherein determining an eye strain metric comprises comparing the height of the tear film meniscus in a current image of the series of images with an average value of the height of the tear film meniscus in two or more other images in the series of images and comparing a current screen time with a screen time threshold, the current screen time comprising a duration between a first time corresponding to when a first image in the series of images in which the reflection of the light-emitting screen is identified and a current time corresponding to a current time when the current image is captured.

Clause 33. The spectacles-mounted ophthalmic monitoring system of clause 32, wherein determining the eye strain metric further comprises comparing the blink rate with a blink rate threshold, the blink rate comprising an average number of blinks per minute during a current period of five minutes measured backward from the current image.

Clause 34. The spectacles-mounted ophthalmic monitoring system of clause 31, wherein determining an eye strain metric comprises comparing the height of the tear film meniscus in a current image of the series of images with an average value of the height of the tear film meniscus in two or more other images in the series of images and comparing the blink rate with a blink rate threshold, the blink rate comprising an average number of blinks per minute during a current period of five minutes measured backward from the current image.

Clause 35. The spectacles-mounted ophthalmic monitoring system of clause 34, wherein determining the eye strain metric further comprises comparing a current screen time with a screen time threshold, the current screen time comprising a duration between a first time corresponding to when a first image in the series of images in which the reflection of the light-emitting screen is identified and a current time corresponding to a current time when the current image is captured.

Clause 36. The spectacles-mounted ophthalmic monitoring system of clause 31, wherein the processor is further configured to: compare the height of the tear film meniscus with a prior height of the tear film meniscus, wherein the prior height of the tear film meniscus is based on a first image of the series of images, and wherein the height of the tear film meniscus is based on a second image of the series of images captured after the first image; and determine a change in tear meniscus film height from the prior height of the tear film meniscus to the height of the tear film meniscus.

Clause 37. The spectacles-mounted ophthalmic monitoring system of clause 36, wherein to determine the eye strain metric, the processor is further configured to use the change in tear meniscus height.

Clause 38. The spectacles-mounted ophthalmic monitoring system of clause 31, wherein to determine the eye strain metric, the processor is further configured to use a head movement metric.

Clause 39. The spectacles-mounted ophthalmic monitoring system of clause 31, wherein to identify the reflection of the light-emitting screen, the processor is further configured to evaluate at least one image of the series of images using a machine learning model trained using a plurality of training images.

Clause 40. The spectacles-mounted ophthalmic monitoring system of clause 31, further comprising a motion sensor configured to generate sensor data representing at least one of motion of the spectacles frame or orientation of the spectacles frame.

Clause 41. The spectacles-mounted ophthalmic monitoring system of clause 40, wherein the motion sensor comprises at least one of: an accelerometer, a gyroscope, and a magnetometer.

Clause 42. The spectacles-mounted ophthalmic monitoring system of clause 40, wherein the processor is further configured to determine, based on the sensor data, a type of the light-emitting screen.

Clause 43. The spectacles-mounted ophthalmic monitoring system of clause 42, wherein to determine the eye strain metric, the processor is further configured to use the type of the light-emitting screen.

Clause 44. The spectacles-mounted ophthalmic monitoring system of clause 40, wherein the processor is further configured to determine, based on the sensor data, a distance of a wearer from the light-emitting screen.

Clause 45. The spectacles-mounted ophthalmic monitoring system of clause 44, wherein to determine the eye strain metric, the processor is further configured to use the distance of the wearer from the light-emitting screen.

Clause 46. The spectacles-mounted ophthalmic monitoring system of clause 34, further comprising a second image sensor coupled with the spectacles frame to capture images of a second field of view of a second eye, wherein the processor is further configured to: activate the image sensor to capture a second series of images of the second field of view; and determine in interpupillary distance between a first pupil of the eye and a second pupil of the second eye.

Clause 47. The spectacles-mounted ophthalmic monitoring system of clause 46, wherein the processor is further configured to determine a distance of a wearer from a near-field object based on the interpupillary distance, wherein the near-field object comprises one of a light-emitting screen or a book.

Clause 48. A spectacles-mounted ophthalmic monitoring system comprising: a spectacles frame comprising a left rim and a right rim; an image sensor coupled with the spectacles frame to capture images of a field of view of an eye disposed around at least a portion of a lower eyelid, a portion of an upper eyelid, and a portion of a sclera; and a processor configured to: activate the image sensor to capture an image of the field of view; segment the image into an eye portion and a background portion; identify, within the eye portion, a location of a lower eyelid; identify, within the eye portion, an upper edge of a tear film meniscus; and determine a height of the tear film meniscus based on the location of the lower eyelid and a location of the upper edge of the tear film meniscus.

Clause 49. The spectacles-mounted ophthalmic monitoring system of clause 48, wherein the processor is further configured to: compare the height of the tear film meniscus with a prior height of the tear film meniscus, wherein the prior height of the tear film meniscus is based on a prior image of the field of view captured prior to image of the field of view; and determine a change in tear film meniscus height from the prior height of the tear film meniscus to the height of the tear film meniscus.

Clause 50. The spectacles-mounted ophthalmic monitoring system of clause 49, wherein the processor is further configured to determine an eye strain metric based on the change in tear meniscus height.

Clause 51. The spectacles-mounted ophthalmic monitoring system of clause 48, wherein the processor is further configured to: identify a reflection of a light-emitting screen in the field of view of one or more images within a series of images; identify a blink rate using one or more images within the series of images; and determine an eye strain metric based on a combination of two or more of the height of the tear film meniscus, the reflection of the light-emitting screen, and the blink rate.

Clause 52. The spectacles-mounted ophthalmic monitoring system of clause 51, wherein to determine the eye strain metric, the processor is further configured to: compare the height of the tear film meniscus in a current image of the series of images with an average value of the height of the tear film meniscus in two or more other images in the series of images; and compare a current screen time with a screen time threshold, the current screen time comprising a duration between a first time corresponding to when a first image in the series of images in which the reflection of the light-emitting screen is identified and a current time corresponding to a current time when the current image is captured.

Clause 53. The spectacles-mounted ophthalmic monitoring system of clause 52, wherein to determine the eye strain metric, the processor is further configured to compare the blink rate with a blink rate threshold, the blink rate comprising an average number of blinks per minute during a current period of five minutes measured backward from the current image.

Clause 54. The spectacles-mounted ophthalmic monitoring system of clause 51, wherein to determine the eye strain metric, the processor is further configured to: compare the height of the tear film meniscus in a current image of the series of images with an average value of the height of the tear film meniscus in two or more other images in the series of images; and compare the blink rate with a blink rate threshold, the blink rate comprising an average number of blinks per minute during a current period of five minutes measured backward from the current image.

Clause 55. The spectacles-mounted ophthalmic monitoring system of clause 54, wherein to determine the eye strain metric, the processor is further configured to compare a current screen time with a screen time threshold, the current screen time comprising a duration between a first time corresponding to when a first image in the series of images in which the reflection of the light-emitting screen is identified and a current time corresponding to a current time when the current image is captured.

Clause 56. A computer-implemented method of monitoring an eye from a pair of spectacles comprising: under control of a computer system comprising one or more processors configured to execute specific computer-executable instructions, (a) activating an environmental sensor disposed on an eyeglasses frame; (b) detecting an environmental signal corresponding to a first state in which the eyeglasses frame is being worn by a wearer; (c) detecting an environmental signal corresponding to a second state in which the eyeglasses frame has been removed from a head of the wearer; (d) detecting an environmental signal corresponding to a second state in which the eyeglasses frame has been removed from a head of the wearer; (e) activating an image sensor to capture a plurality of images of an eye of the wearer; (f) tagging a first image of the plurality of images captured by the image sensor before step (c); (f) tagging a second image of the plurality of images captured by the image sensor after step (d); and (g) outputting the first image and the second image to a processor to conduct an analysis of a tear film meniscus in one or both of the first image and the second image.

Clause 57. The computer-implemented method of clause 56, further comprising detecting a scleral boundary in one or both of the first image and the second image.

Clause 58. The computer-implemented method of clause 56, further comprising evaluating one or both of the first image and the second image with a machine learning model to detect an edge of a tear film.

Clause 59. The computer-implemented method of clause 56, comparing a tear film height in the first image with a tear film height in the second image and generating a notification indicating a change in tear film height.

Clause 60. The computer-implemented method of clause 59, wherein generating the notification comprises generating the notification to the wearer of the eyeglasses frame.

Clause 61. The computer-implemented method of clause 59, wherein generating the notification comprises generating an alert on the eyeglasses frame.

Clause 62. The computer-implemented method of clause 59, wherein generating the notification comprises causing sending the notification to a user device paired with the eyeglasses frame.

Clause 63. The computer-implemented method of clause 59, wherein generating the notification comprises sending the notification to a third party not wearing the eyeglasses frame.

Clause 64. A spectacles-mounted ophthalmic monitoring system comprising: a spectacles frame comprising a left rim and a right rim; an image sensor coupled with the spectacles frame to capture images of a field of view of an eye; and a processor configured to: activate the image sensor to capture a first image of the field of view at a first time; activate the image sensor to capture a second image of the field of view at a second time subsequent to the first time; identify an ophthalmic feature associated with the eye based on at least one of the first image or the second image; and generate an output based on the ophthalmic feature.

Clause 65. The spectacles-mounted ophthalmic monitoring system of clause 64, wherein the ophthalmic feature comprises one of: occurrence of an eyelid blink, presence of a light-emitting screen reflection on the eye, presence of an eyepatch over the eye, or presence of a tear meniscus on the eye.

Clause 66. The spectacles-mounted ophthalmic monitoring system of clause 64, further comprising a light emitter, wherein the output comprises a command to activate the light emitter to emit a light.

Clause 67. The spectacles-mounted ophthalmic monitoring system of clause 64, further comprising an audio emitter, wherein the output comprises a command to activate the audio emitter to emit a sound.

Clause 68. The spectacles-mounted ophthalmic monitoring system of clause 64, further comprising a motor, wherein the output comprises a command to activate the motor to generate vibration.

Clause 69. The spectacles-mounted ophthalmic monitoring system of clause 64, further comprising a communication interface, wherein the output comprises a notification sent to device via the communication interface.

Clause 70. The spectacles-mounted ophthalmic monitoring system of clause 64, further comprising: a second processor; and a communication interface; wherein the processor is configured to cause the communication interface to send the output to the second processor; and wherein the second processor is configured to send a notification to a third party based on the output.

Clause 71. The spectacles-mounted ophthalmic monitoring system of clause 64, wherein the processor is further configured to identify a change, in an eyelid of the eye, from the first time to the second time based on the first image and the second image.

Clause 72. The spectacles-mounted ophthalmic monitoring system of clause 71, wherein the change in the eyelid comprises an eyelid blink, and wherein the output indicates occurrence of the eyelid blink.

Clause 73. The spectacles-mounted ophthalmic monitoring system of clause 72, wherein the processor is further configured to determine a blink rate based on the occurrence of the eyelid blink.

Clause 74. The spectacles-mounted ophthalmic monitoring system of clause 72, wherein to identify the eyelid blink, the processor is further configured to evaluate at least one of the first image or the second image using a machine learning model trained using a plurality of training data images.

Clause 75. The spectacles-mounted ophthalmic monitoring system of clause 72, wherein the processor is further configured to determine a velocity of the eyelid blink based on the change in the eyelid of the eye.

Clause 76. The spectacles-mounted ophthalmic monitoring system of clause 72, wherein the processor is further configured to determine a low point of the eyelid blink.

Clause 77. The spectacles-mounted ophthalmic monitoring system of clause 76, wherein the processor is further configured to determine that the eyelid blink is a partial blink based on the low point of the eyelid blink.

Clause 78. The spectacles-mounted ophthalmic monitoring system of clause 71, wherein the processor is further configured to: determine a first margin reflex distance for the eye based on the first image; determine a second margin reflex distance for the eye based on the second image; and determine a difference between the first margin reflex distance and the second margin reflex distance, wherein the change in the eyelid is identified based on the difference between the first margin reflex distance and the second margin reflex distance.

Clause 79. The spectacles-mounted ophthalmic monitoring system of clause 78, wherein the first margin reflex distance and second margin reflex distance are MRD1 scores.

Clause 80. The spectacles-mounted ophthalmic monitoring system of clause 78, wherein the first margin reflex distance and second margin reflex distance are MRD2 scores.

Clause 81. The spectacles-mounted ophthalmic monitoring system of clause 71, wherein the processor is further configured to: identify a first eyelid edge location at the first time based on first color data for a first subset of pixels of the first image; identify a second eyelid edge location at the second time based on second color data for a second subset of pixels of the second image; and determine a difference between the first eyelid edge location and the second eyelid edge location, wherein the change in the eyelid is identified based on the difference between the first eyelid edge location and the second eyelid edge location.

Clause 82. The spectacles-mounted ophthalmic monitoring system of clause 81, wherein the first color data and the second color data comprise in hue, saturation, and value (HSV) color space data.

Clause 83. The spectacles-mounted ophthalmic monitoring system of clause 64, wherein the processor is further configured to identify a reflection of a light-emitting screen in at least one of the first image or the second image.

Clause 84. The spectacles-mounted ophthalmic monitoring system of clause 83, wherein to identify the reflection of the light-emitting screen, the processor is further configured to evaluate at least one of the first image or the second image using a machine learning model trained using a plurality of training images.

Clause 85. The spectacles-mounted ophthalmic monitoring system of clause 83, further comprising a motion sensor configured to generate sensor data representing at least one of motion of the spectacles frame or orientation of the spectacles frame.

Clause 86. The spectacles-mounted ophthalmic monitoring system of clause 85, wherein the motion sensor comprises at least one of: an accelerometer, a gyroscope, and a magnetometer.

Clause 87. The spectacles-mounted ophthalmic monitoring system of clause 85, wherein the processor is further configured to: determine, based on the sensor data, a type of the light-emitting screen; and generate second output representing the type of the light-emitting screen.

Clause 88. The spectacles-mounted ophthalmic monitoring system of clause 87, further comprising a second processor configured to: receive the second output; and generate an eye strain metric based on the type of the light-emitting screen.

Clause 89. The spectacles-mounted ophthalmic monitoring system of clause 85, wherein the processor is further configured to: determine, based on the sensor data, a distance of a wearer from the light-emitting screen; and generate second output representing the distance of the wearer from the light-emitting screen.

Clause 90. The spectacles-mounted ophthalmic monitoring system of clause 89, further comprising a second processor configured to: receive the second output; and generate an eye strain metric based on the distance of the wearer from the light-emitting screen.

Clause 91. The spectacles-mounted ophthalmic monitoring system of clause 83, further comprising a second image sensor coupled with the spectacles frame to capture images of a second field of view of a second eye, wherein the processor is further configured to: activate the image sensor to capture a third image of the field of view at the first time; determine, based on the first image and the third image, a distance of a wearer from the light-emitting screen.

Clause 92. The spectacles-mounted ophthalmic monitoring system of clause 91, wherein the processor is further configured to: determine a distance between a first pupil of the eye and a second pupil of the second eye, wherein the distance of the wearer from the light-emitting screen is determined based on the distance between the first pupil and the second pupil.

Clause 93. The spectacles-mounted ophthalmic monitoring system of clause 64, wherein the processor is further configured to: determine an interpupillary distance based on one of the first image or the second image; determine, based on the interpupillary distance, a distance of a wearer from a near-field object; and generate second output representing the distance of the wearer from the near-field object.

Clause 94. The spectacles-mounted ophthalmic monitoring system of clause 93, wherein the near-field object comprises one of a light-emitting screen or a book.

Clause 95. The spectacles-mounted ophthalmic monitoring system of clause 64, further comprising: a computer-readable memory in communication with the processor; a communication interface in communication with the processor; a battery configured to power the processor and the communication interface; and a charging interface in communication with the battery; wherein the processor is further configured to cause storage of the first image in the computer-readable memory.

Clause 96. The spectacles-mounted ophthalmic monitoring system of clause 95, wherein the processor is further configured to: determine that the charging interface is charging the battery; and in response to determining that the charging interface is charging the battery, cause the communication interface to transmit the first image to a remote computing system.

Clause 97. The spectacles-mounted ophthalmic monitoring system of clause 95, wherein the processor is further configured to cause the communication interface to transmit the output to a remote computing system at a third time during which the charging interface is not charging the battery, wherein the output represents a blink rate.

Clause 98. The spectacles-mounted ophthalmic monitoring system of clause 64, wherein the processor is further configured to: determine that the image sensor is to operate in a first resolution mode of a plurality of resolution modes; wherein the first image and the second image are captured by the image sensor using the first resolution mode; determine, subsequent to the image sensor capturing the first image and the second image, that the image sensor is to operate in a second resolution mode of the plurality of resolution modes; and cause the image sensor to capture a third image in the second resolution mode at a third time.

Clause 99. The spectacles-mounted ophthalmic monitoring system of clause 98, wherein the processor is further configured to: determine that the eye is present in the field of view captured by the first image, wherein the image sensor captures the first image in a first resolution mode of a plurality of resolution modes; and determine, based on the eye being present in the field of view captured by the first image, that the image sensor is to operate in a second resolution mode of the plurality of resolution modes, wherein the image sensor captures the second image in the second resolution mode.

Clause 100. The spectacles-mounted ophthalmic monitoring system of clause 64, wherein the processor is further configured to determine a period of time to wait, after actuating the image sensor to capture the first image, before actuating the image sensor to capture the second image.

Clause 101. The spectacles-mounted ophthalmic monitoring system of clause 100, further comprising an environmental sensor configured to generate environmental data regarding at least one of: power usage, motion, temperature, humidity, battery life, or image quality, wherein the period of time to wait is determined based on the environmental data.

Clause 102. The spectacles-mounted ophthalmic monitoring system of clause 64, wherein the processor is further configured to: determine a current tear meniscus height based on the second image; compare the current tear meniscus height with a prior tear meniscus height, wherein the prior tear meniscus height is based on the first image; and determine an eye strain metric based on a change in tear meniscus height from the prior tear meniscus height to the current tear meniscus height.

Clause 103. The spectacles-mounted ophthalmic monitoring system of clause 102, wherein to determine the eye strain metric, the processor is further configured to use a current screen time value.

Clause 104. The spectacles-mounted ophthalmic monitoring system of clause 102, wherein to determine the eye strain metric, the processor is further configured to use a blink rate.

Clause 105. The spectacles-mounted ophthalmic monitoring system of clause 102, wherein to determine the eye strain metric, the processor is further configured to use a head movement metric.

Clause 106. A computer-implemented method comprising: under control of a processor of a spectacles-mounted ophthalmic monitoring system comprising a spectacles frame and an image sensor coupled with the spectacles frame to capture images of a field of view of an eye, activating the image sensor to capture a first image of the field of view at a first time; activating the image sensor to capture a second image of the field of view at a second time subsequent to the first time; identifying an ophthalmic feature associated with the eye based on at least one of the first image or the second image; and generating an output based on the ophthalmic feature.

Clause 107. The computer-implemented method of clause 106, further comprising identifying a change, in an eyelid of the eye, from the first time to the second time based on the first image and the second image.

Clause 108. The computer-implemented method of clause 107, further comprising: identifying a first eyelid edge location at the first time based on first color data for a first subset of pixels of the first image; identifying a second eyelid edge location at the second time based on second color data for a second subset of pixels of the second image; and determining a difference between the first eyelid edge location and the second eyelid edge location, wherein the change in the eyelid is identified based on the difference between the first eyelid edge location and the second eyelid edge location.

Clause 109. The computer-implemented method of clause 106, further comprising identifying a reflection of a light-emitting screen in at least one of the first image or the second image.

Clause 110. The computer-implemented method of clause 109, further comprising: determining, based on sensor data representing at least one of a motion or orientation of the spectacles frame, a type of the light-emitting screen; and generating second output representing the type of the light-emitting screen.

Clause 111. The computer-implemented method of clause 109, further comprising: determining, based on sensor data representing at least one of a motion or orientation of the spectacles frame, a distance of a wearer from the light-emitting screen; and generating second output representing the distance of the wearer from the light-emitting screen.

Clause 112. The computer-implemented method of clause 106, further comprising: determining an interpupillary distance based on one of the first image or the second image; determining, based on the interpupillary distance, a distance of a wearer from a near-field object; and generating second output representing the distance of the wearer from the near-field object.

Clause 113. The computer-implemented method of clause 106, further comprising: determining that the image sensor is to operate in a first resolution mode of a plurality of resolution modes; wherein the first image and the second image are captured by the image sensor using the first resolution mode; determining, subsequent to the image sensor capturing the first image and the second image, that the image sensor is to operate in a second resolution mode of the plurality of resolution modes; and causing the image sensor to capture a third image in the second resolution mode at a third time.

Clause 114. The computer-implemented method of clause 113, further comprising: determining that the eye is present in the field of view captured by the first image, wherein the image sensor captures the first image in a first resolution mode of a plurality of resolution modes; and determining, based on the eye being present in the field of view captured by the first image, that the image sensor is to operate in a second resolution mode of the plurality of resolution modes, wherein the image sensor captures the second image in the second resolution mode.

Clause 115. The computer-implemented method of clause 106, further comprising determining a period of time to wait, after actuating the image sensor to capture the first image, before actuating the image sensor to capture the second image.

Clause 116. The computer-implemented method of clause 106, further comprising: determining a current tear meniscus height based on the second image; comparing the current tear meniscus height with a prior tear meniscus height, wherein the prior tear meniscus height is based on the first image; and determining an eye strain metric based on a change in tear meniscus height from the prior tear meniscus height to the current tear meniscus height.

Clause 117. A system for machine learning training for detection of ophthalmic features, the system comprising: a spectacles frame comprising an image sensor, wherein the spectacles frame is configured to capture images of an eye of a wearer; an image data store storing a plurality of images generated using the image sensor; and a computing device comprising one or more processors and computer-readable memory, the computing device programmed by executable instructions to at least: generate a plurality of training data images using the plurality of images, wherein images in a first subset of the plurality of training data images are associated with label data representing a positive classification for presence of an ophthalmic feature, and wherein images in a second subset of the plurality of training data images are associated with label data representing a negative classification for presence of the ophthalmic feature; train a machine learning model using the plurality of training data images, wherein the machine learning model is trained to generate output data representing classification of at least a portion of an input image as one of negative or positive for presence of the ophthalmic feature; and distribute the machine learning model to one or more spectacles-mounted ophthalmic monitoring systems.

Clause 118. The system of clause 117, further comprising the one or more spectacles-mounted ophthalmic monitoring systems, wherein a spectacles-mounted ophthalmic monitoring system of the one or more spectacles-mounted ophthalmic monitoring systems comprises the spectacles frame, and wherein the spectacles-mounted ophthalmic monitoring system receives the machine learning model from the computing device.

Clause 119. The system of clause 118, wherein the spectacles-mounted ophthalmic monitoring system comprises a processor and an output device, and wherein the processor is configured to: analyze, using the machine learning model, image data generated by the image sensor; and cause the output device to present output indicating presence of the ophthalmic feature based on results of analyzing the image data using the machine learning model.

Clause 120. The system of clause 117, wherein the machine learning model comprises a convolutional neural network.

Clause 121. The system of clause 117, wherein to train the machine learning model, the computing device is further programmed by the executable instructions to: obtain the machine learning model, wherein the machine learning model comprises a plurality of parameters; generate a training data output vector using the machine learning model and a training data image of the plurality of training data images, wherein the training data output vector represents a classification of at least a portion of the training data image as one of negative or positive for presence of the ophthalmic feature; compute a gradient based on a difference between the training data output vector and label data associated with the training data image; and update a parameter of the plurality of parameters using the gradient.

Clause 122. The system of clause 121, wherein the computing device is further programmed by the executable instructions to determine the difference between the training data output vector and the label data associated with the training data image using a loss function.

Clause 123. The system of clause 117, wherein the computing device is further programmed by the executable instructions to initialize a parameter of the machine learning model to a pseudo-random value.

Clause 124. The system of clause 117, further comprising a second spectacles frame, wherein the image data store stores a second plurality of images generated using a second image sensor of the second spectacles frame, and wherein plurality of training data images are generated using the plurality of images and the second plurality of images.

Clause 125. The system of clause 117, wherein first label data associated with a first image of the plurality of images represents a classification of a type of ophthalmic feature.

Clause 126. The system of clause 117, wherein first label data associated with a first image of the plurality of images represents a location of an ophthalmic feature within the first image.

Clause 127. The system of clause 126, wherein the ophthalmic feature comprises one of: occurrence of an eyelid blink, presence of a light-emitting screen reflection on an eye, presence of an eyepatch over the eye, presence of a tear meniscus on the eye, blink rate, screen time, tear meniscus height, or eyedrop.

Clause 128. The system of clause 117, wherein the computing device is further programmed by the executable instructions to generate a plurality of training data input items using the plurality of training data images and augmentation data, wherein the augmentation data represents one or more of: a time of image capture, ambient lighting conditions associated with image capture, a screen brightness, a presence of glare, a head position, de-identified wearer health data, an MRD1 value, an MRD2 value, an interpupillary distance, a blink rate, a blink strength, a screen time duration, a tear meniscus height, a tear break up time, a relative humidity, a temperature, a head position, a motion, a user interaction, an eyedrop detection, an eyedrop warning history, and an intraocular pressure.

Clause 129. The system of clause 117, wherein the computing device is further programmed by the executable instructions to: obtain user interface data representing a user interaction with the spectacles frame; determine, based on the user interface data, to label a first image of the plurality of images with first label data representing one of a positive classification or negative classification for presence of an ophthalmic feature; and generate the first label data, wherein the first label data is used to generate the plurality of training data images.

Clause 130. The system of clause 129, wherein the user interface data represents the user interaction in response to presentation of a notification.

Clause 131. The system of clause 129, wherein the user interface data represents the user interaction to mark occurrence of an event.

Terminology and Additional Considerations

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

What is claimed is:

1. A spectacles-mounted ophthalmic monitoring system, comprising:
   a spectacles frame comprising a left rim and a right rim;
   an image sensor coupled with the spectacles frame to capture images of a field of view of an eye disposed around at least a portion of a lower eyelid, a portion of an upper eyelid, and a portion of a sclera; and
   a processor configured to:
   (a) activate the image sensor to capture a series of images of the field of view;

(b) identify a height of a tear film meniscus within the field of view of one or more images within the series of images;

(c) identify a reflection of a light-emitting screen in the field of view of one or more images within the series of images;

(d) identify a blink rate of one or more images within the series of images; and (e) determine an eye strain metric based on a combination of two or more of the height of the tear film meniscus identified in (a), the reflection of the light-emitting screen identified in (b), and the blink rate identified in (c).

2. The spectacles-mounted ophthalmic monitoring system of claim 1, wherein determining an eye strain metric comprises comparing the height of the tear film meniscus in a current image of the series of images with an average value of the height of the tear film meniscus in two or more other images in the series of images and comparing a current screen time with a screen time threshold, the current screen time comprising a duration between a first time corresponding to when a first image in the series of images in which the reflection of the light-emitting screen is identified and a current time corresponding to a current time when the current image is captured.

3. The spectacles-mounted ophthalmic monitoring system of claim 2, wherein determining the eye strain metric further comprises comparing the blink rate with a blink rate threshold, the blink rate comprising an average number of blinks per minute during a current period of five minutes measured backward from the current image.

4. The spectacles-mounted ophthalmic monitoring system of claim 1, wherein determining an eye strain metric comprises comparing the height of the tear film meniscus in a current image of the series of images with an average value of the height of the tear film meniscus in two or more other images in the series of images and comparing the blink rate with a blink rate threshold, the blink rate comprising an average number of blinks per minute during a current period of five minutes measured backward from the current image.

5. The spectacles-mounted ophthalmic monitoring system of claim 4, wherein determining the eye strain metric further comprises comparing a current screen time with a screen time threshold, the current screen time comprising a duration between a first time corresponding to when a first image in the series of images in which the reflection of the light-emitting screen is identified and a current time corresponding to a current time when the current image is captured.

6. The spectacles-mounted ophthalmic monitoring system of claim 1, wherein the processor is further configured to:

compare the height of the tear film meniscus with a prior height of the tear film meniscus, wherein the prior height of the tear film meniscus is based on a first image of the series of images, and wherein the height of the tear film meniscus is based on a second image of the series of images captured after the first image; and determine a change in tear meniscus film height from the prior height of the tear film meniscus to the height of the tear film meniscus.

7. The spectacles-mounted ophthalmic monitoring system of claim 6, wherein to determine the eye strain metric, the processor is further configured to use the change in tear meniscus height.

8. The spectacles-mounted ophthalmic monitoring system of claim 1, wherein to determine the eye strain metric, the processor is further configured to use a head movement metric.

9. The spectacles-mounted ophthalmic monitoring system of claim 1, wherein to identify the reflection of the light-emitting screen, the processor is further configured to evaluate at least one image of the series of images using a machine learning model trained using a plurality of training images.

10. The spectacles-mounted ophthalmic monitoring system of claim 1, further comprising a motion sensor configured to generate sensor data representing at least one of motion of the spectacles frame or orientation of the spectacles frame.

11. The spectacles-mounted ophthalmic monitoring system of claim 10, wherein the motion sensor comprises at least one of: an accelerometer, a gyroscope, and a magnetometer.

12. The spectacles-mounted ophthalmic monitoring system of claim 10, wherein the processor is further configured to determine, based on the sensor data, a type of the light-emitting screen.

13. The spectacles-mounted ophthalmic monitoring system of claim 12, wherein to determine the eye strain metric, the processor is further configured to use the type of the light-emitting screen.

14. The spectacles-mounted ophthalmic monitoring system of claim 10, wherein the processor is further configured to determine, based on the sensor data, a distance of a wearer from the light-emitting screen.

15. The spectacles-mounted ophthalmic monitoring system of claim 14, wherein to determine the eye strain metric, the processor is further configured to use the distance of the wearer from the light-emitting screen.

16. The spectacles-mounted ophthalmic monitoring system of claim 4, further comprising a second image sensor coupled with the spectacles frame to capture images of a second field of view of a second eye, wherein the processor is further configured to:

activate the image sensor to capture a second series of images of the second field of view; and determine in interpupillary distance between a first pupil of the eye and a second pupil of the second eye.

17. The spectacles-mounted ophthalmic monitoring system of claim 16, wherein the processor is further configured to determine a distance of a wearer from a near-field object based on the interpupillary distance, wherein the near-field object comprises one of a light-emitting screen or a book.

18. A spectacles-mounted ophthalmic monitoring system comprising:

a spectacles frame comprising a left rim and a right rim;

an image sensor coupled with the spectacles frame to capture images of a field of view of an eye disposed around at least a portion of a lower eyelid, a portion of an upper eyelid, and a portion of a sclera; and a processor configured to:

activate the image sensor to capture an image of the field of view;

segment the image into an eye portion and a background portion;

identify, within the eye portion, a location of a lower eyelid;

identify, within the eye portion, an upper edge of a tear film meniscus; and determine a height of the tear film meniscus based on the location of the lower eyelid and a location of the upper edge of the tear film meniscus.

19. The spectacles-mounted ophthalmic monitoring system of claim 18, wherein the processor is further configured to:
- compare the height of the tear film meniscus with a prior height of the tear film meniscus, wherein the prior height of the tear film meniscus is based on a prior image of the field of view captured prior to image of the field of view; and
- determine a change in tear film meniscus height from the prior height of the tear film meniscus to the height of the tear film meniscus.

20. The spectacles-mounted ophthalmic monitoring system of claim 19, wherein the processor is further configured to determine an eye strain metric based on the change in tear meniscus height.

21. The spectacles-mounted ophthalmic monitoring system of claim 18, wherein the processor is further configured to:
- identify a reflection of a light-emitting screen in the field of view of one or more images within a series of images;
- identify a blink rate using one or more images within the series of images; and
- determine an eye strain metric based on a combination of two or more of the height of the tear film meniscus, the reflection of the light-emitting screen, and the blink rate.

22. The spectacles-mounted ophthalmic monitoring system of claim 21, wherein to determine the eye strain metric, the processor is further configured to:
- compare the height of the tear film meniscus in a current image of the series of images with an average value of the height of the tear film meniscus in two or more other images in the series of images; and
- compare a current screen time with a screen time threshold, the current screen time comprising a duration between a first time corresponding to when a first image in the series of images in which the reflection of the light-emitting screen is identified and a current time corresponding to a current time when the current image is captured.

23. The spectacles-mounted ophthalmic monitoring system of claim 22, wherein to determine the eye strain metric, the processor is further configured to compare the blink rate with a blink rate threshold, the blink rate comprising an average number of blinks per minute during a current period of five minutes measured backward from the current image.

24. The spectacles-mounted ophthalmic monitoring system of claim 21, wherein to determine the eye strain metric, the processor is further configured to:
- compare the height of the tear film meniscus in a current image of the series of images with an average value of the height of the tear film meniscus in two or more other images in the series of images; and
- compare the blink rate with a blink rate threshold, the blink rate comprising an average number of blinks per minute during a current period of five minutes measured backward from the current image.

25. The spectacles-mounted ophthalmic monitoring system of claim 24, wherein to determine the eye strain metric, the processor is further configured to compare a current screen time with a screen time threshold, the current screen time comprising a duration between a first time corresponding to when a first image in the series of images in which the reflection of the light-emitting screen is identified and a current time corresponding to a current time when the current image is captured.

* * * * *

UNITED STATES PATENT AND TRADEMARK OFFICE
CERTIFICATE OF CORRECTION

| | |
|---|---|
| PATENT NO. | : 11,806,078 B1 |
| APPLICATION NO. | : 18/309662 |
| DATED | : November 7, 2023 |
| INVENTOR(S) | : Joshua Park |

It is certified that error appears in the above-identified patent and that said Letters Patent is hereby corrected as shown below:

In the Specification

In Column 3, Line 7, delete "spectacles-a right rim;" and insert --spectacles-mounted ophthalmic monitoring system including: a spectacles frame including a left rim and a right rim;--.

In Column 3, Line 53, delete "spectacles-a right rim;" and insert --spectacles-mounted ophthalmic monitoring system including: a spectacles frame including a left rim and a right rim;--.

In Column 4, Line 31, delete "spectacles-a right rim;" and insert --spectacles-mounted ophthalmic monitoring system including: a spectacles frame including a left rim and a right rim;--.

In Column 40, Line 7, delete "image" and insert --image.--.

In the Claims

In Column 65, Claim 1, Line 11 (approx.), delete "(a)" and insert --(b)--.

In Column 65, Claim 1, Line 12 (approx.), delete "(b)" and insert --(c)--.

In Column 65, Claim 1, Line 13 (approx.), delete "(c)" and insert --(d)--.

Signed and Sealed this
Twentieth Day of February, 2024

Katherine Kelly Vidal
*Director of the United States Patent and Trademark Office*